(12) United States Patent
Mizuki et al.

(10) Patent No.: US 8,932,735 B2
(45) Date of Patent: Jan. 13, 2015

(54) AROMATIC AMINE DERIVATIVE AND ORGANIC ELECTROLUMINESCENT ELEMENT COMPRISING THE SAME

(75) Inventors: Yumiko Mizuki, Sodegaura (JP); Masakazu Funahashi, Sodegaura (JP)

(73) Assignee: Idemitsu Kosan Co., Ltd., Tokyo (JP)

( * ) Notice: Subject to any disclaimer, the term of this patent is extended or adjusted under 35 U.S.C. 154(b) by 385 days.

(21) Appl. No.: 13/266,000

(22) PCT Filed: Apr. 22, 2010

(86) PCT No.: PCT/JP2010/002918
§ 371 (c)(1),
(2), (4) Date: Oct. 24, 2011

(87) PCT Pub. No.: WO2010/122799
PCT Pub. Date: Oct. 28, 2010

(65) Prior Publication Data
US 2012/0043533 A1    Feb. 23, 2012

(30) Foreign Application Priority Data
Apr. 24, 2009 (JP) .................................. 2009-106001

(51) Int. Cl.
| | | |
|---|---|---|
| *H01L 51/50* | (2006.01) | |
| *C07D 307/91* | (2006.01) | |
| *C07C 211/56* | (2006.01) | |

(Continued)

(52) U.S. Cl.
CPC ............ *C07D 307/91* (2013.01); *C07C 211/56* (2013.01); *C07C 211/58* (2013.01); *C07C 211/61* (2013.01); *C07C 255/58* (2013.01); *C07C 209/86* (2013.01); *C07D 235/08* (2013.01); *C07D 239/42* (2013.01); *C07D 333/20* (2013.01); *C07D 333/76* (2013.01); *C07D 405/10* (2013.01); *C07F 7/0809* (2013.01); *C07F 7/0818* (2013.01); *C09K 11/06* (2013.01); *H01L 51/0059* (2013.01); *H01L 51/006* (2013.01); *H01L 51/0073* (2013.01); *H01L 51/0094* (2013.01); *H05B 33/14* (2013.01); *C07C 2103/18* (2013.01); *C07C 2103/26* (2013.01); *C07C 2103/42* (2013.01); *C07C 2103/94* (2013.01); *C09K 2211/1007* (2013.01); *C09K 2211/1011* (2013.01); *C09K 2211/1029* (2013.01); *C09K 2211/1088* (2013.01); *C09K 2211/1092* (2013.01); *H01L 51/5012* (2013.01); *Y10S 428/917* (2013.01)
USPC ........... 428/690; 428/917; 313/504; 313/505; 313/506; 257/40; 257/E51.05; 257/E51.026; 257/E51.032; 564/26; 564/426; 564/434

(58) Field of Classification Search
USPC .................. 428/690, 917; 313/504, 505, 506; 257/40, E51.05, E51.026, E51.032; 564/26, 426, 434
See application file for complete search history.

(56) References Cited

U.S. PATENT DOCUMENTS

| | | | |
|---|---|---|---|
| 5,034,294 A | 7/1991 | Go et al. | |
| 5,443,922 A * | 8/1995 | Nishizaki et al. | ............. 428/690 |
| 5,667,925 A | 9/1997 | Tsuruoka et al. | |
| 2001/0033944 A1* | 10/2001 | Onikubo et al. | ............. 428/690 |
| 2006/0134458 A1 | 6/2006 | Kawamura et al. | |

(Continued)

FOREIGN PATENT DOCUMENTS

| | | | | |
|---|---|---|---|---|
| JP | 01-106070 | * | 4/1989 | ............. G03G 5/06 |
| JP | 2 210357 | | 8/1990 | |

(Continued)

OTHER PUBLICATIONS

Sun et. al., Effects of the structure of the branches on the two-photon absorption properties for the multi-branched molecules with nitrogen (N) as coupling center, 2008, Science China Series B: Chemistry, vol. 51, No. 1, pp. 92-96.*

(Continued)

*Primary Examiner* — Gregory Clark
(74) *Attorney, Agent, or Firm* — Oblon, Spivak, McClelland, Maier & Neustadt, L.L.P.

(57) ABSTRACT

An aromatic amine derivative represented by the following formula (1):

wherein $A^1$ is a substituted or unsubstituted alkyl group, a substituted or unsubstituted aromatic group, a substituted or unsubstituted heterocyclic group or an organic group represented by the following formula (2):

wherein $X^1$, $X^2$ and $X^3$ are independently a substituted or unsubstituted aromatic group or a substituted or unsubstituted heterocyclic group;

$X^1$ and $X^2$ are linkage groups which are different from each other; and $B^1$, $B^2$ and $B^3$ are independently a substituted or unsubstituted aromatic group or a substituted or unsubstituted heterocyclic group.

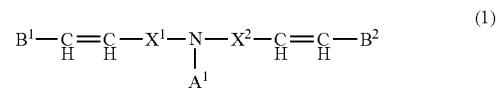

(1)

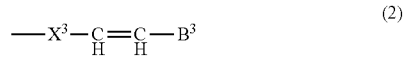

(2)

20 Claims, No Drawings

(51) Int. Cl.

| | |
|---|---|
| C07C 211/58 | (2006.01) |
| C07C 211/61 | (2006.01) |
| C07C 255/58 | (2006.01) |
| C07C 209/86 | (2006.01) |
| C07D 235/08 | (2006.01) |
| C07D 239/42 | (2006.01) |
| C07D 333/20 | (2006.01) |
| C07D 333/76 | (2006.01) |
| C07D 405/10 | (2006.01) |
| C07F 7/08 | (2006.01) |
| C09K 11/06 | (2006.01) |
| H01L 51/00 | (2006.01) |
| H05B 33/14 | (2006.01) |

(56) References Cited

U.S. PATENT DOCUMENTS

| | | |
|---|---|---|
| 2007/0185303 A1 | 8/2007 | Stossel et al. |
| 2007/0207395 A1 | 9/2007 | Kondoh et al. |
| 2008/0108811 A1 | 5/2008 | Yabunouchi et al. |
| 2008/0145698 A1 | 6/2008 | Heil et al. |
| 2008/0297037 A1* | 12/2008 | Vestweber et al. ............ 313/504 |
| 2009/0159874 A1 | 6/2009 | Vestweber et al. |

FOREIGN PATENT DOCUMENTS

| | | |
|---|---|---|
| JP | 04 184892 | 7/1992 |
| JP | 8 305053 | 11/1996 |
| JP | 2004 026732 | 1/2004 |
| JP | 2004 262761 | 9/2004 |
| JP | 2007 121558 | 5/2007 |
| JP | 2007 233305 | 9/2007 |
| JP | 2008 504247 | 2/2008 |
| WO | 2006 073059 | 7/2006 |
| WO | 2007 065547 | 6/2007 |
| WO | 2007 065549 | 6/2007 |
| WO | WO 2008/156089 A1 | 12/2008 |

OTHER PUBLICATIONS

Fukuzaki, E., et al., "Room-Temperature High-Spin Organic Single Molecule: Nanometer-Sized and Hyperbranched Poly[1,2,(4)-phenylenevinyleneanisylaminium]," Journal of the American Chemical Society, vol. 128, No. 3, pp. 996-1001, (2006).

International Search Report Issued May 25, 2010 in PCT/JP10/002918 Filed Apr. 22, 2010.

Extended European Search Report issued Sep. 25, 2012, in European Patent Application No. 10766860.0.

* cited by examiner

AROMATIC AMINE DERIVATIVE AND ORGANIC ELECTROLUMINESCENT ELEMENT COMPRISING THE SAME

TECHNICAL FIELD

The invention relates to an aromatic amine derivative and an organic electroluminescence device using the same. In particular, the invention relates to an aromatic amine derivative which enables an organic electroluminescence device which can emit highly pure blue color light, has a high luminous efficiency and has a prolonged lifetime, as well as to an organic electroluminescence device which can emit highly pure blue light, has a high luminous efficiency and has a prolonged lifetime.

BACKGROUND ART

An organic electroluminescence (EL) device is a promising solid-state emitting type inexpensive and large full-color display device, and has been extensively developed. In general, an organic EL device includes an emitting layer and a pair of opposing electrodes holding the emitting layer therebetween. Emission is a phenomenon in which when an electric field is applied between the both electrodes, electrons are injected from the cathode and holes are injected from the anode. The electrons recombine with the holes in the emitting layer to produce an excited state, and energy is emitted as light when the excited state returns to the ground state.

Conventional organic EL devices have a higher driving voltage than that of an inorganic light-emitting diode. The luminance or luminous efficiency thereof is also low, and their properties tend to deteriorate significantly. For these reasons, conventional organic EL devices have not been put in a practical use. Although recent organic EL devices have been improved gradually, further improvement in luminous efficiency, prolongation in lifetime or the like has been demanded.

In order to attain a high luminous efficiency and a long life, some organic EL devices and some materials for an organic EL device have been proposed (Patent Documents 1 to 4). However, further improvement has been demanded.

RELATED ART DOCUMENTS

Patent Documents

Patent Document 1: JP-A-H04-184892
Patent Document 2: WO07/065549
Patent Document 3: WO07/065547
Patent Document 4: WO06/000389

SUMMARY OF THE INVENTION

An object of the invention is to provide an aromatic amine derivative which can improve blue color purity, luminous efficiency and lifetime of an organic EL device.

An object of the invention is to provide an organic EL device which can emit highly pure blue color light, has a high luminous efficiency and has a prolonged lifetime.

According to the invention, the following aromatic amine derivative or the like can be provided.

1. An aromatic amine derivative represented by the following formula (1):

$$B^1-\underset{H}{C}=\underset{H}{C}-X^1-\underset{\underset{A^1}{|}}{N}-X^2-\underset{H}{C}=\underset{H}{C}-B^2 \quad (1)$$

wherein $A^1$ is a substituted or unsubstituted alkyl group, a substituted or unsubstituted aromatic group, a substituted or unsubstituted heterocyclic group or an organic group represented by the following formula (2):

$$-X^3-\underset{H}{C}=\underset{H}{C}-B^3 \quad (2)$$

wherein $X^1$, $X^2$ and $X^3$ are independently a substituted or unsubstituted aromatic group or a substituted or unsubstituted heterocyclic group;

$X^1$ and $X^2$ are linkage groups which are different from each other; and $B^1$, $B^2$ and $B^3$ are independently a substituted or unsubstituted aromatic group or a substituted or unsubstituted heterocyclic group.

2. The aromatic amine derivative according to 1 which is represented by the following formula (3):

$$B^1-\underset{H}{C}=\underset{H}{C}-X^1-\underset{\underset{\underset{\underset{B^3}{|}}{\underset{HC}{\|}}}{\underset{X^3}{|}}}{N}-X^2-\underset{H}{C}=\underset{H}{C}-B^2 \quad (3)$$

wherein $X^1$, $X^2$, $X^3$, $B^1$, $B^2$ and $B^3$ are the same as those defined in the formula (1).

3. The aromatic amine derivative according to 1 or 2, wherein one of $X^1$ and $X^2$ is a substituted or unsubstituted fused aromatic ring group having 10 to 30 carbon atoms that form a ring (hereinafter referred to as the "ring carbon atom(s)") or a fused heterocyclic group having 10 to 30 atoms that form a ring (hereinafter referred to as the "ring atoms"), and the other of $X^1$ and $X^2$ is a substituted or unsubstituted non-fused aromatic ring group having 6 to 30 ring carbon atoms or a non-fused heterocyclic group having 6 to 30 ring atoms.

4. The aromatic amine derivative according to any one of 1 to 3, which is represented by the following formula (4):

wherein $X^2$, $X^3$, $B^1$, $B^2$ and $B^3$ are the same as those defined in the formula (1);

$R^1$ and $R^2$ are independently an alkyl group, an aromatic group, a fluorine atom, an alkoxy group or a substituted or unsubstituted silyl group; and $R^1$ and $R^2$ may be combined with each other to form a saturated or unsaturated ring.

5. The aromatic amine derivative according to any one of 1 to 3 which is represented by the following formula (5):

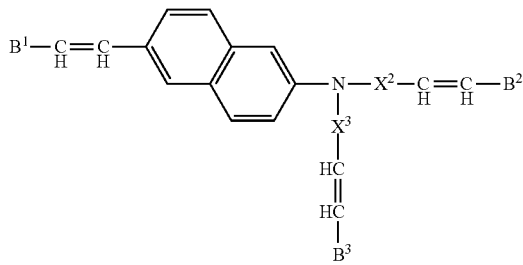

(5)

wherein $X^2$, $X^3$, $B^1$, $B^2$ and $B^3$ are the same as those defined in the formula (1).

6. The aromatic amine derivative according to any one of 1 to 5, wherein $X^2$ and $X^3$ are both substituted or unsubstituted phenylene groups.

7. The aromatic amine derivative according to any one of 1 to 5, wherein $X^3$ is a substituted or unsubstituted fluorenylene group.

8. The aromatic amine derivative according to any one of 1 to 7, wherein any of the aromatic groups or the heterocyclic groups represented by $B^1$, $B^2$ and $B^3$ has a substituted or unsubstituted silyl group as a substituent.

9. The aromatic amine derivative according to 1, wherein $A^1$ is a substituted or unsubstituted aromatic group or a substituted or unsubstituted heterocyclic group.

10. An organic electroluminescence device which uses the aromatic amine derivative according to any one of 1 to 9.

11. The organic electroluminescence device according to 10 which uses the aromatic amine derivative as an emitting material or a hole-transporting material.

12. An organic electroluminescence device which comprises between an anode and a cathode one or more organic thin film layers comprising an emitting layer, wherein at least one layer of the organic thin film layers comprises the aromatic amine derivative according to any one of 1 to 9.

13. The organic electroluminescence device according to 12, wherein the emitting layer comprises the aromatic amine derivative.

14. The organic electroluminescence device according to 13, wherein the emitting layer comprises at least one kind of the aromatic amine derivative and at least one kind of the anthracene derivative represented by the following formula (2A):

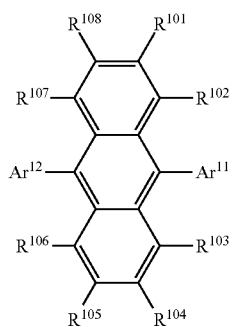

(2A)

in the formula (2A), $Ar^{11}$ and $Ar^{12}$ are independently a substituted or unsubstituted monocyclic group having 5 to 50 ring atoms or a substituted or unsubstituted fused ring group having 8 to 50 ring atoms; and $R^{101}$ to $R^{108}$ are independently a hydrogen atom, a substituted or unsubstituted monocyclic group having 5 to 50 ring atoms, a substituted or unsubstituted fused ring group having 8 to 50 ring atoms, a substituted or unsubstituted alkyl group having 1 to 50 carbon atoms, a substituted or unsubstituted cycloalkyl group having 3 to 50 ring carbon atoms, a substituted or unsubstituted alkoxy group having 1 to 50 carbon atoms, a substituted or unsubstituted aralkyl group having 7 to 50 carbon atoms, a substituted or unsubstituted aryloxy group having 6 to 50 ring carbon atoms, a substituted or unsubstituted silyl group, a halogen atom or a cyano group.

According to the invention, it is possible to provide an aromatic amine derivative which can improve the blue color purity, luminous efficiency and lifetime of an organic EL device.

According to the invention, it is possible to provide an organic EL device which can emit highly pure blue color light, has a high luminous efficiency and a prolonged lifetime.

MODE FOR CARRYING OUT THE INVENTION

The aromatic amine derivative of the invention is a compound represented by the following formula (1):

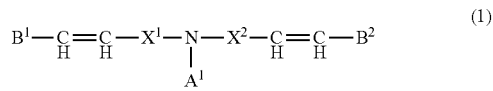

(1)

wherein $A^1$ is a substituted or unsubstituted alkyl group, a substituted or unsubstituted aromatic group, a substituted or unsubstituted heterocyclic group or an organic group represented by the following formula (2):

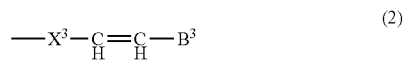

(2)

wherein $X^1$, $X^2$ and $X^3$ are independently a substituted or unsubstituted aromatic group or a substituted or unsubstituted heterocyclic group;

$X^1$ and $X^2$ are linkage groups which are different from each other; and $B^1$, $B^2$ and $B^3$ are independently a substituted or unsubstituted aromatic group or a substituted or unsubstituted heterocyclic group. Preferably, $A^1$ is a substituted or unsubstituted aromatic group or a substituted or unsubstituted heterocyclic group.

In the formula (1), $X^1$ and $X^2$ are linkage groups which are different from each other.

In the aromatic amine derivative of the invention, it is assumed that the skeleton between the nitrogen atom and the two double-bonded sites relates to emission. By allowing the luminescent center structure to be asymmetrical, effects of preventing stacking between molecules can be obtained. In particular, it is assumed that significant stacking prevention effects are obtained in the vicinity of the luminescent center structure. By such effects, the aromatic amine derivative of the invention can emit highly pure blue color light, has an improved luminous efficiency and has a prolonged lifetime.

As the substituted or unsubstituted alkyl group represented by $A^1$, a substituted or unsubstituted alkyl group having 1 to 10 (preferably 1 to 8, more preferably 1 to 6) carbon atoms can be given. Specific examples thereof include a substituted or unsubstituted methyl group, a substituted or unsubstituted ethyl group, a substituted or unsubstituted propyl group, a substituted or unsubstituted isopropyl group, a substituted or unsubstituted n-butyl group, a substituted or unsubstituted s-butyl group, a substituted or unsubstituted isobutyl group, a substituted or unsubstituted t-butyl group, a substituted or unsubstituted n-pentyl group, a substituted or unsubstituted n-hexyl group, a substituted or unsubstituted n-heptyl group, a substituted or unsubstituted n-octyl group, a substituted or unsubstituted fluoromethyl group, a substituted or unsubstituted difluoromethyl group, a substituted or unsubstituted trifluoromethyl group, a substituted or unsubstituted fluoroethyl group, a substituted or unsubstituted trifluoromethylmethyl group, a substituted or unsubstituted aminomethyl group, a substituted or unsubstituted cyanomethyl group, a substituted or unsubstituted cyanoethyl group, a substituted or unsubstituted nitromethyl group and a substituted or unsubstituted nitroethyl group.

As the substituted or unsubstituted aromatic group represented by $A^1$ and $B^1$ to $B^3$, a substituted or unsubstituted aromatic group having 6 to 30 (preferably 6 to 20, more preferably 6 to 12) ring carbon atoms can be given. Specific examples thereof include a substituted or unsubstituted phenyl group, a substituted or unsubstituted naphthyl group, a substituted or unsubstituted anthryl group, a substituted or unsubstituted phenanthryl group, a substituted or unsubstituted naphthacenyl group, a substituted or unsubstituted anthracenyl group, a substituted or unsubstituted chrycenyl group, a substituted or unsubstituted fluorenyl group, a substituted or unsubstituted triphenylenyl group, a substituted or unsubstituted pyrenyl group, a substituted or unsubstituted biphenyl group, a substituted or unsubstituted p-terphenyl group, a substituted or unsubstituted m-terphenyl group, a substituted or unsubstituted o-tolyl group, a substituted or unsubstituted m-tolyl group, a substituted or unsubstituted p-tolyl group, a substituted or unsubstituted p-t-butylphenyl group, a substituted or unsubstituted p-(phenylpropyl)phenyl group, a substituted or unsubstituted methylnaphthyl group, a substituted or unsubstituted methylanthryl group, a substituted or unsubstituted methylbiphenyl group, a substituted or unsubstituted t-butyl-p-terphenyl group, a substituted or unsubstituted dimethylfluorenyl group, a substituted or unsubstituted m-biphenyl group, a substituted or unsubstituted o-biphenyl group, a substituted or unsubstituted 4-(2-phenylpropane-2-yl)phenyl group, a substituted or unsubstituted fluoranthenyl group, a substituted or unsubstituted 9,9'-dimethylfluorenyl group, a substituted or unsubstituted benzo-9,9'-dimethylfluorenyl group and a substituted or unsubstituted dibenzo-9,9'-dimethylfluorenyl group. In addition, an aromatic group obtained by combining a phenyl group, a phenylene group, a naphthyl group, and/or a naphthalene group (for example, a phenynaphthyl group, a naphthylphenyl group, a naphthylnaphthyl group, a naphthylnaphthylnaphthyl group, a phenylphenylnaphthyl group, a naphthylnaphthylphenyl group, a naphthylphenylnaphthyl group, a naphthylphenylphenyl group, a phenylnaphthylnaphthyl group, and a phenylnaphthylphenyl group) can be given.

As the group represented by $A^1$ and $B^1$ to $B^3$, aromatic groups such as a substituted or unsubstituted phenyl group, a substituted or unsubstituted biphenyl group, a substituted or unsubstituted terphenyl group, a substituted or unsubstituted naphthyl group, a substituted or unsubstituted phenanthryl group, a substituted or unsubstituted anthracenyl group a substituted or unsubstituted chrysenyl group, a substituted or unsubstituted fluorenyl group are preferable.

It is particularly preferred that $A^1$ be a substituted or unsubstituted phenyl group, a substituted or unsubstituted biphenyl group, a substituted or unsubstituted naphthyl group and a substituted or unsubstituted fluorenyl group.

As the substituted or unsubstituted heterocyclic group represented by $A^1$ and $B^1$ to $B^3$, a heterocyclic group having 5 to 30 (preferably 5 to 20, more preferably 5 to 12) ring atoms can be given. Specific examples thereof include a substituted or unsubstituted pyrrolyl group, a substituted or unsubstituted pyrazinyl group, a substituted or unsubstituted pyridinyl group, a substituted or unsubstituted indolyl group, a substituted or unsubstituted isoindolyl group, a substituted or unsubstituted furyl group, a substituted or unsubstituted benzofuranyl group, a substituted or unsubstituted dibenzofuranyl group, a substituted or unsubstituted isobenzofuranyl group, a substituted or unsubstituted quinolyl group, a substituted or unsubstituted isoquinolyl group, a substituted or unsubstituted quinoxalinyl group, a substituted or unsubstituted carbazolyl group, a substituted or unsubstituted phenanthridinyl group, a substituted or unsubstituted acrydinyl group, a substituted or unsubstituted phenanthrolinyl group, a substituted or unsubstituted phenadinyl group, a substituted or unsubstituted phenothiadinyl group, a substituted or unsubstituted phenoxazinyl group, a substituted or unsubstituted oxazolyl group, a substituted or unsubstituted oxadiazolyl group, a substituted or furazanyl group, a substituted or unsubstituted thienyl group, a substituted or unsubstituted methylpyrrolyl group, a substituted or unsubstituted t-butylpyrrolyl group, a substituted or unsubstituted (phenylpropyl)pyrrolyl group, a substituted or unsubstituted methylindolyl group, a substituted or unsubstituted t-butylindolyl group, a substituted or unsubstituted dibenzothiophenyl group, a substituted or unsubstituted pyrimidinyl group and a substituted or unsubstituted pyridazinyl group.

Of these, a substituted or unsubstituted dibenzofuranyl group, a substituted or unsubstituted pyridinyl group and a substituted or unsubstituted carbazolyl group can preferably be given.

It is particularly preferred that $A^1$ be a substituted or unsubstituted dibenzofuranyl group.

As the substituted or unsubstituted aromatic group represented by $X^1$ to $X^3$, a divalent group of the substituted or unsubstituted aromatic group represented by $A^1$ and $B^1$ to $B^3$ can be given.

Preferably, aromatic groups such as a substituted or unsubstituted phenylene group, a substituted or unsubstituted biphenylene group, a substituted or unsubstituted terphenylene group, a substituted or unsubstituted naphthylene group, a substituted or unsubstituted phenanthrenylene group, a substituted or unsubstituted anthracenylene group, a substituted or unsubstituted chrysenylene group, a substituted or unsubstituted fluorenylene group and a substituted or unsubstituted triphenylenylene group can be given.

As the substituted or unsubstituted heterocyclic group represented by $X^1$ to $X^3$, a divalent group of the substituted or unsubstituted heterocyclic group represented by $A^1$ and $B^1$ to $B^3$ can be given.

A substituted or unsubstituted dibenzofuranylene group, a substituted or unsubstituted pyridinylene group and a substituted or unsubstituted carbazolylene group are preferable.

The substituent for the substituted or unsubstituted aromatic group represented by $A^1$, $X^1$ to $X^3$ and $B^1$ to $B^3$ and the substituent for the substituted or unsubstituted heterocyclic group represented by $X^1$ to $X^3$ and $B^1$ to $B^3$ (hereinafter often simply referred to as the substituent for the aromatic group or the heterocyclic group) can be appropriately selected by a person skilled in the art. For example, an alkyl group, an aromatic group, a fluorine atom, an alkoxy group, a substituted or unsubstituted silyl group, a cyano group and a cycloalkyl group can be given.

The alkyl group and the aromatic group as the substituent of the aromatic group or the heterocyclic group are the same as the alkyl group and the aromatic group represented by $A^1$.

The alkoxy group as the substituent of the aromatic group or the heterocylic group is a group which is represented by —OY, for example. Y is selected from the alkyl groups represented by $A^1$. The alkoxy group is a methoxy group or an ethoxy group, for example.

As the substituted or unsubstituted silyl group as the substituent of the aromatic group or the heterocyclic group, a trimethylsilyl group, a triethylsilyl group, a t-butyldimethylsilyl group, a vinyldimethylsilyl group, a propyldimethylsilyl group, a trimethylphenylsilyl group, a triisopropylsilyl group or the like can be given.

As the cycloalklyl group as the substituent of the aromatic group or the heterocyclic group, a cycloalkyl group having 3 to 10 (preferably 3 to 8, more preferably 3 to 6) ring atoms can be given. For example, a cyclopropyl group, a cyclobutyl group, a cyclopentyl group, a cyclohexyl group, a cycloheptyl group or the like can be given.

The substituent for the aromatic group or the heterocyclic group is preferably an alkyl group, an aromatic group or a substituted or unsubstituted silyl group. The substituent for the aromatic group or the heterocyclic group is particularly preferably a substituted or unsubstituted silyl group (an alkylsilyl group, for example).

The aromatic amine derivative of the invention is preferably an aromatic amine derivative represented by the following formula (3):

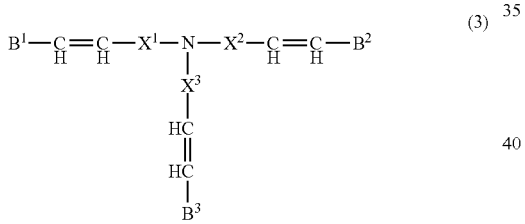

(3)

wherein $X^1$, $X^2$, $X^3$, $B^1$, $B^2$ and $B^3$ are the same as those defined in the formula (1).

In the aromatic amine derivative of the invention represented by the above formulas (1) and (3), it is preferred that one of $X^1$ and $X^2$ be a substituted or unsubstituted fused aromatic ring group having 10 to 30 ring carbon atoms or a substituted or unsubstituted fused heterocyclic group having 10 to 30 ring atoms, and the other of $X^1$ and $X^2$ be a substituted or unsubstituted non-fused aromatic ring group having 6 to 30 ring carbon atoms or a substituted or unsubstituted non-fused heterocyclic group having 6 to 30 ring atoms.

The above-mentioned substituted or unsubstituted fused aromatic ring group having 10 to 30 ring carbon atoms or the substituted or unsubstituted fused heterocyclic group having 10 to 30 ring atoms is preferably a substituted or unsubstituted fused aromatic group having 10 to 20 ring carbon atoms or a substituted or unsubstituted fused heterocyclic group having 10 to 20 ring atoms. More preferably, it is a substituted or unsubstituted fused aromatic ring group having 10 to 16 ring carbon atoms or a substituted or unsubstituted fused heterocyclic group having 10 to 16 ring atoms. A substituted or unsubstituted naphthylene group, a substituted or unsubstituted anthracenylene group, a substituted or unsubstituted phenanthrylene group, a substituted or unsubstituted chrysenylene group, a substituted or unsubstituted fluorenylene group or a substituted or unsubstituted dibenzofuranylene group are particularly preferable.

The substituted or unsubstituted non-fused aromatic ring group having 6 to 30 ring carbon atoms or the substituted or unsubstituted non-fused heterocyclic group having 6 to 30 ring atoms as mentioned above is preferably a substituted or unsubstituted non-fused aromatic ring group having 6 to 20 ring carbon atoms or a substituted or unsubstituted non-fused heterocyclic group having 6 to 20 ring atoms, more preferably a substituted or unsubstituted non-fused aromatic ring group having 6 to 12 ring carbon atoms or a substituted or unsubstituted non-fused heterocyclic group having 6 to 12 ring atoms. Specific examples thereof include a substituted or unsubstituted phenylene group, a substituted or unsubstituted biphenylene group, a substituted or unsubstituted terphenylene group and a substituted or unsubstituted pyridylene group. Of these, a substituted or unsubstituted phenylene group or a substituted or unsubstituted biphenylene group is particularly preferable.

The aromatic amine derivatives represented by the above formulas (1) and (3) are preferably aromatic amine derivatives represented by the formula (4) or (5), given later.

The aromatic amine derivative represented by the formula (4) is an aromatic amine represented by the formula (3) in which $X^1$ is a fluorenylene group.

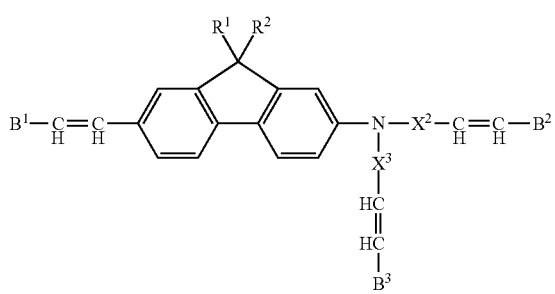

(4)

wherein $X^2$, $X^3$, $B^1$, $B^2$ and $B^3$ are the same as those defined in the formula (1);

$R^1$ and $R^2$ are independently an alkyl group, an aromatic group, a fluorine atom, an alkoxy group or a substituted or unsubstituted silyl group; and $R^1$ and $R^2$ may be combined with each other to form a saturated or unsaturated ring.

The alkyl group, the aromatic group, the alkoxy group and the substituted or unsubstituted silyl group represented by $R^1$ and $R^2$ in the formula (4) are the same as the substituent of the aromatic group or the heterocyclic group as mentioned above.

The aromatic amine derivative represented by the formula (5) is an aromatic amine derivative represented by the formula (3) in which $X^1$ is an unsubstituted naphthylene group.

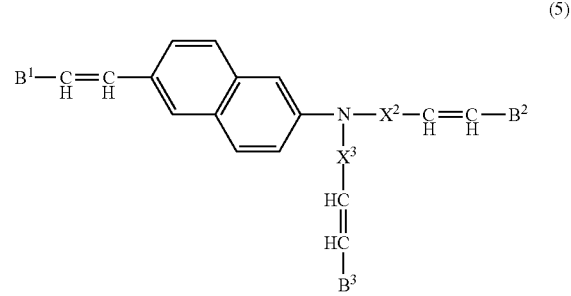

(5)

wherein $X^2$, $X^3$, $B^1$, $B^2$ and $B^3$ are the same as those defined in the formula (1).

In the aromatic amine derivative represented by the formulas (1), (3) to (5), it is preferred that $X^2$ and $X^3$ be both substituted or unsubstituted phenylene groups.

In the aromatic amine derivative represented by the formulas (1), (3) to (5), it is preferred that $X^3$ be a substituted or unsubstituted fluorenylene group.

In the aromatic amine derivative represented by the formulas (1), (3) to (5), it is preferred that any of the aromatic group or the heterocyclic group represented by $B^1$, $B^2$ and $B^3$ has a substituted or unsubstituted silyl group as a substituent.

Specific examples of the aromatic amine derivative of the invention are given below.

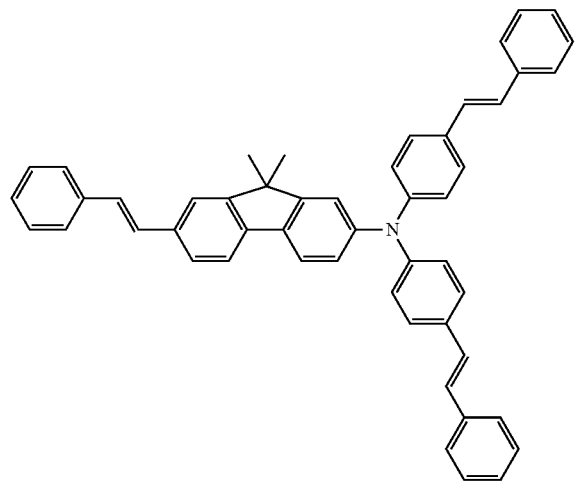

D-1

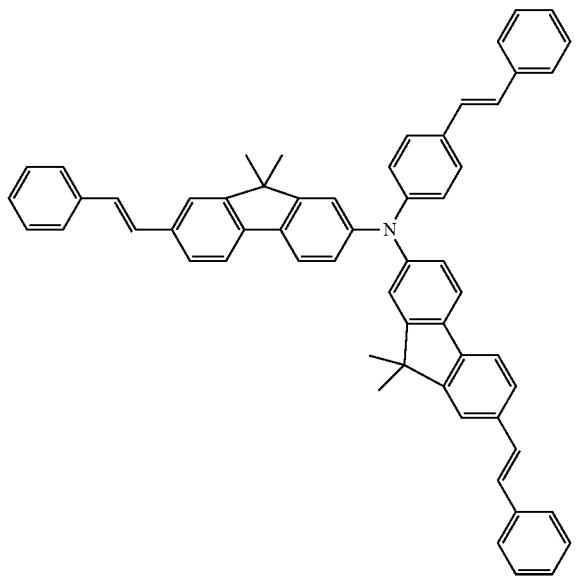

D-2

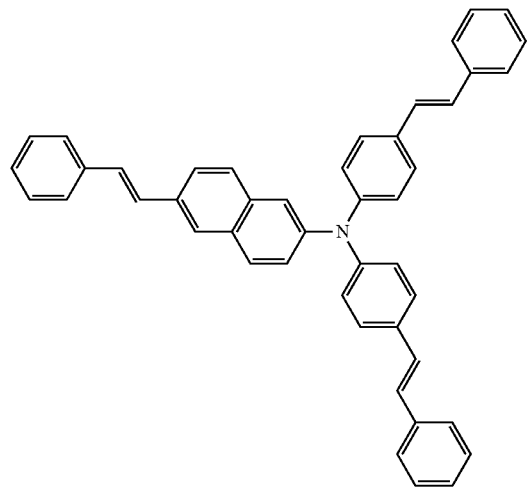

D-3

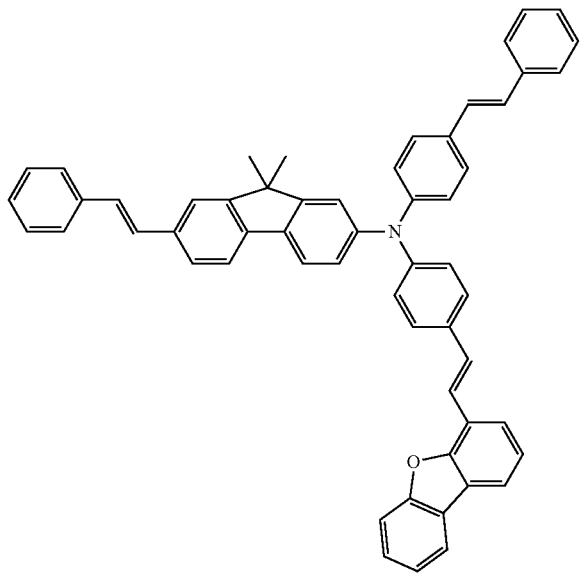

D-4

-continued
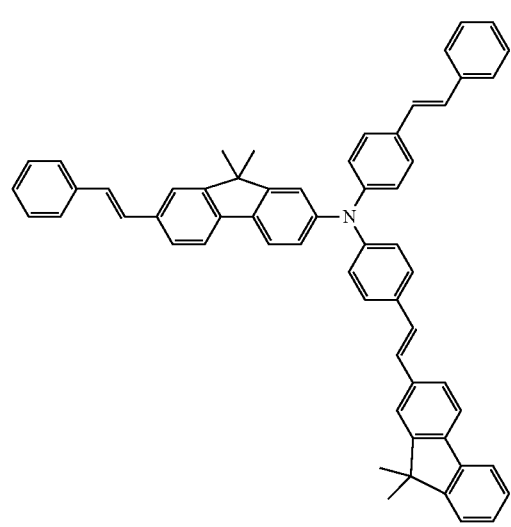
D-5
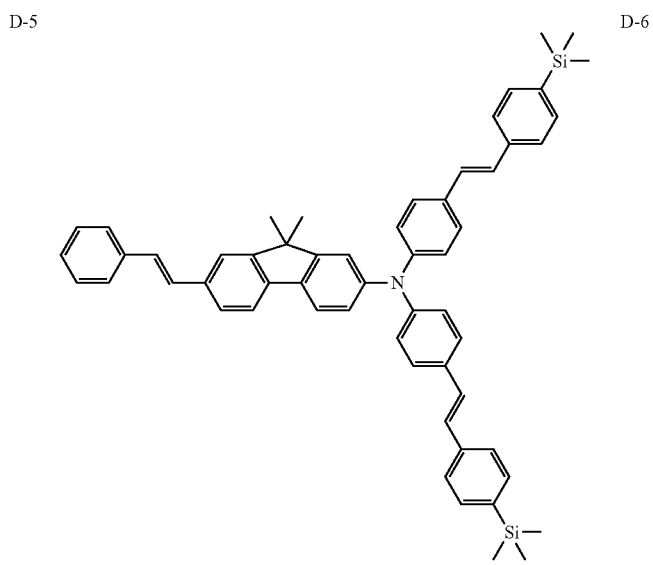
D-6
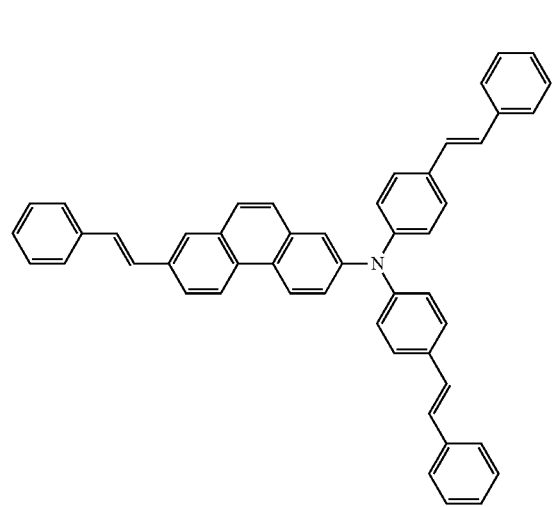
D-7
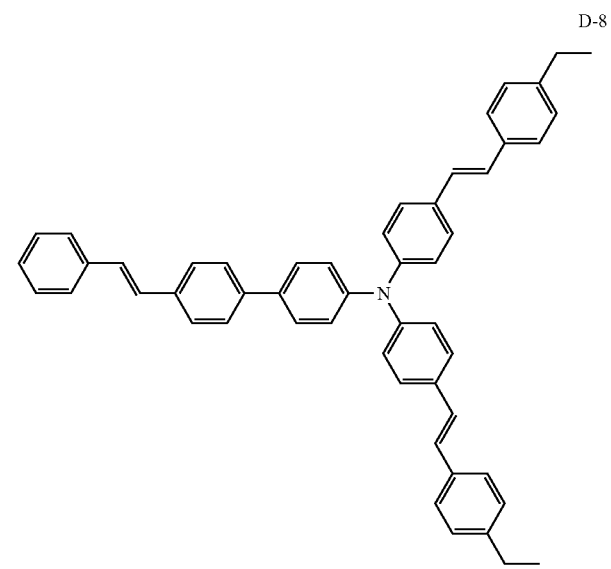
D-8

-continued
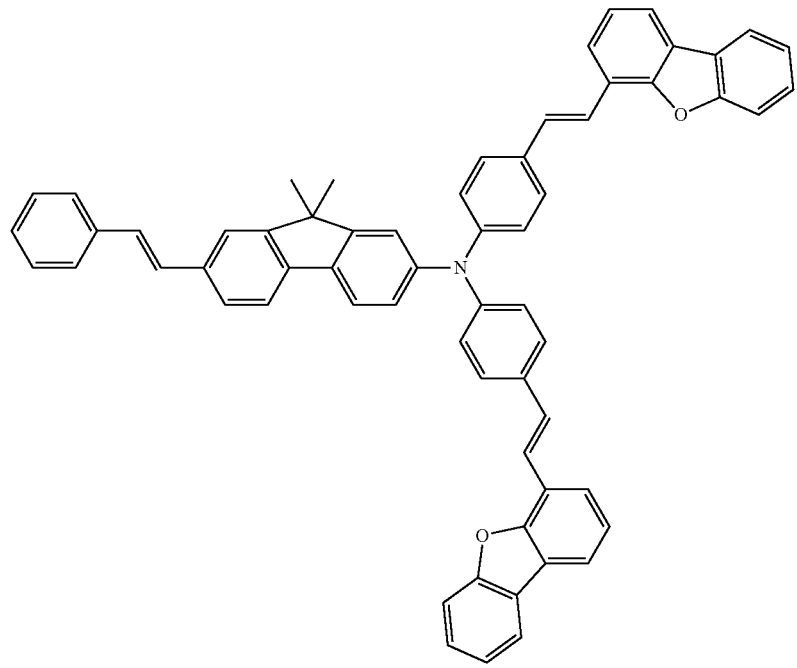
D-9
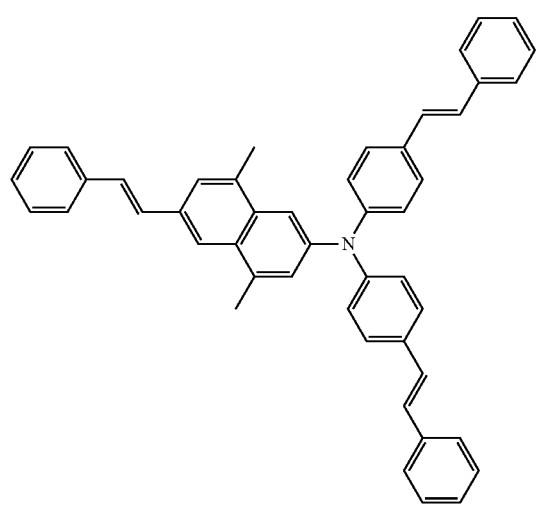
D-10
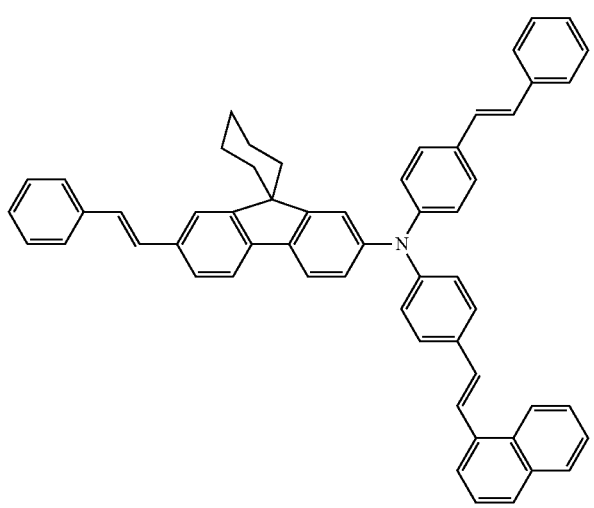
D-11
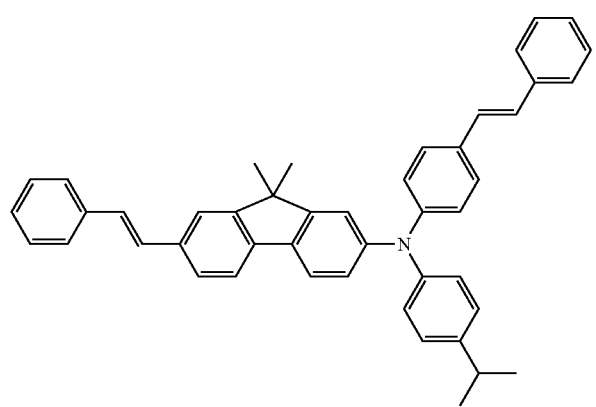
D-12
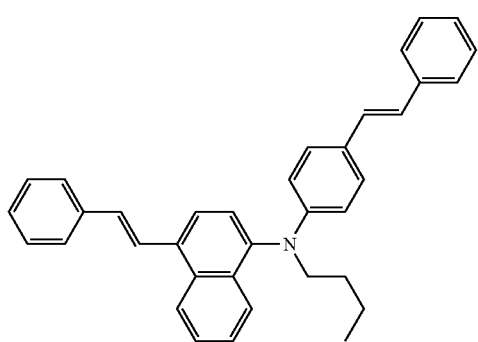
D-13

-continued
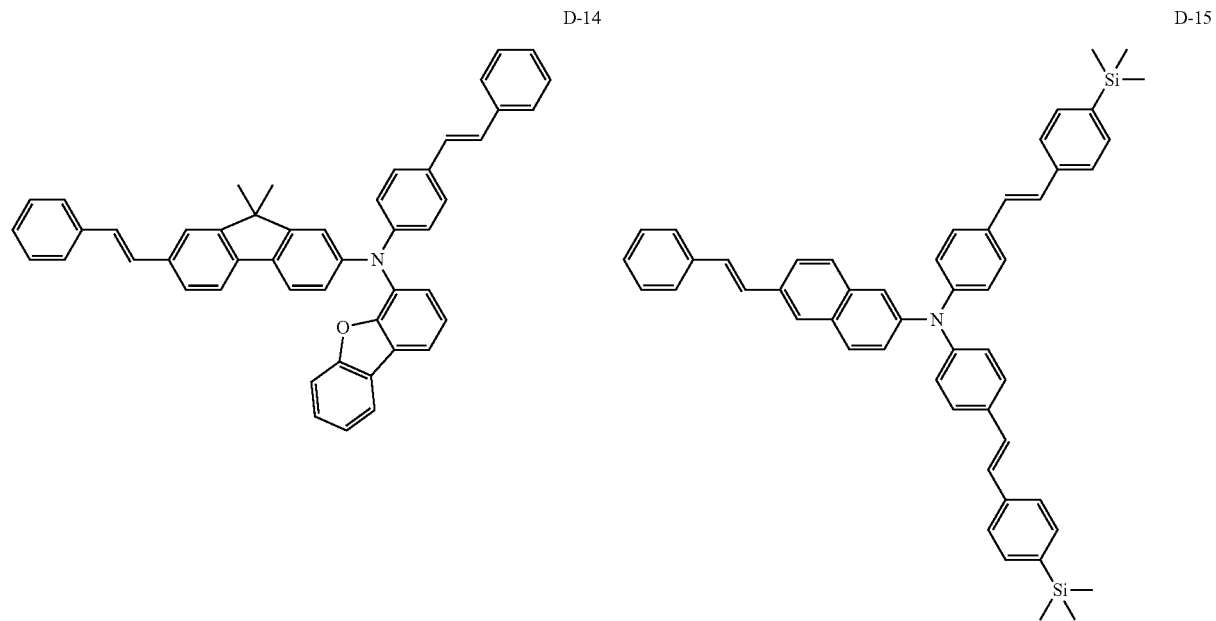
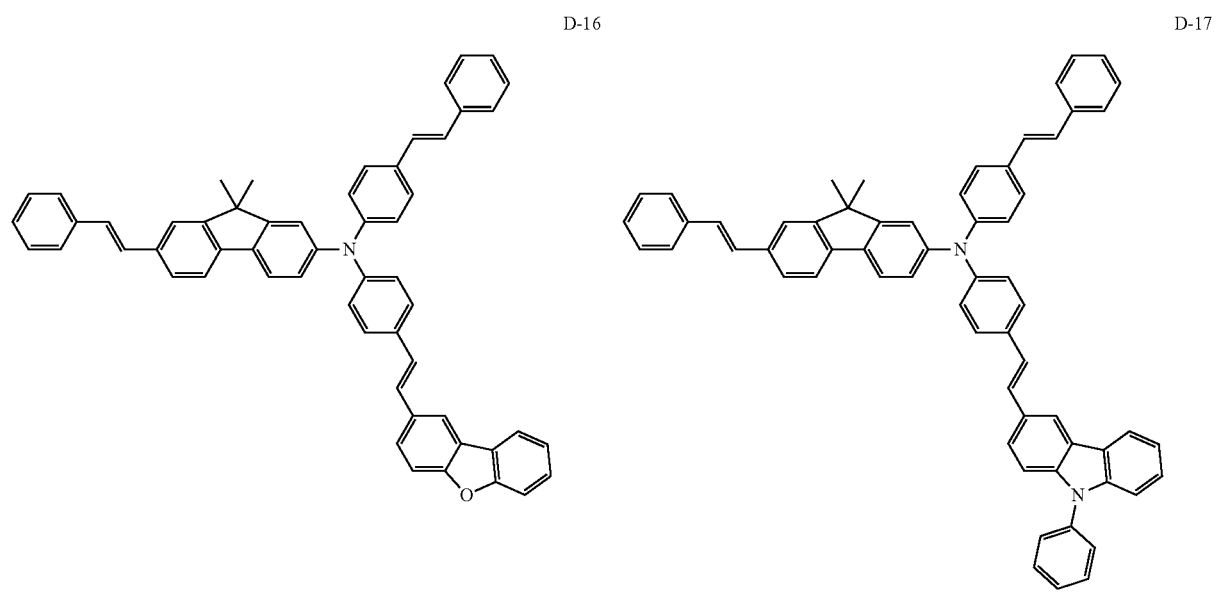

-continued
D-18
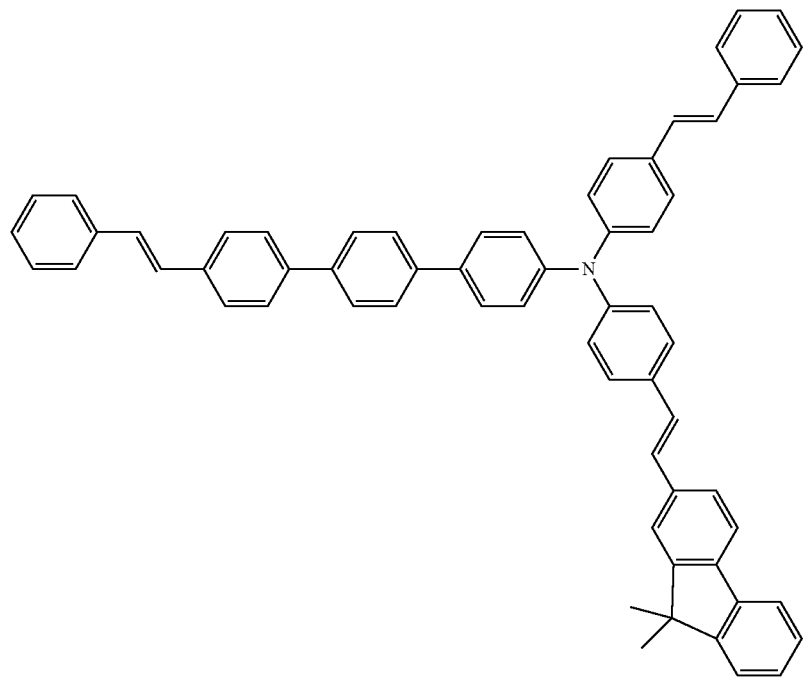
D-19
D-20
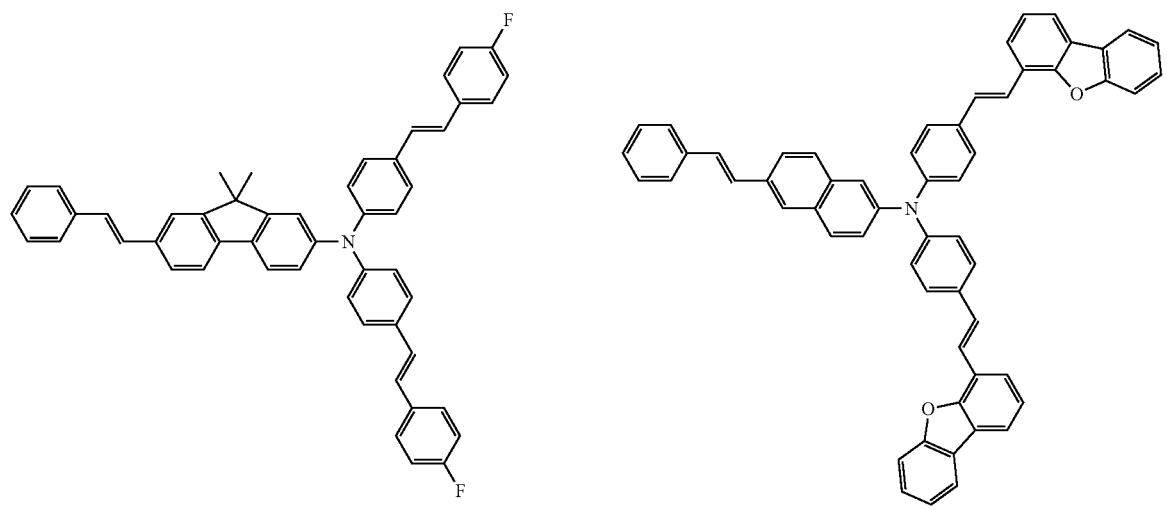
D-21
D-22
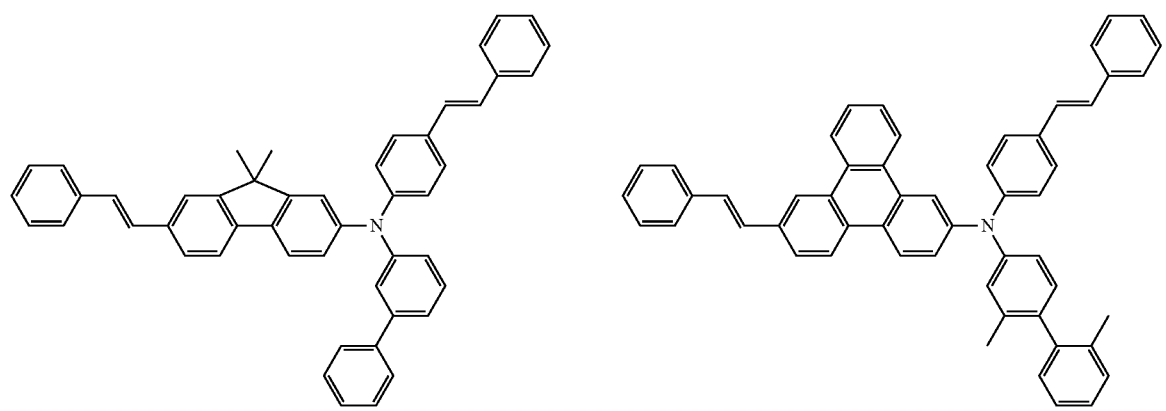

-continued
D-23
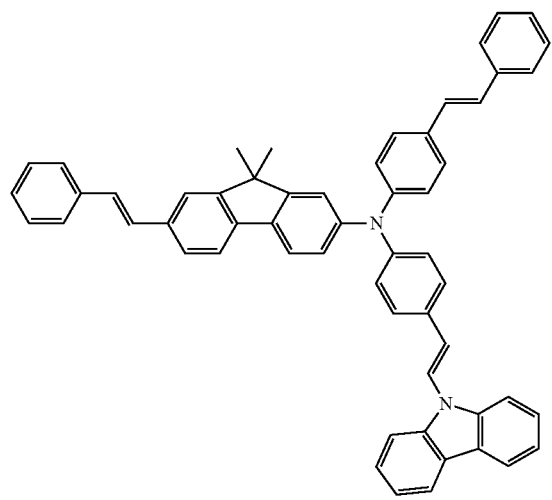
D-24
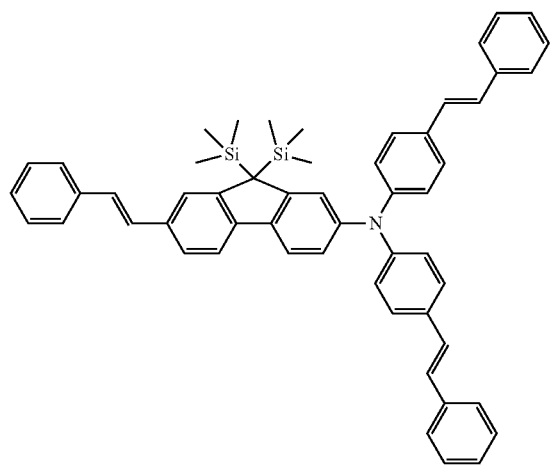
D-25
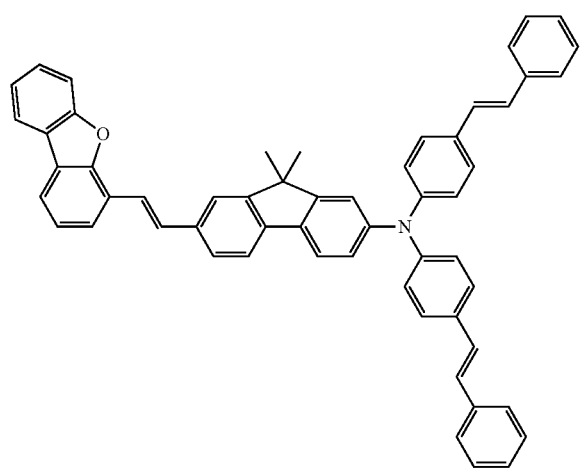
D-26
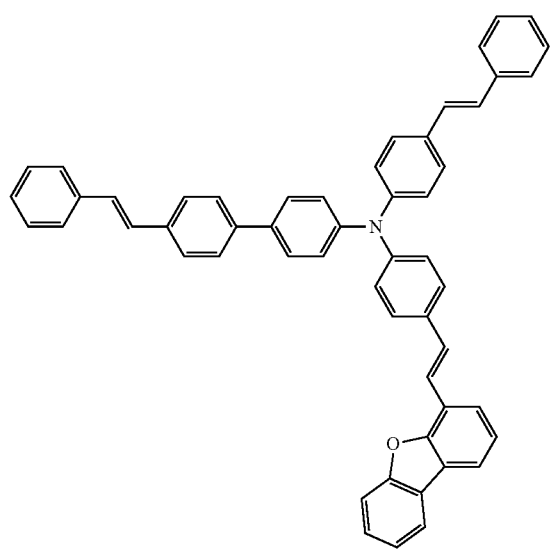
D-27
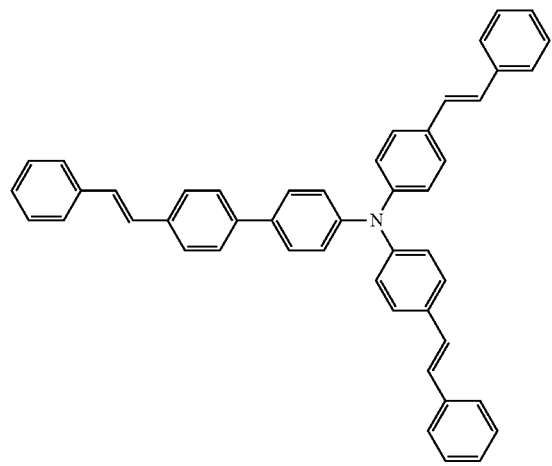
D-28
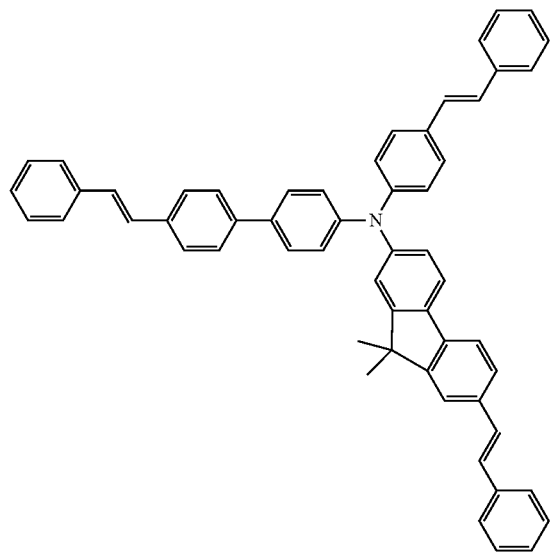

-continued
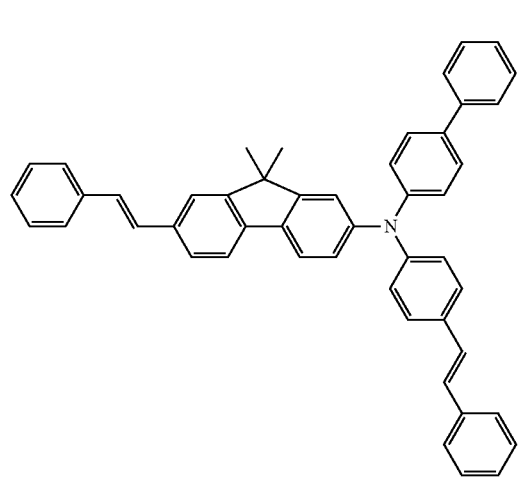
D-29
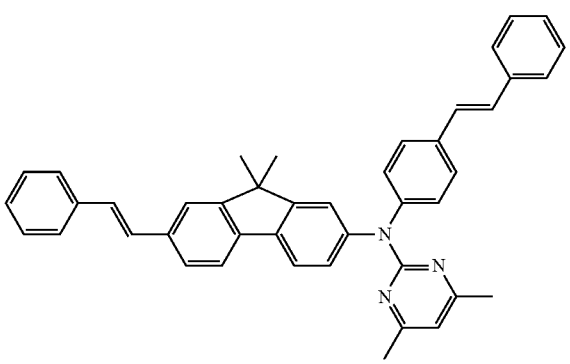
D-30
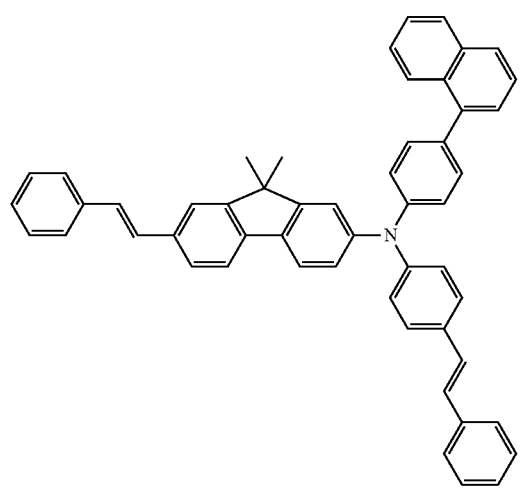
D-31
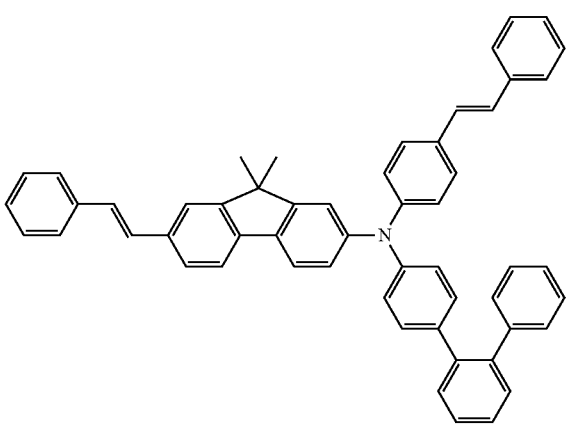
D-32
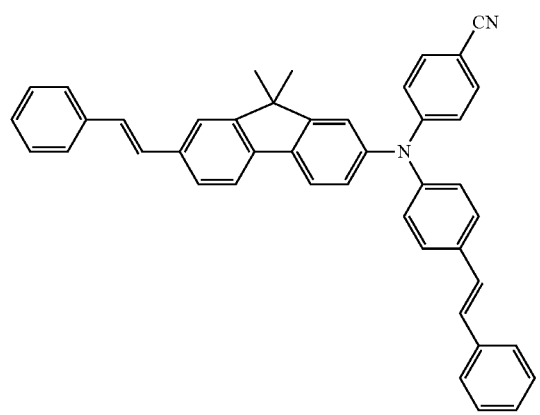
D-33
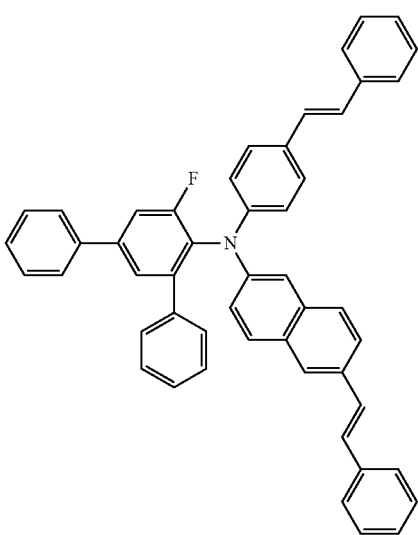
D-34

-continued
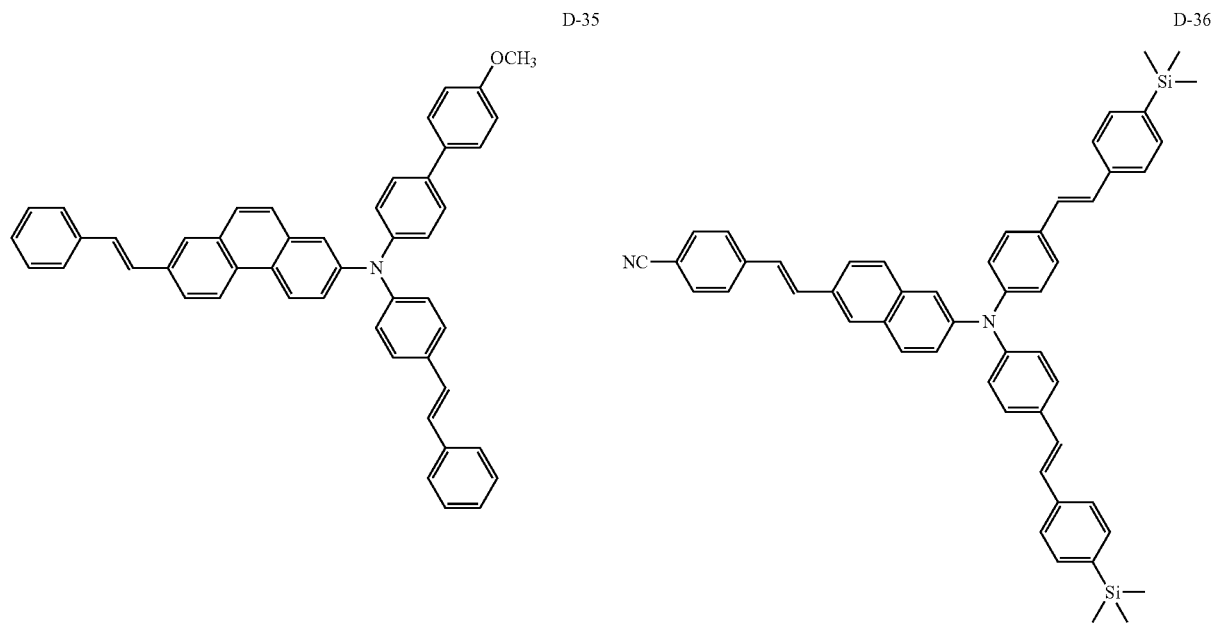
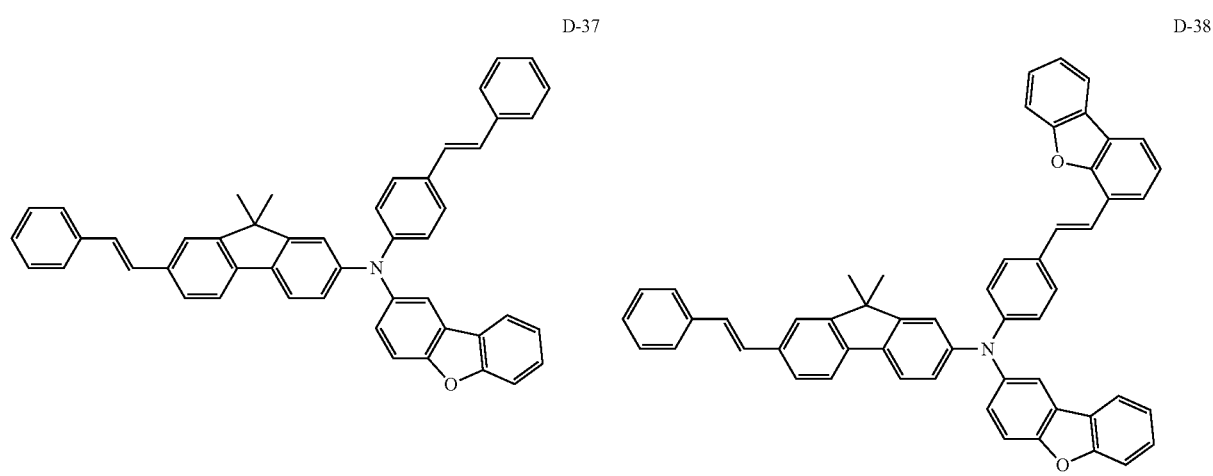

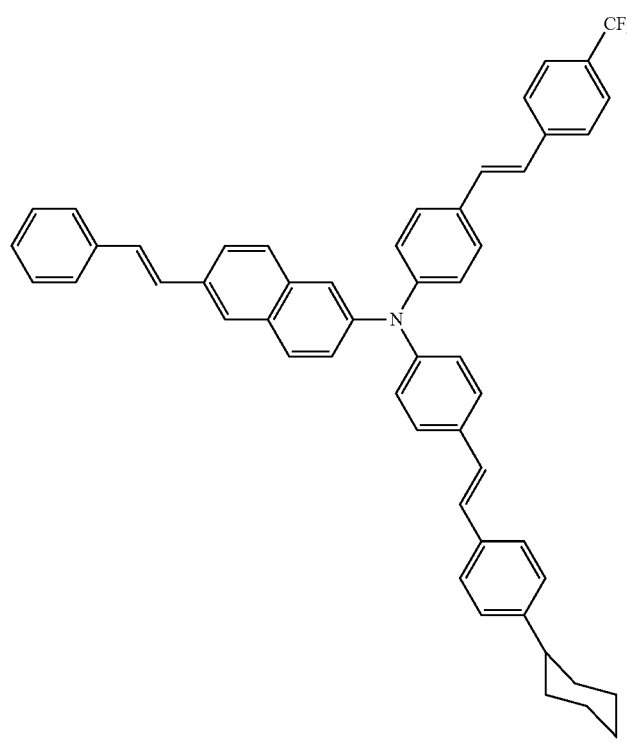

D-39

The method for producing the aromatic amine derivative of the invention is not particularly restricted. The aromatic amine derivative of the invention can be produced by a known method. For example, it can be produced by a coupling reaction between an amine derivative and an aromatic halogenated compound by using a copper catalyst stated in Tetrahedron (1984), 40, 1435-1456 or a palladium catalyst stated in Journal of the American Chemical Society 123 (2001) 7727 to 7729.

It is preferred that the aromatic amine derivative of the invention be used as a material for an organic EL device. The aromatic amine derivative of the invention is preferably used as an emitting material or a hole-transporting material for an organic EL device, with the use as a doping material being particularly preferable.

The organic EL device of the invention comprises between an anode and a cathode one or more organic thin film layers comprising an emitting layer, wherein at least one layer of the organic thin film layers comprises at least one kind of the aromatic amine derivative according to the invention.

In the organic EL device of the invention, it is preferred that the emitting layer contain at least one kind of the aromatic amine derivative of the invention. It is preferred that the emitting layer contain 0.01 to 20 wt %, further preferably 0.5 to 20 wt %, particularly preferably 0.5 to 15 wt %, and most preferably 0.5 to 10 wt %, of the aromatic amine derivative of the invention.

In the organic EL device of the invention, it is preferred that the hole-transporting layer contain at least one kind of the aromatic amine derivative of the invention. It is preferred that the hole-transporting layer contain 50 to 100 wt %, further preferably 80 to 100 wt %, of the aromatic amine derivative of the invention.

When the aromatic amine derivative of the invention is used as the emitting material of the organic EL device, it is preferred that the emitting layer contain at least one kind of the aromatic amine derivative and at least one kind of an anthracene derivative represented by the following formula (2A), since an organic EL device which has a high luminous efficiency, is hardly deteriorated even if used for a long period of time, and hence has a prolonged lifetime can be provided.

Hereinbelow, an anthracene derivative represented by the following formula (2A) will be explained.

(Anthracene Derivative)

The anthracene derivative represented by the following formula (2A) is the following compound.

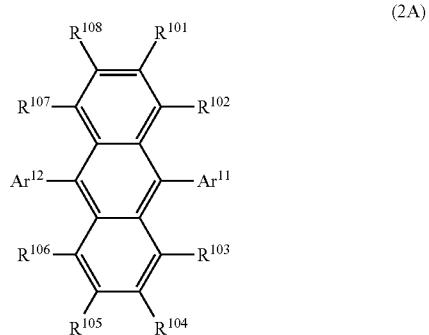

(2A)

In the formula (2A), $Ar^{11}$ and $Ar^{12}$ are independently a substituted or unsubstituted monocyclic group having 5 to 50 ring atoms or a substituted or unsubstituted fused ring group having 8 to 50 ring atoms; and $R^{101}$ to $R^{108}$ are independently a hydrogen atom, a substituted or unsubstituted monocyclic group having 5 to 50 ring atoms, a substituted or unsubstituted fused ring group having 8 to 50 ring atoms, a group formed by combination of a monocyclic group and a fused ring group, a substituted or unsubstituted alkyl group having 1 to 50 carbon atoms, a substituted or unsubstituted cycloalkyl group having 3 to 50 ring carbon atoms, a substituted or unsubstituted alkoxy group having 1 to 50 carbon atoms, a substituted or unsubstituted aralkyl group having 7 to 50 carbon atoms, a substituted or unsubstituted aryloxy group having 6 to 50 ring carbon atoms, a substituted or unsubstituted silyl group, a halogen atom and a cyano group.

The monocyclic group in the formula (2A) is a group composed of a ring having no fused structure.

As the specific examples of the monocyclic group having 5 to 50 ring atoms (preferably 5 to 30 ring atoms, more preferably 5 to 20 ring atoms), an aromatic group such as a phenyl group, a biphenyl group, a terphenyl group and a quarterphenyl group and a heterocyclic group such as a pyridyl group, a pyrazyl group, a pyrimidyl group, a triazinyl group, a furyl group and a thienyl group are preferable.

Of these, a phenyl group, a biphenyl group and a terphenyl group are preferable.

The fused ring group in the formula (2A) is a group obtained by the fusion of two or more rings.

As the specific examples of the fused ring group having 8 to 50 (preferably 8 to 30, more preferably 8 to 20) ring atoms, a fused aromatic ring group such as a naphthyl group, a phenanthryl group, an anthryl group, a chrysenyl group, a benzoanthryl group, a benzophenanthryl group, a triphenylenyl group, a benzochrysenyl group, an indenyl group, a fluorenyl group, a benzofluorenyl group, a dibenzofluorenyl group, a fluoranthenyl group and a benzofluoranthenyl group or a fused heterocyclic group such as a benzofuranyl group, a benzothiophenyl group, an indolyl group, a dibenzofuranyl group, a dibenzothiophenyl group, a carbazolyl group, a quinolyl group, a phenanthrolinyl group are preferable.

Of these, a naphthyl group, a phenanthryl group, an anthryl group, a fluorenyl group, a fluoranthenyl group, a benzanthryl group, a dibenzothiophenyl group, a dibenzofuranyl group and a carbazolyl group are preferable.

The specific examples of the alkyl group in the formula (2A) are the same as the specific examples of the alkyl group represented by $A^1$.

The specific examples of the cycloalkyl group, the alkoxy group and the silyl group in the formula (2A) are the same as the specific examples of the substituent of the aromatic group or the heterocyclic group represented by $A^1$.

The specific examples of the aralkyl group, the aryloxy group and the halogen atom in the formula (2A) will be given below.

As for the "substituted or unsubstituted" in $Ar^{11}$, $Ar^{12}$, $R^{101}$ to $R^{108}$, preferable substituents include a monocyclic group, a fused ring group, an alkyl group, a cycloalkyl group, a silyl group, an alkoxy group, a cyano group and fluorine. Of these, a monocyclic group and a fused ring group are particularly preferable. Preferable specific substituents are the same as the groups in the formula (2A) and the substituents of the aromatic group or the heterocyclic group represented by $A^1$.

It is preferred that the anthracene derivative represented by the formula (2A) be one of the following anthracene derivatives (A), (B) and (C), and preferable anthracene derivatives are selected according to the constitution or required properties of the organic EL device to which the anthracene derivative is applied.

(Anthracene Derivative (A))

In this anthracene derivative, $Ar^{11}$ and $Ar^{12}$ in the formula (2A) are independently a substituted or unsubstituted fused ring group having 8 to 50 ring atoms. The anthracene derivative can be divided into those in which $Ar^{11}$ and $Ar^{12}$ are the same substituted or unsubstituted fused ring groups, and those in which $Ar^{11}$ and $Ar^{12}$ are different substituted or unsubstituted fused ring groups.

An anthracene derivative in which $Ar^{11}$ and $Ar^{12}$ in the formula (2A) are different (including a difference in substitution position), which is a substituted or unsubstituted fused ring group, is particularly preferable. Preferable specific examples of the fused ring are as mentioned above. Of these, a naphthyl group, a phenanthryl group, a benzanthryl group, a fluorenyl group and a dibenzofuranyl group are preferable.

(Anthracene Derivative (B))

In this anthracene derivative, one of $Ar^{11}$ and $Ar^{12}$ in the formula (2A) is a substituted or unsubstituted monocyclic group having 5 to 50 ring atoms and the other is a substituted or unsubstituted fused ring group having 8 to 50 ring atoms.

In a preferred mode, $Ar^{12}$ is a naphthyl group, a phenanthryl group, a benzoanthryl group, a fluorenyl group and a dibenzofuranyl group, and $Ar^{11}$ is an unsubstituted phenyl group or a phenyl group which is substituted by a monocyclic group or a fused ring group.

Specific examples of preferable monocyclic groups and fused ring groups are as mentioned above.

In another preferred mode, $Ar^{12}$ is a fused ring group and $Ar^{11}$ is an unsubstituted phenyl group. In this case, as the fused ring group, a phenanthryl group, a fluorenyl group, a dibenzofuranyl group and a benzanthryl group are particularly preferable.

(Anthracene Derivative (C))

In this anthracene derivative, $Ar^{11}$ and $Ar^{12}$ in the formula (2A) are independently a substituted or unsubstituted monocyclic group having 5 to 50 ring atoms.

In a preferred mode, both $Ar^{11}$ and $Ar^{12}$ are substituted or unsubstituted phenyl groups.

In a further preferred mode, an anthracene derivative in which $Ar^{11}$ is an unsubstituted phenyl group and $Ar^{12}$ is a phenyl group having a monocyclic group or a fused ring group as the substituent, and an anthracene derivative in which $Ar^{11}$ and $Ar^{12}$ are independently a phenyl group having a monocyclic group or a fused ring group as a substituent.

Specific examples of preferable monocyclic groups and fused ring groups as the substituent are as mentioned above. As the monocyclic group as the substituent, a phenyl group and a biphenyl group are further preferable and as the fused ring group as the substituent, a naphthyl group, a phenanthryl group, a fluorenyl group, a dibenzofuranyl group and a benzoanthryl group are further preferable.

As the substituted or unsubstituted aralkyl group having 7 to 50 carbon atoms (the aryl part has 6 to 49 (preferably 6 to 30, more preferably 6 to 20, and particularly preferably 6 to 12) carbon atoms and the alkyl part has 1 to 44 (preferably 1 to 30, more preferably 1 to 20, further preferably 1 to 10 and particularly preferably 1 to 6) carbon atoms in the formula (2A), a benzyl group, a phenylethyl group, a 4-(2-phenylpropane-2-yl)phenyl group or the like can be given.

The aryloxy group having 6 to 50 ring carbon atoms in the formula (2A) is represented by —OY, and Y is selected from the monocyclic group or the fused ring group in the formula (2A). The aryloxy group is a phenoxy group, for example.

As the halogen atom in the formula (2A), fluorine, chlorine, bromine, iodine or the like can be given, with fluorine being preferable.

Specific examples of the anthracene derivatives represented by the formula (2A) are given below.

EM1
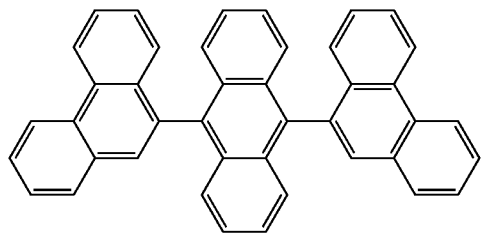
EM2
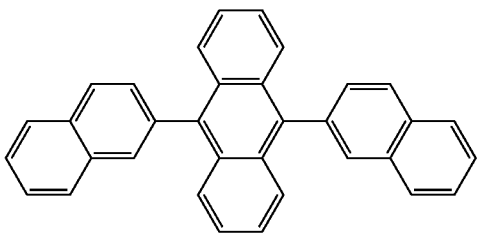
EM3
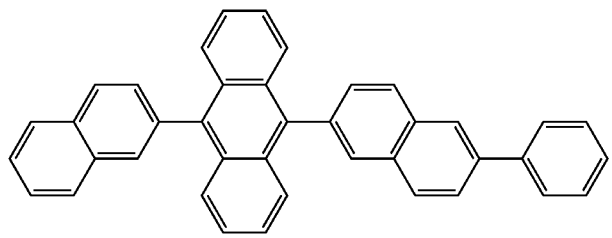
EM4
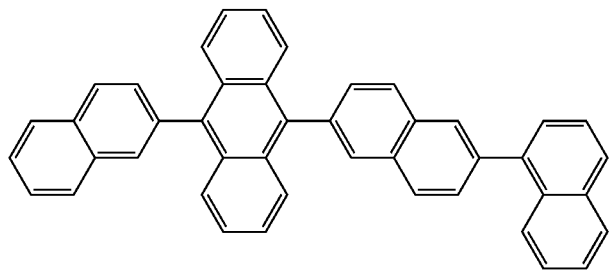
EM5
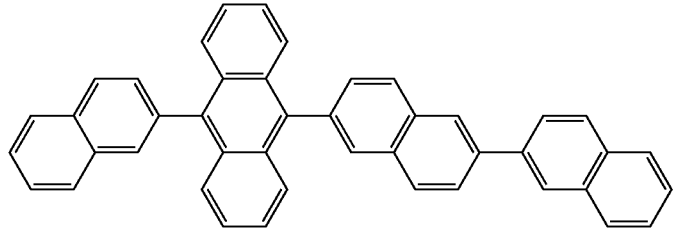
EM6
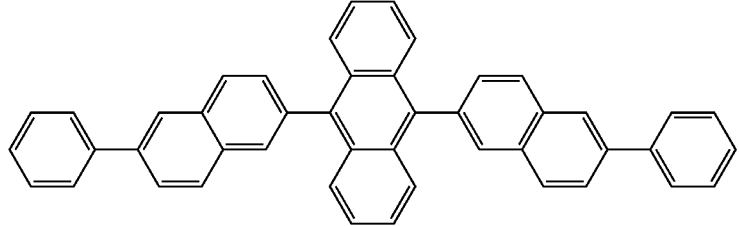
EM7
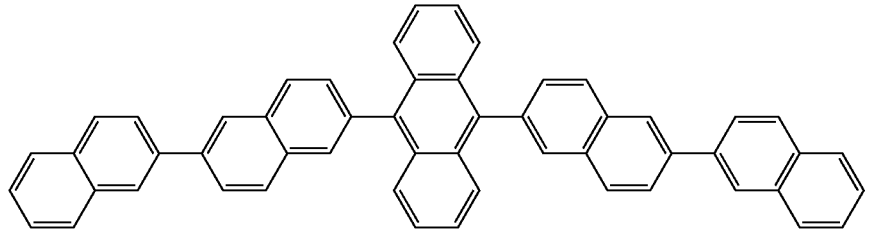

EM8
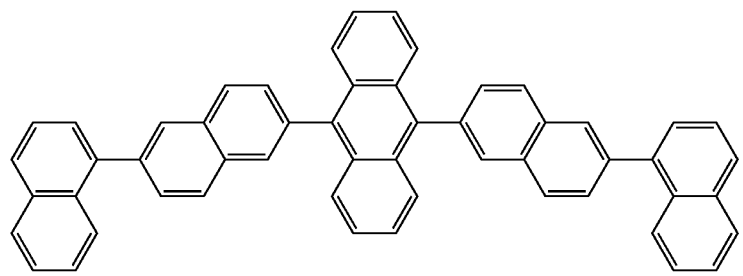
EM9
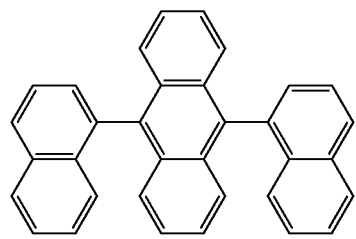
EM10
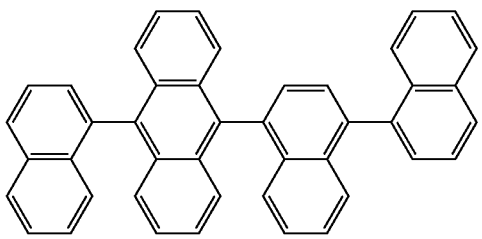
EM11
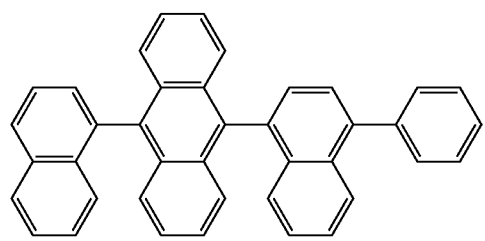
EM12
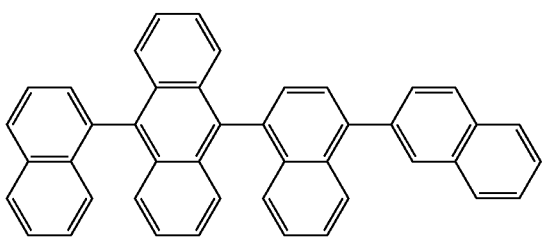
EM13
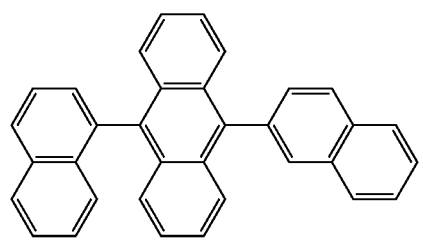
EM14
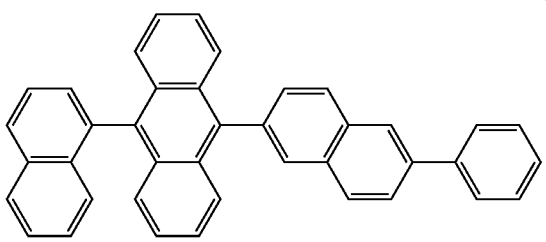
EM15
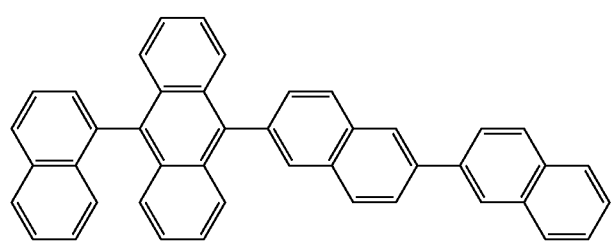
EM16
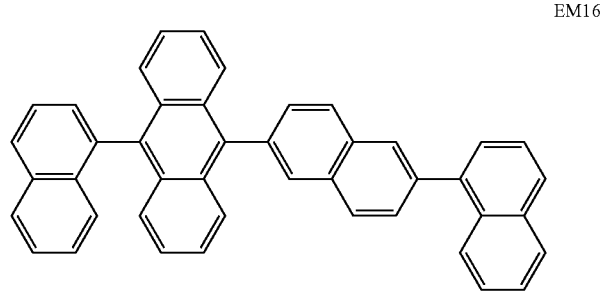
EM17
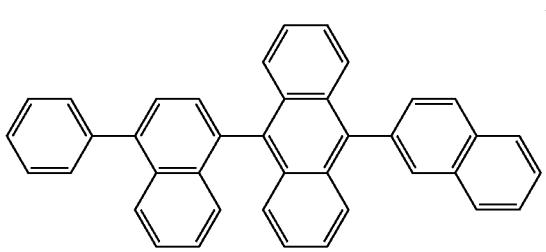

-continued
EM18
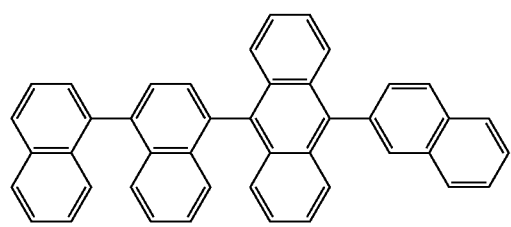
EM19
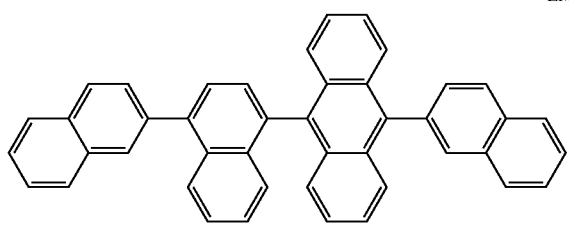
EM20
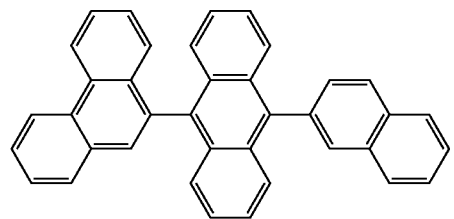
EM21
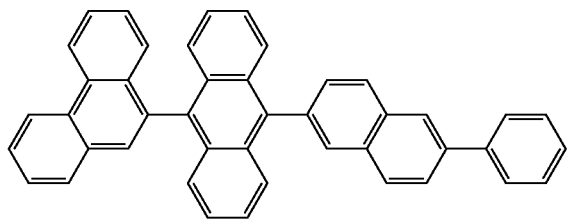
EM22
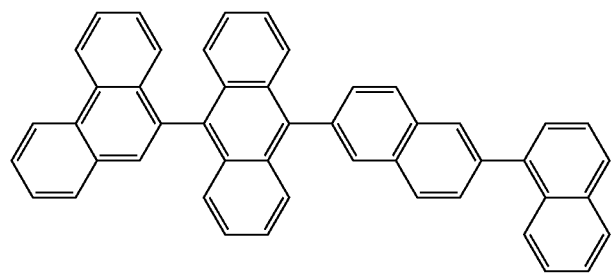
EM23
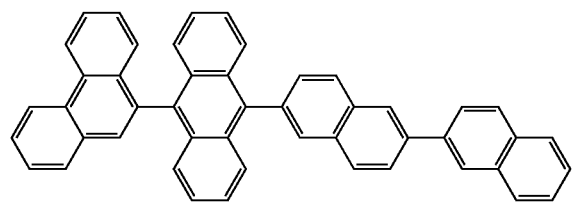
EM24
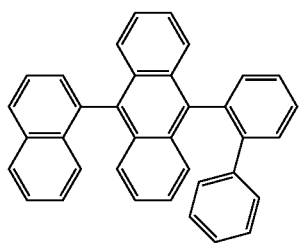
EM25
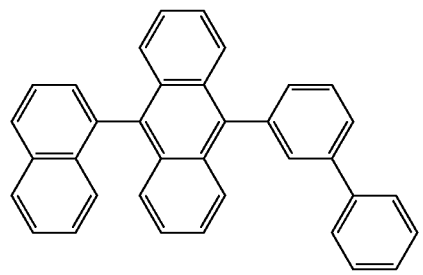
EM26
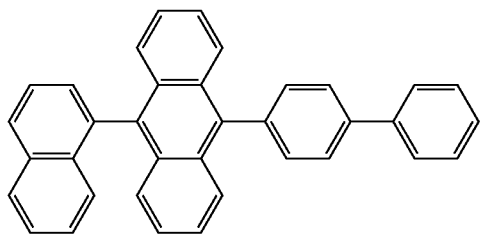
EM27
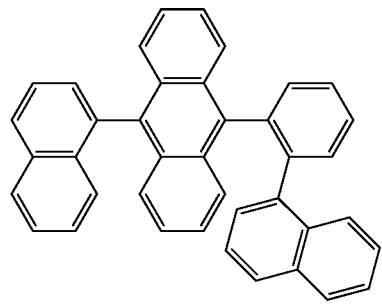
EM28
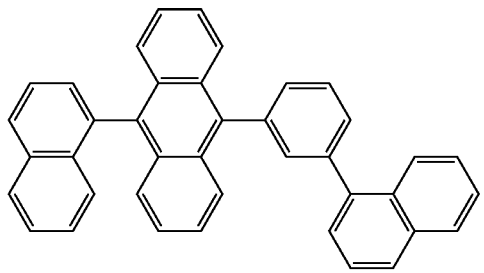

-continued
EM29
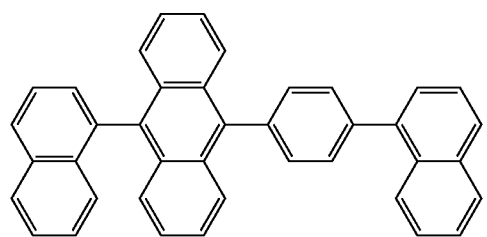
EM30
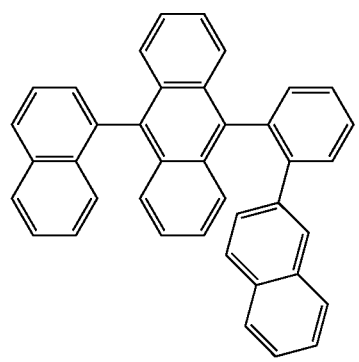
EM31
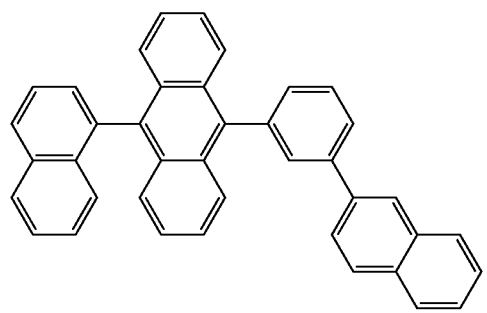
EM32
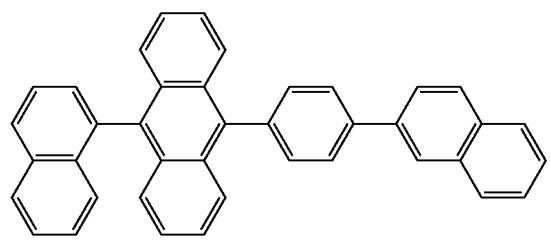
EM33
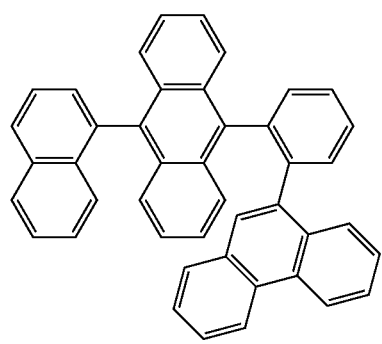
EM34
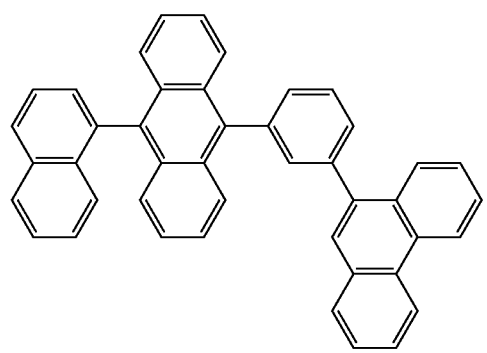
EM35
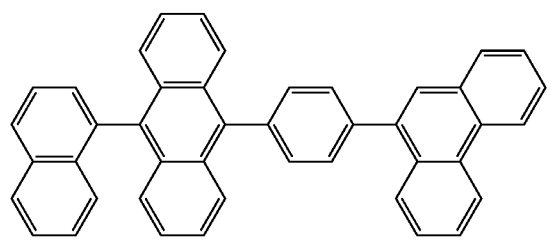
EM36
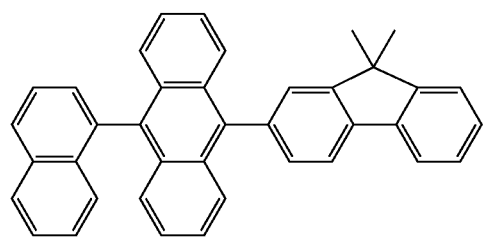
EM37
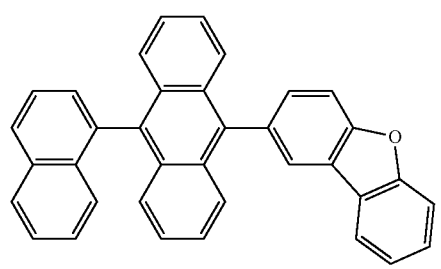
EM38
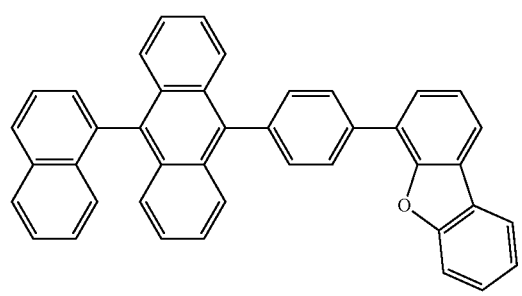

-continued
EM39
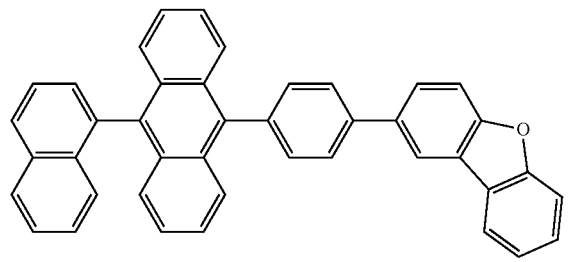
EM40
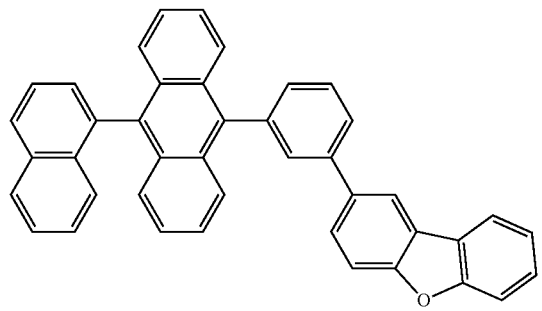
EM41
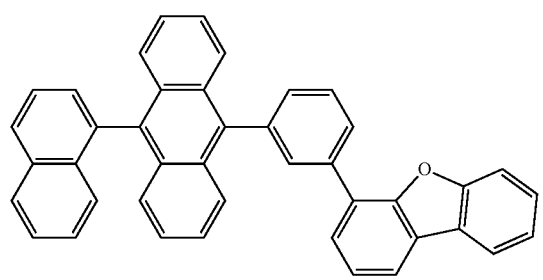
EM42
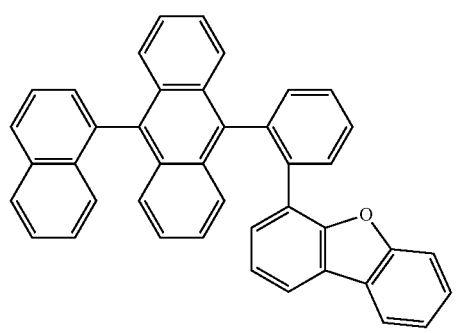
EM43
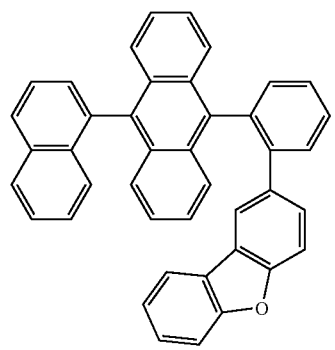
EM44
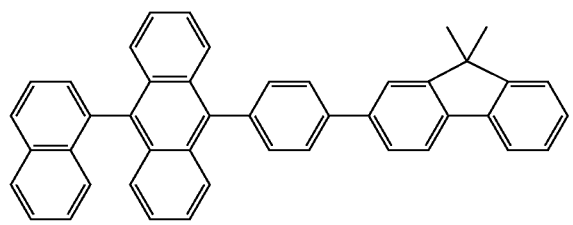
EM45
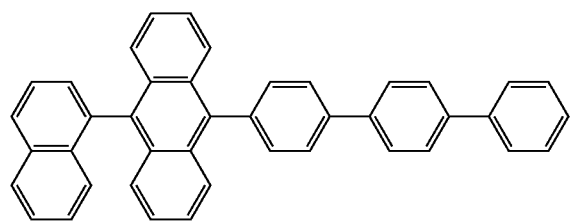
EM46
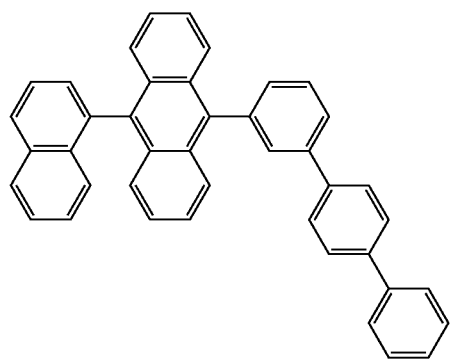

-continued
EM47
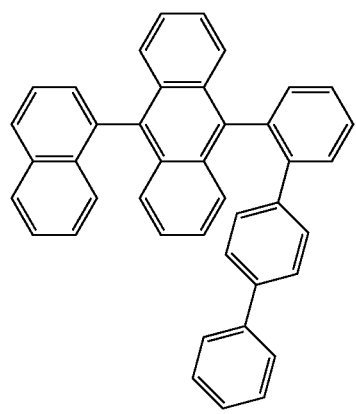
EM48
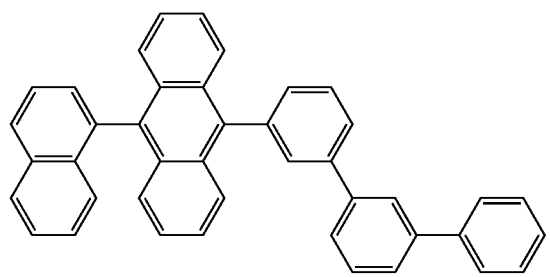
EM49
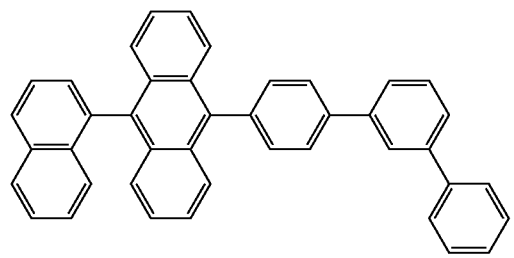
EM50
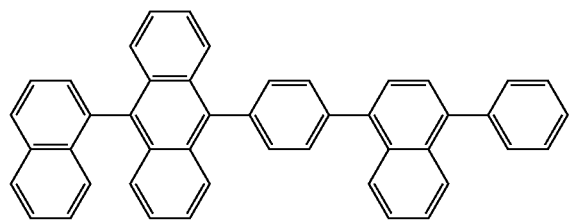
EM51
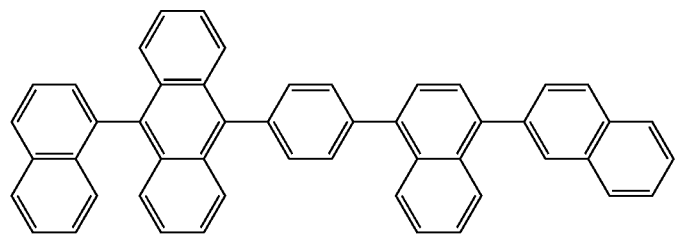
EM52
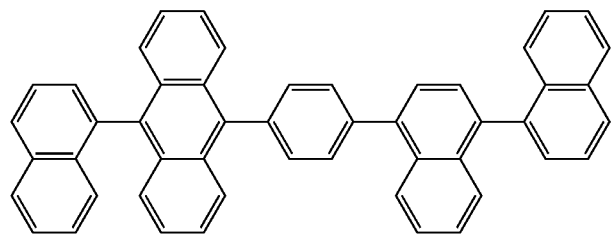
EM53
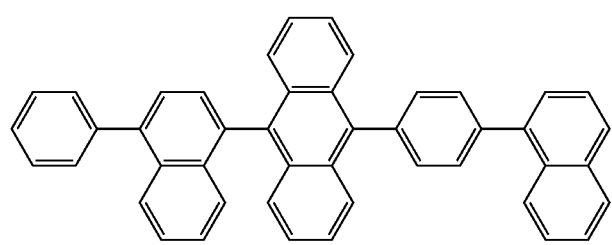

-continued
EM54
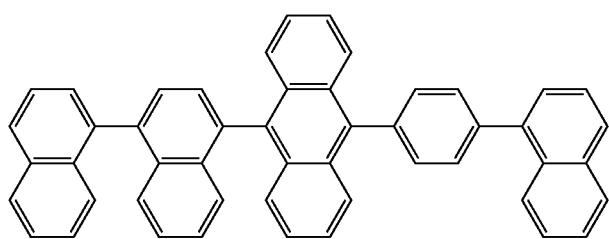
EM55
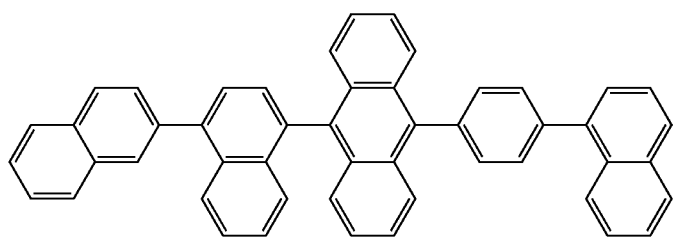
EM56
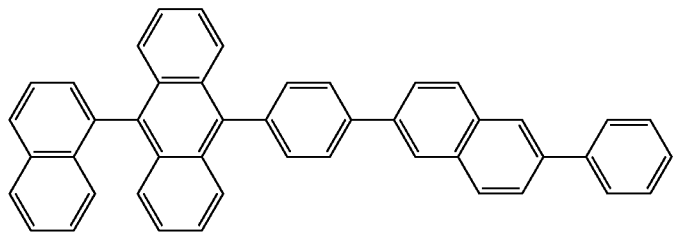
EM57
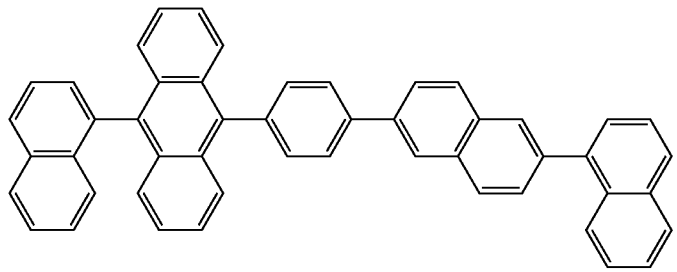
EM58
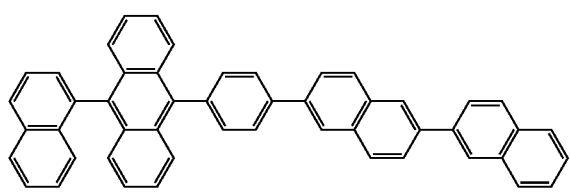
EM59
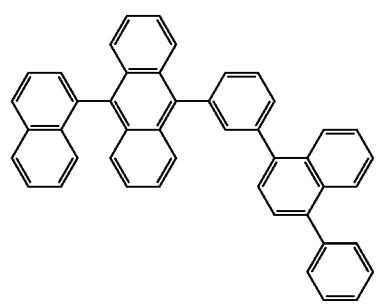

-continued
EM60
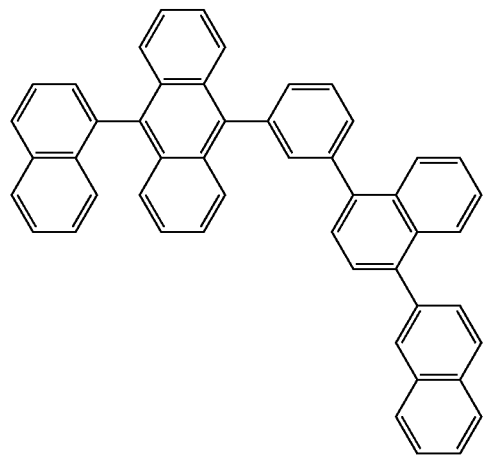
EM61
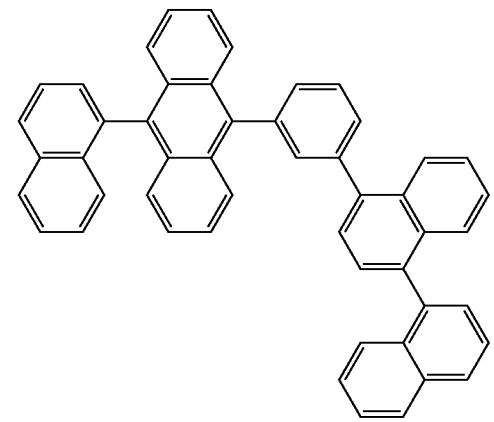
EM62
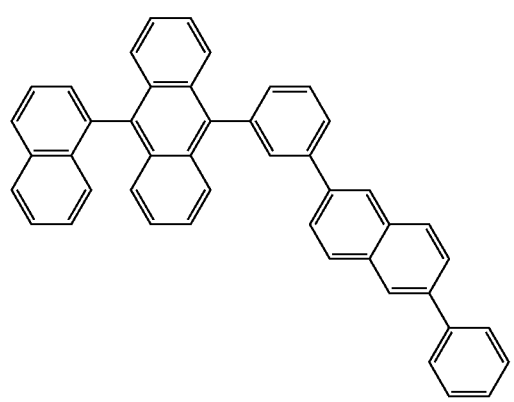
EM63
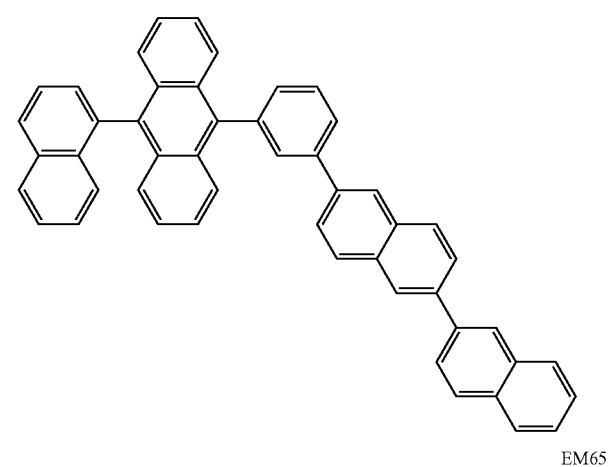
EM64
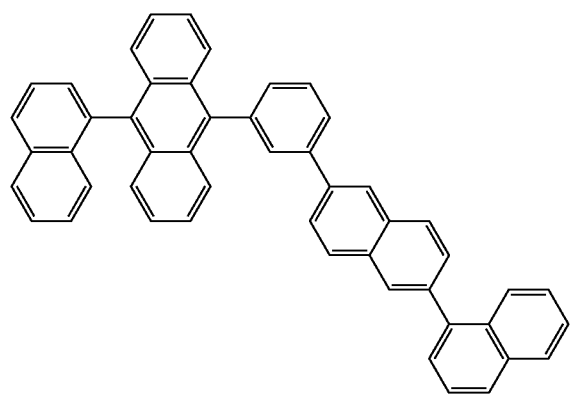
EM65
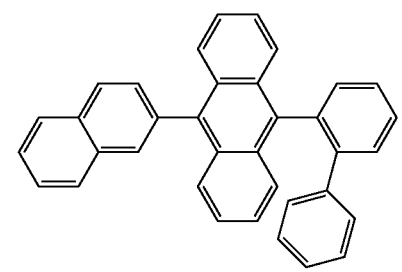
EM66
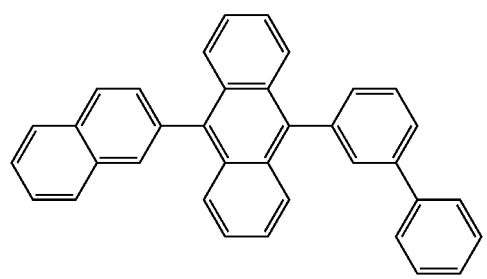
EM67
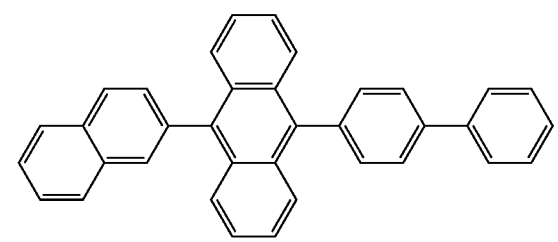

-continued
EM68
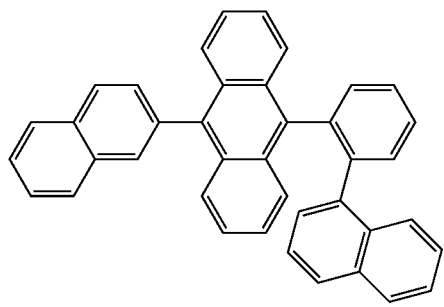
EM69
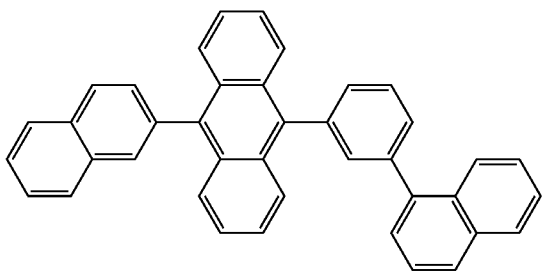
EM70
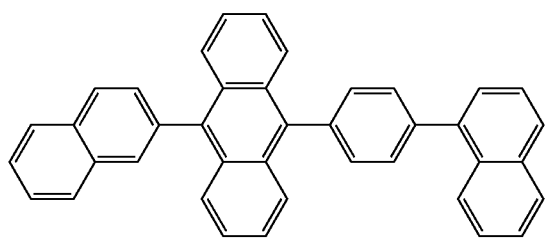
EM71
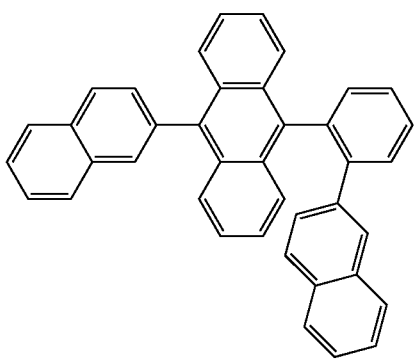
EM72
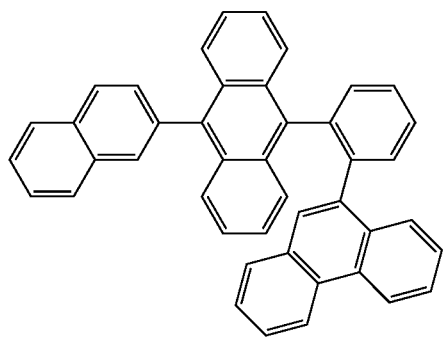
EM73
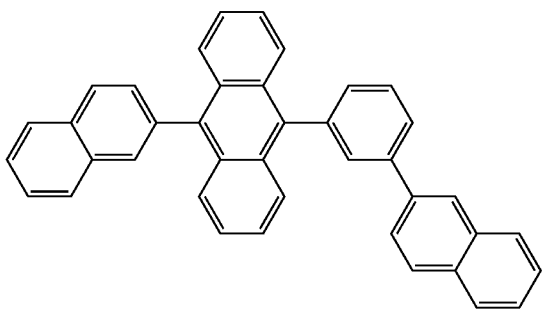
EM74
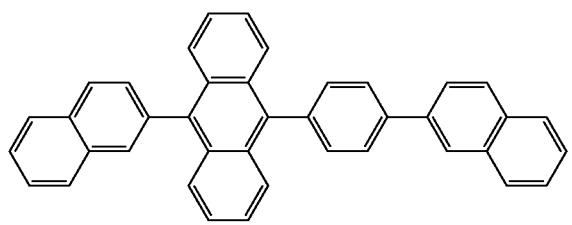
EM75
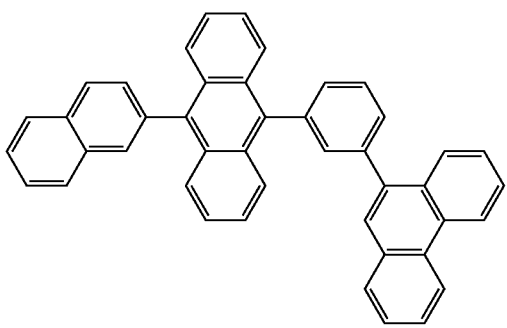

-continued
EM76
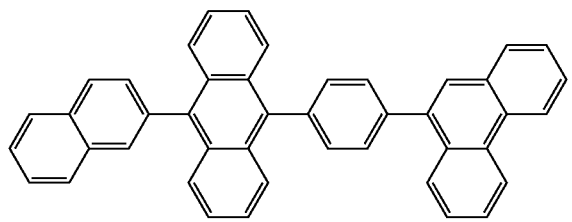
EM77
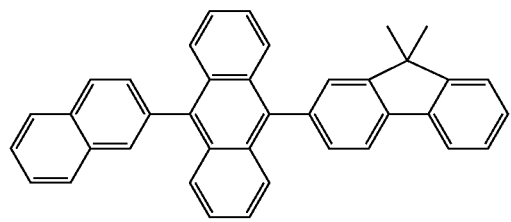
EM78
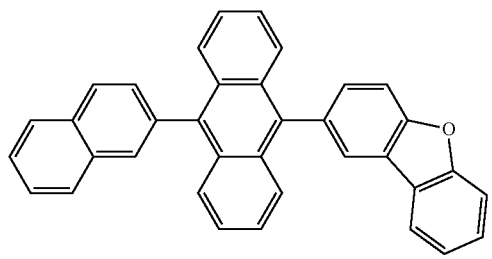
EM79
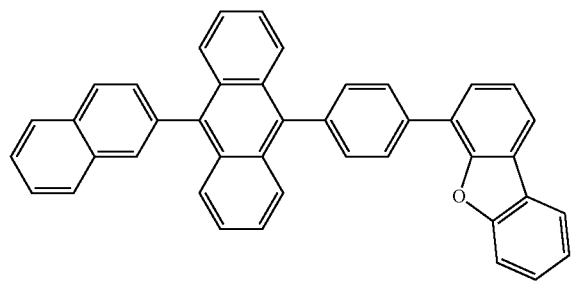
EM80
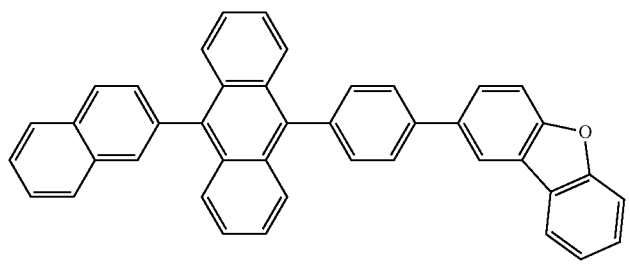
EM81
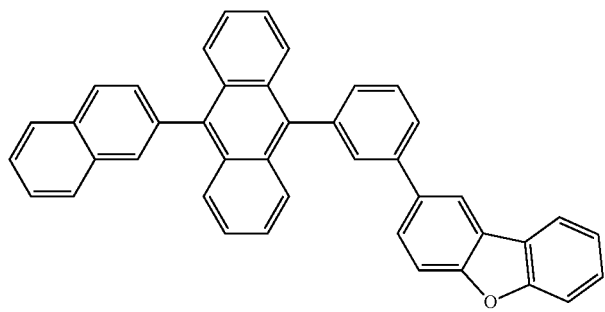
EM82
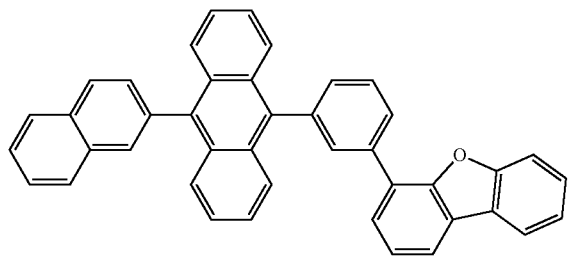
EM83
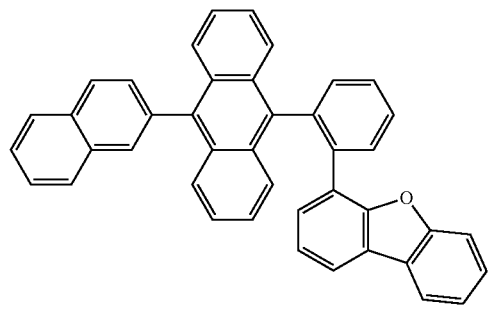

-continued
EM84
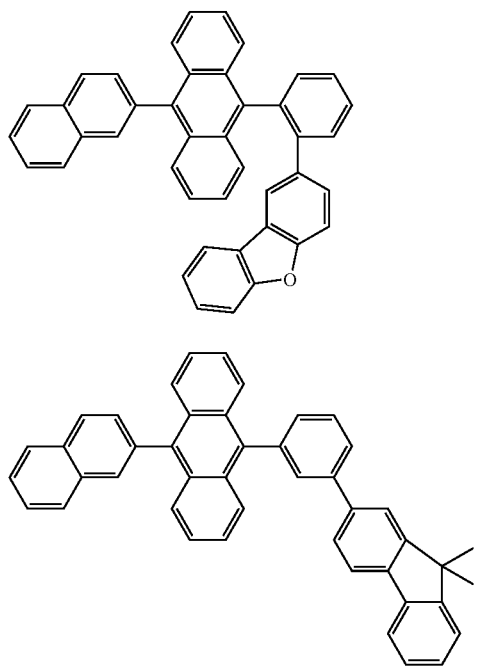
EM85
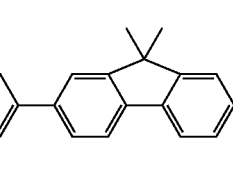
EM86
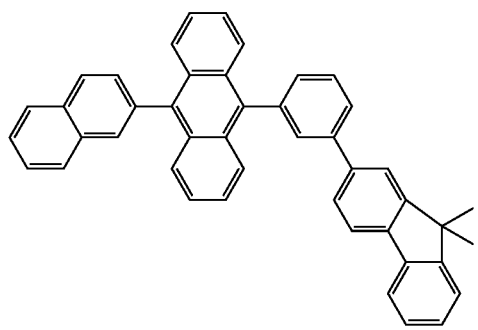
EM87
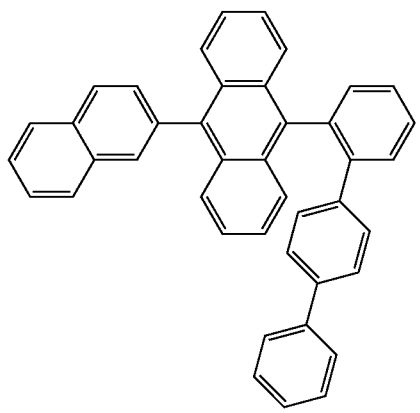
EM88
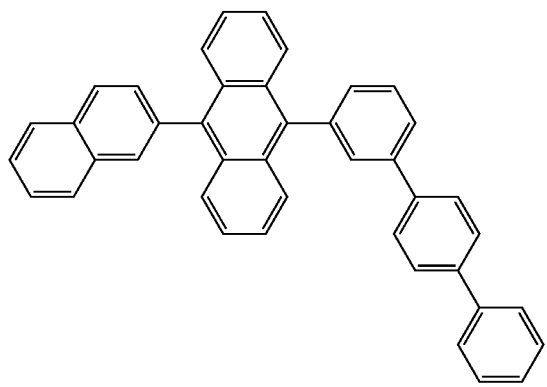
EM89
EM90
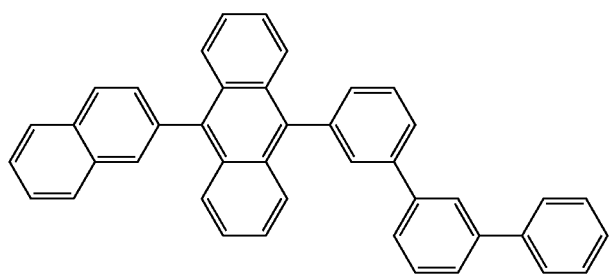
EM91
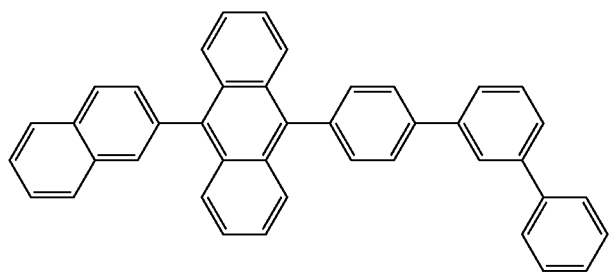

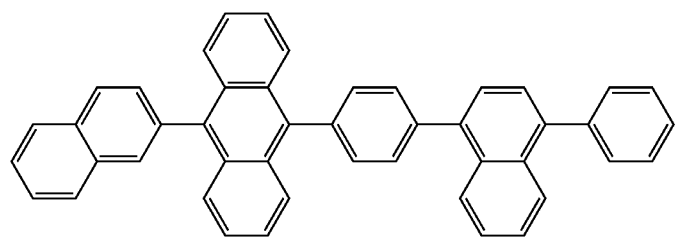
EM92
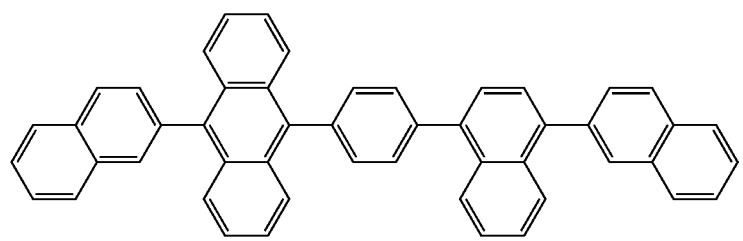
EM93
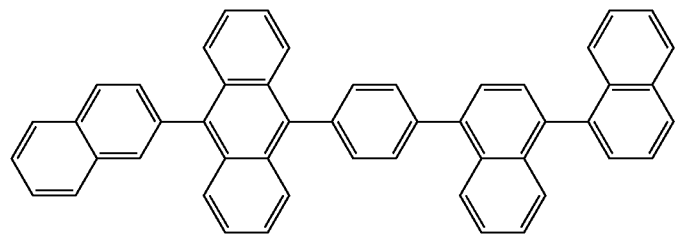
EM94
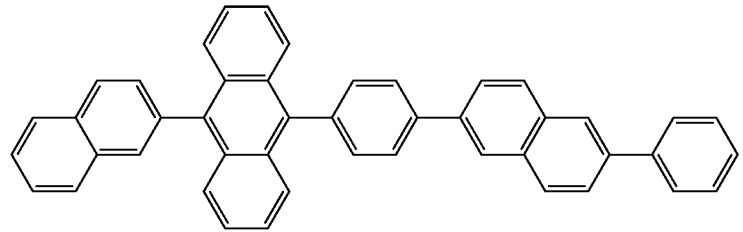
EM95
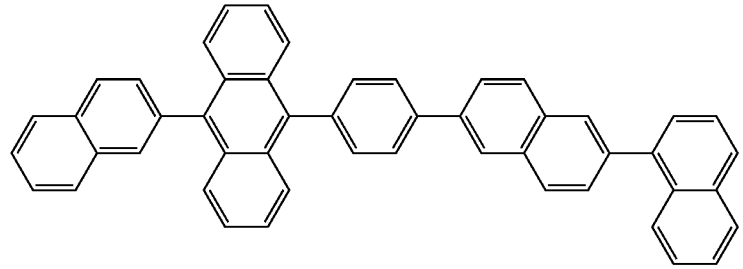
EM96
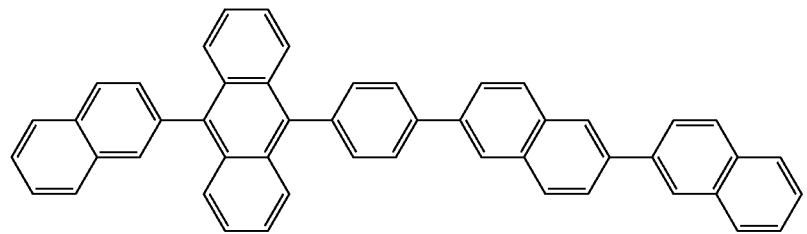
EM97

EM98
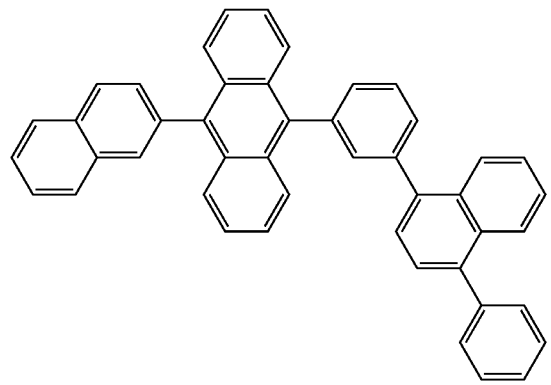
EM99
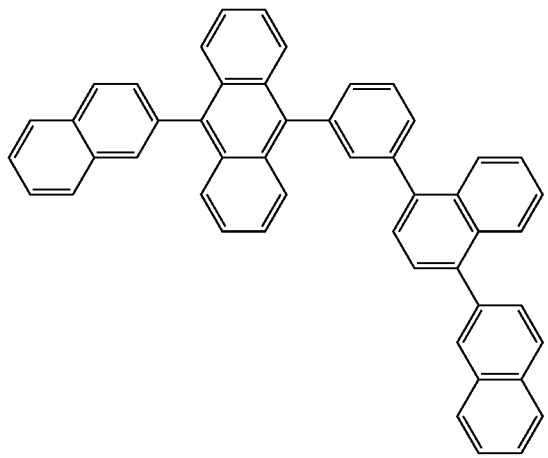
EM100
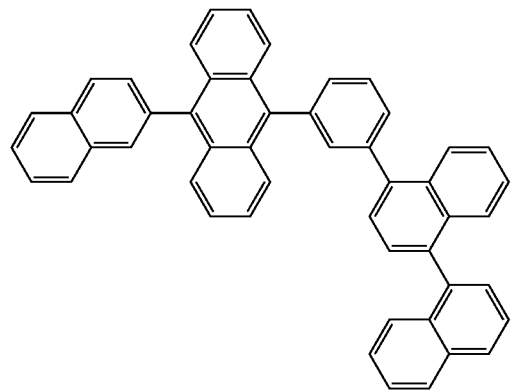
EM101
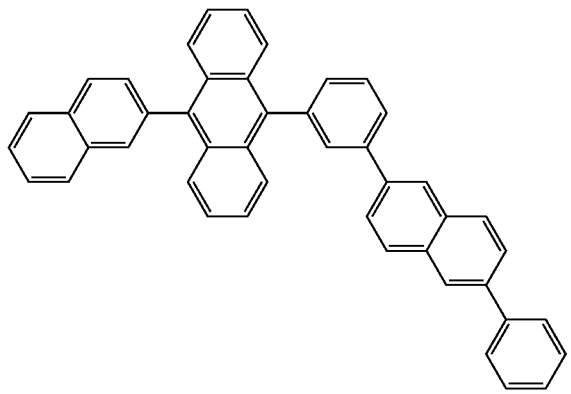
EM102
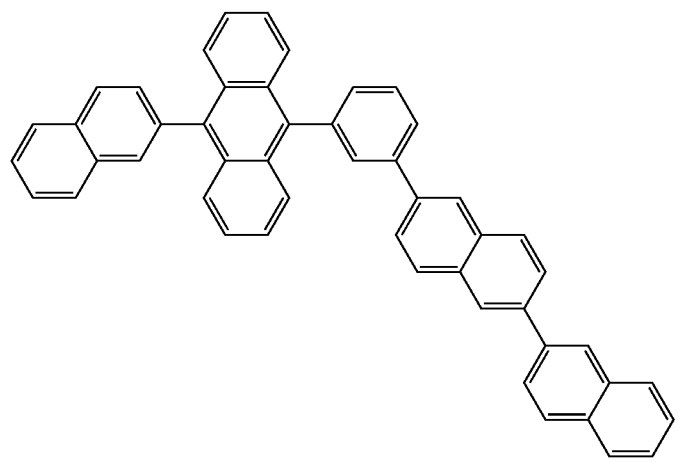

-continued
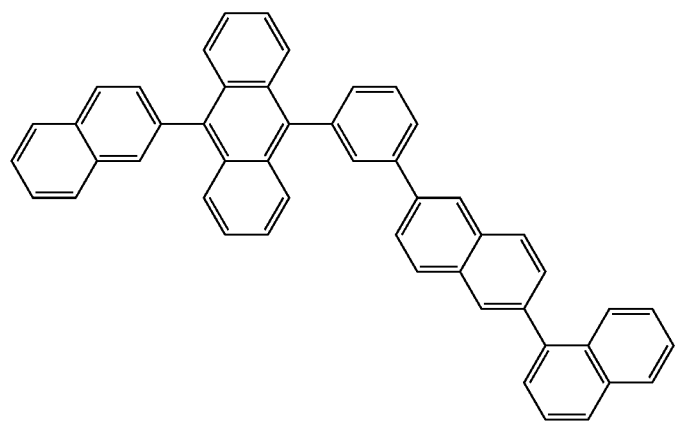
EM103
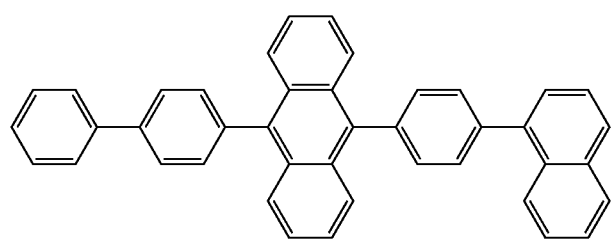
EM104
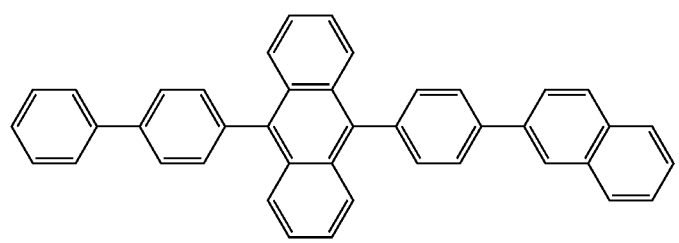
EM105
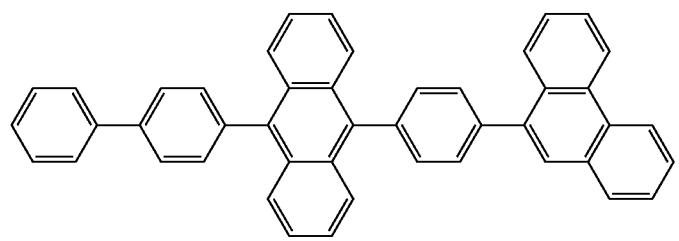
EM106
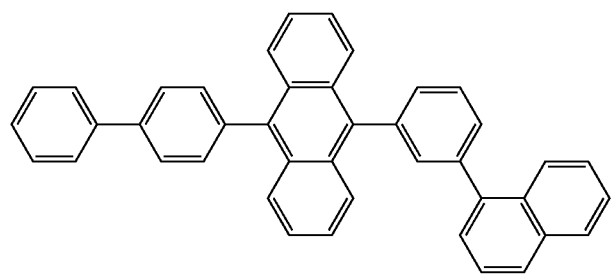
EM107

-continued
EM108
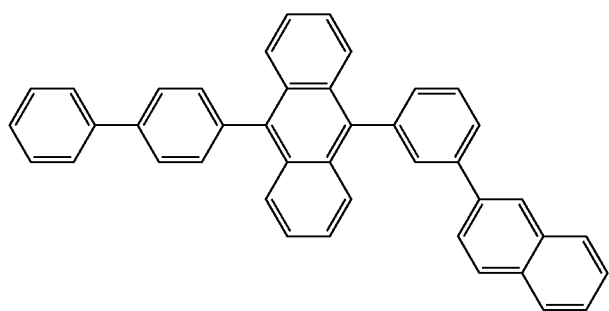
EM109
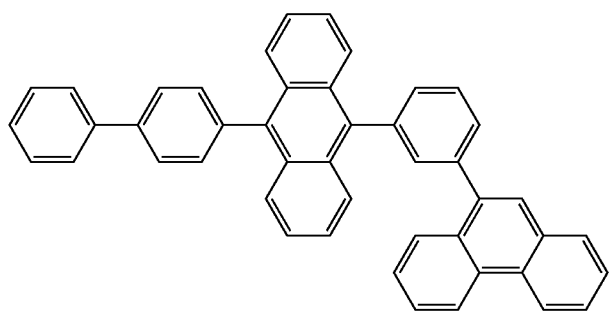
EM110
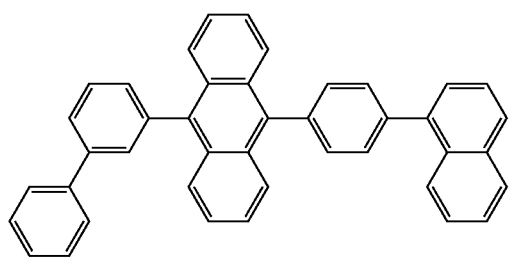
EM111
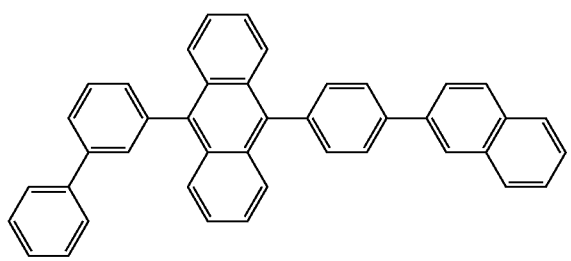
EM112
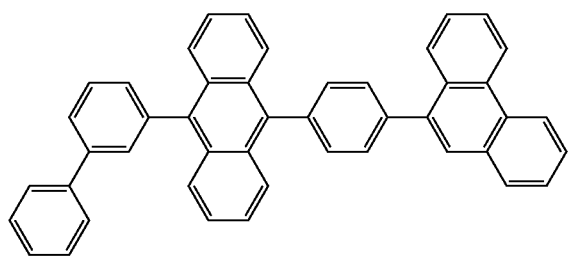
EM113
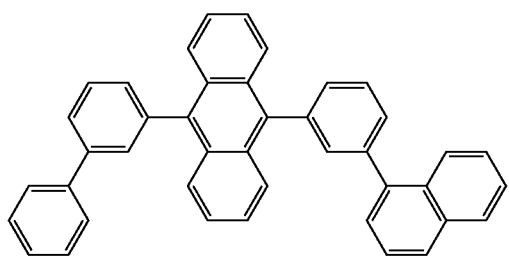
EM114
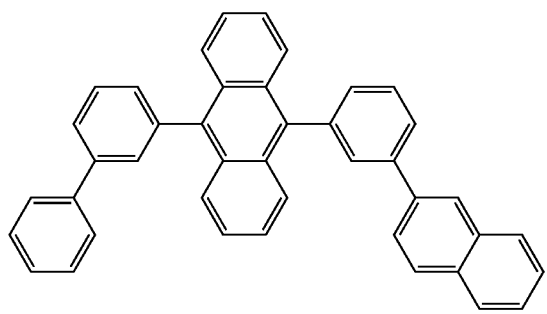
EM115
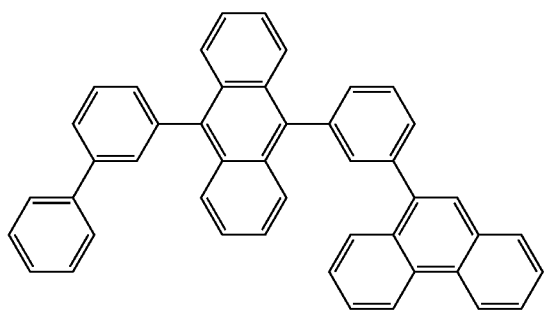

-continued
EM116
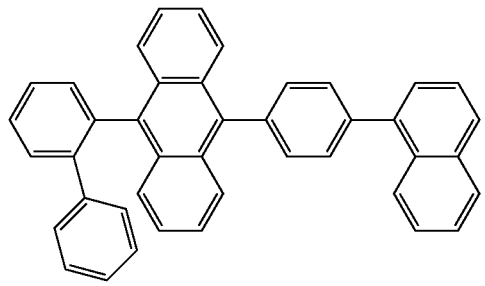
EM117
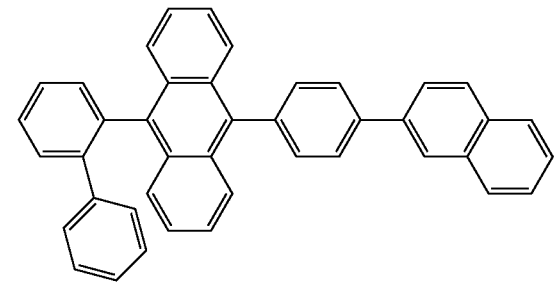
EM118
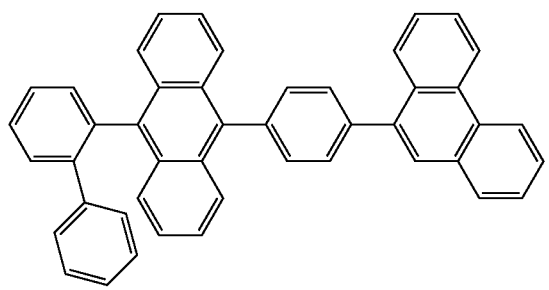
EM119
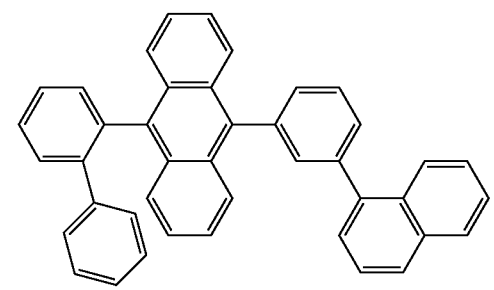
EM120
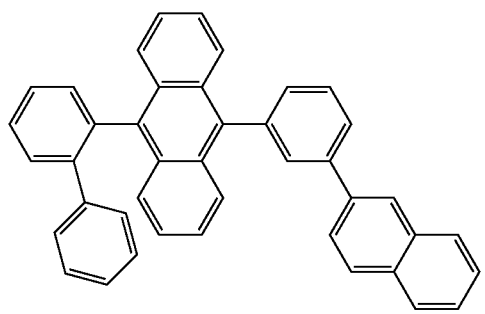
EM121
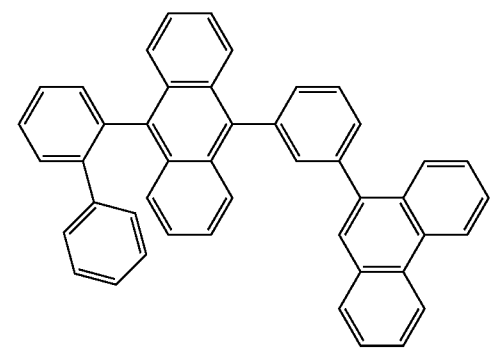
EM122
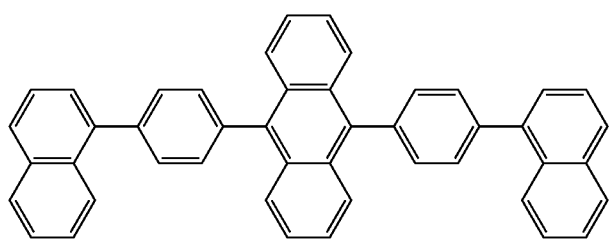
EM123
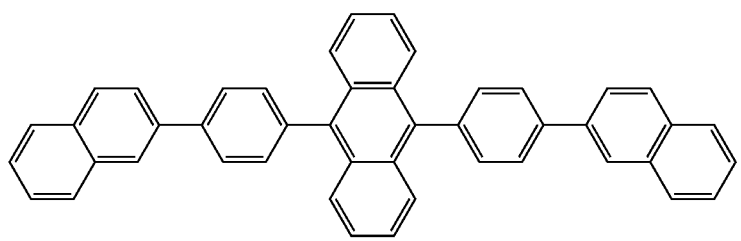

-continued
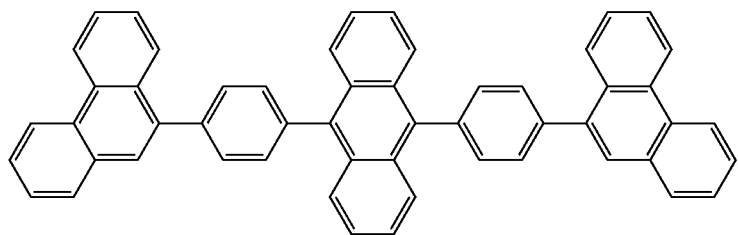
EM124
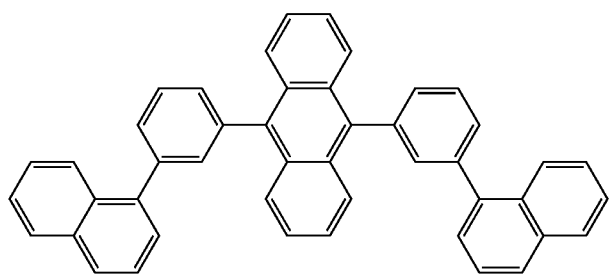
EM125
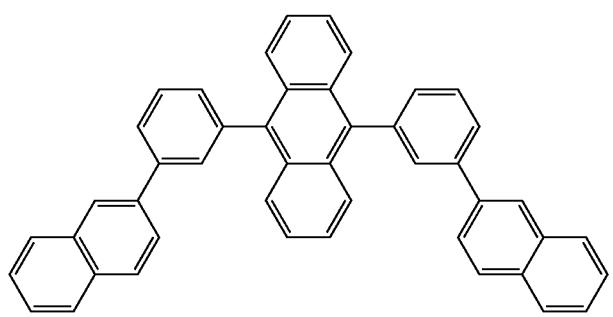
EM126
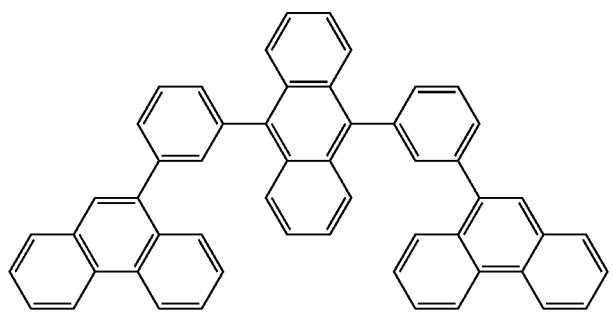
EM127
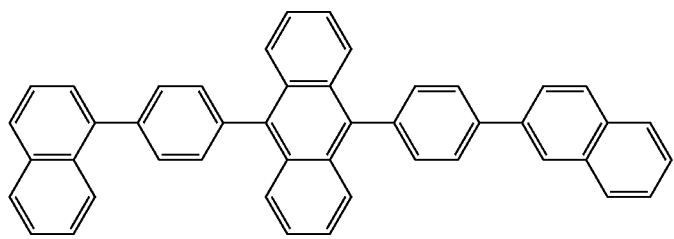
EM128

-continued
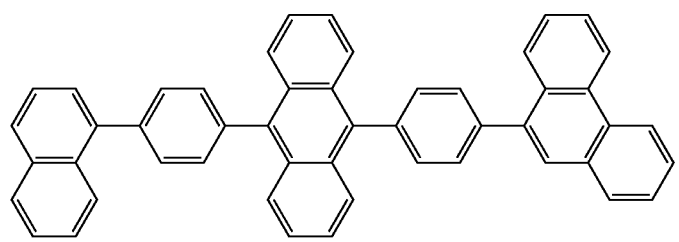
EM129
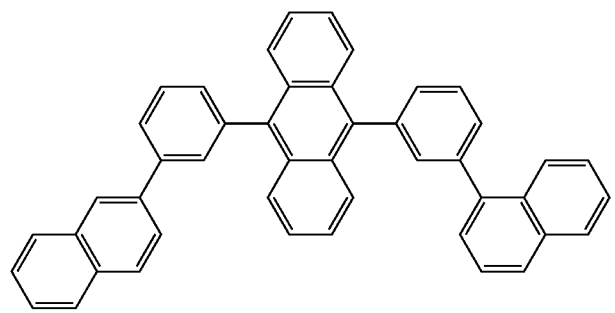
EM130
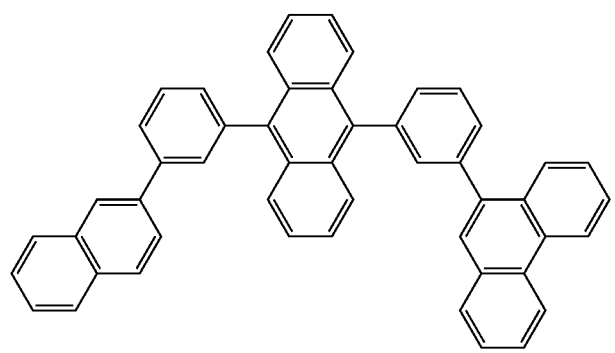
EM131
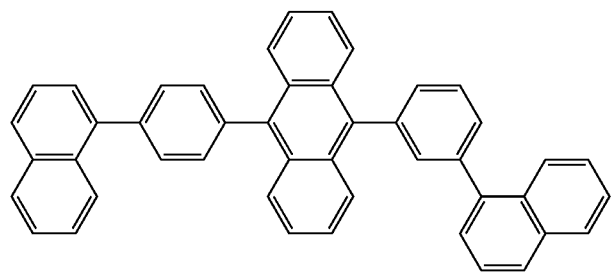
EM132
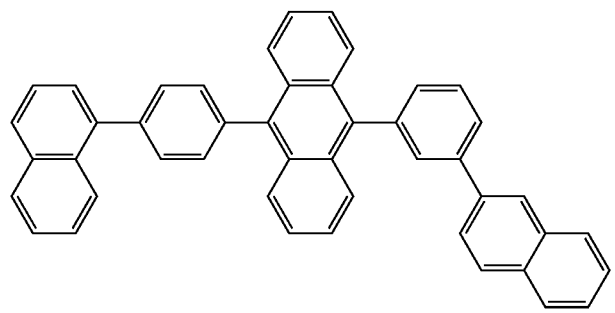
EM133

-continued
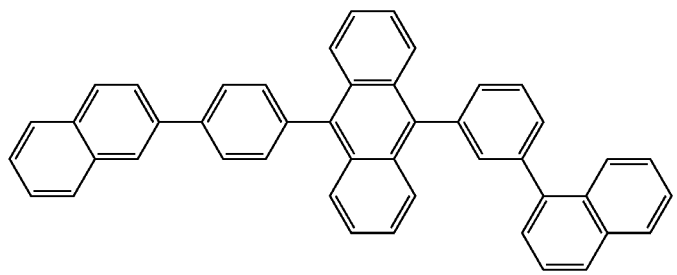
EM134
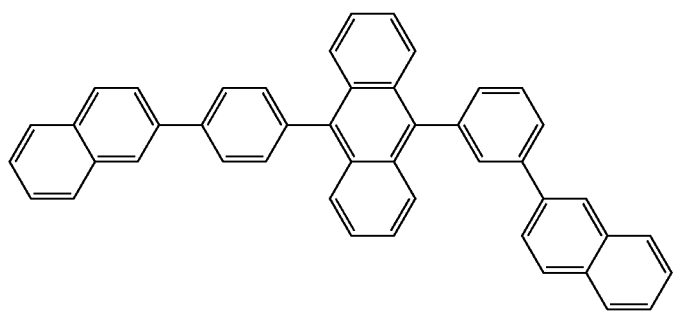
EM135
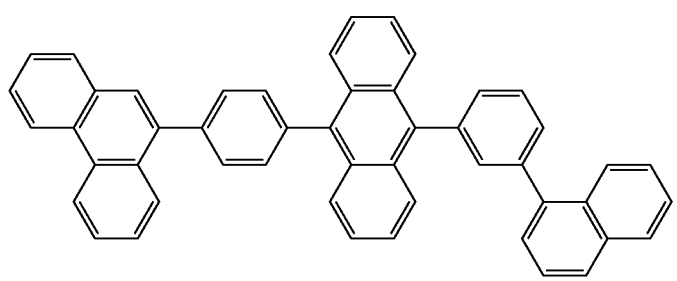
EM136
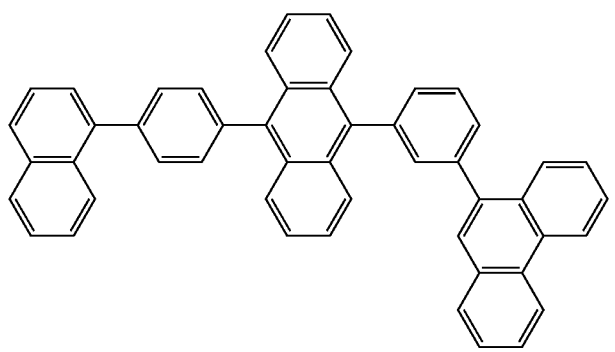
EM137
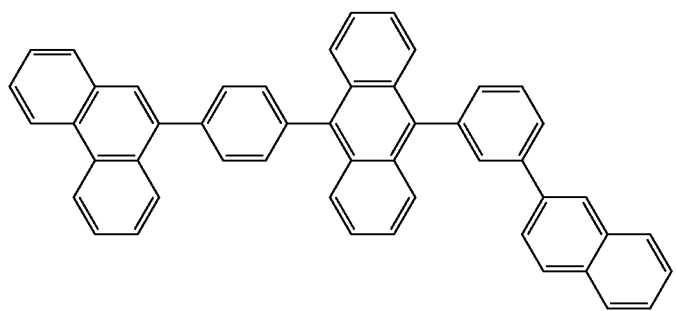
EM138

EM139
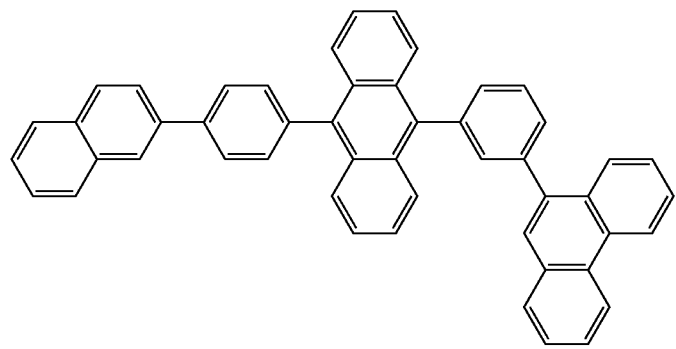
EM140
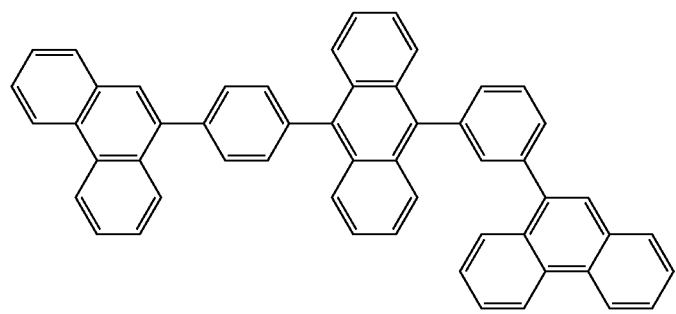
EM141
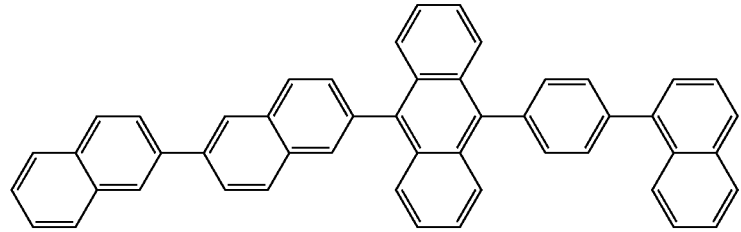
EM142
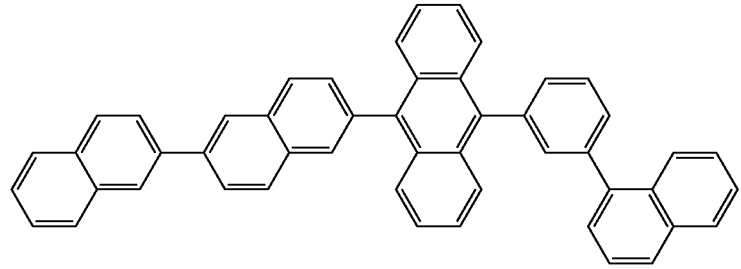
EM143
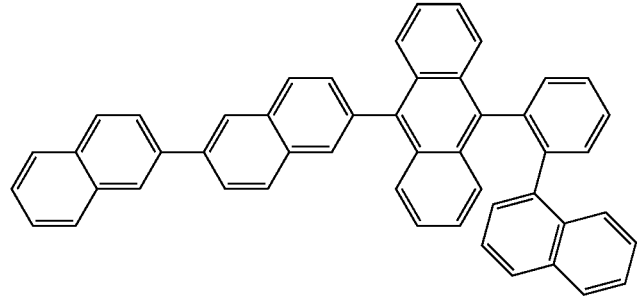

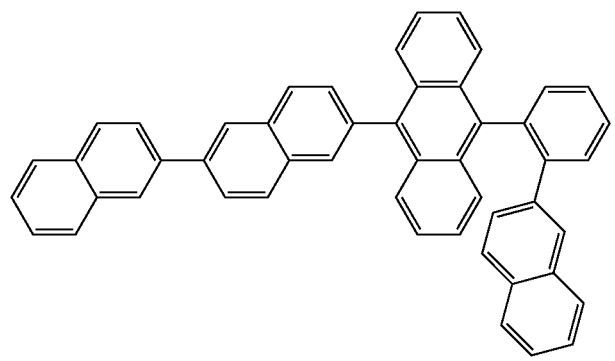
EM144
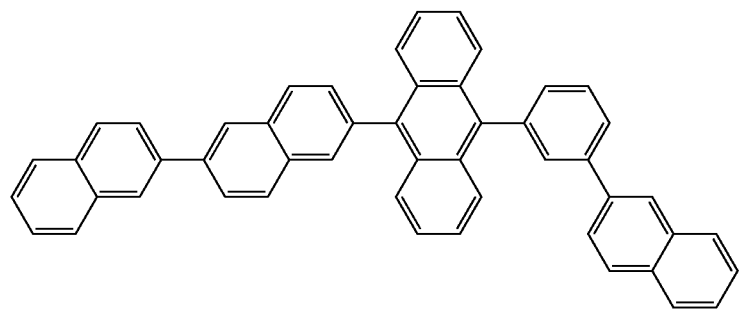
EM145
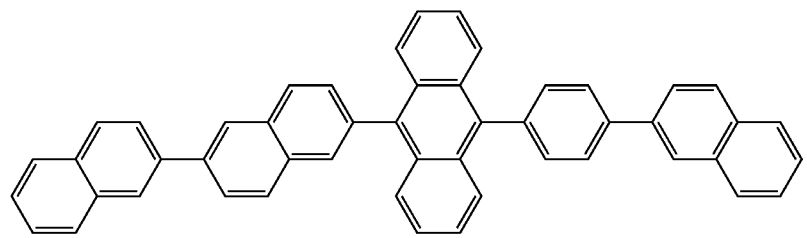
EM146
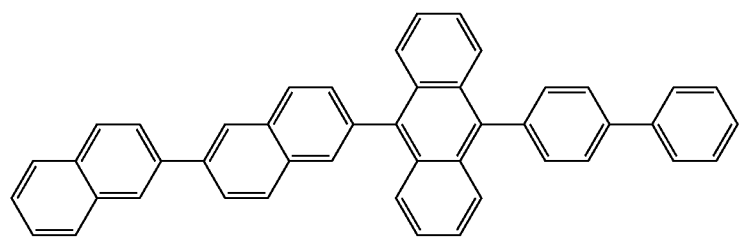
EM147
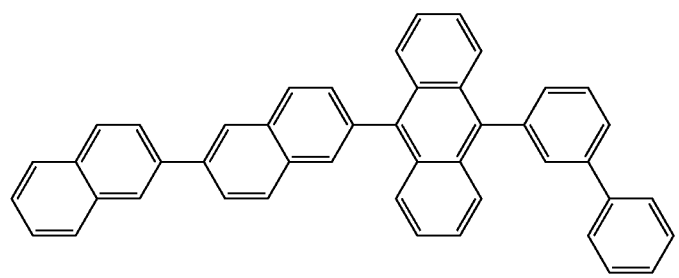
EM148

-continued
EM149
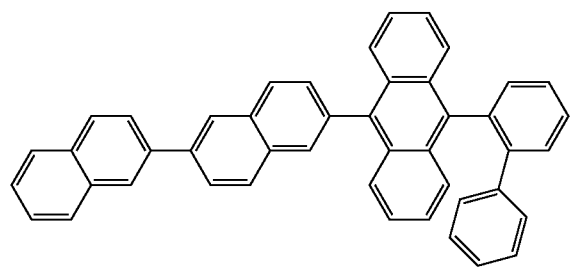
EM150
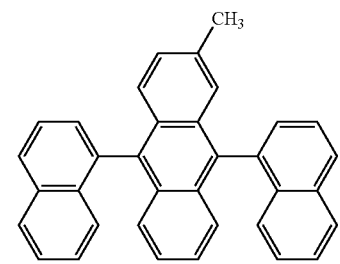
EM151
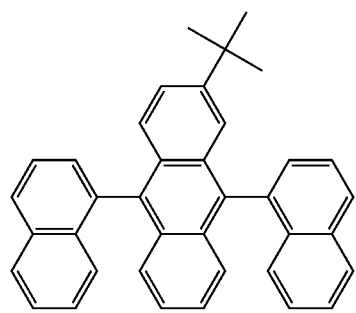
EM152
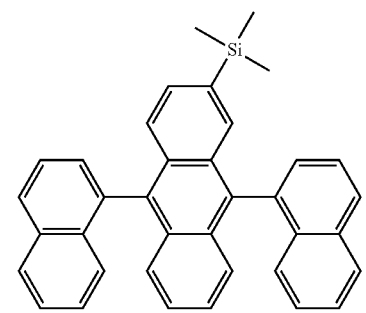
EM153
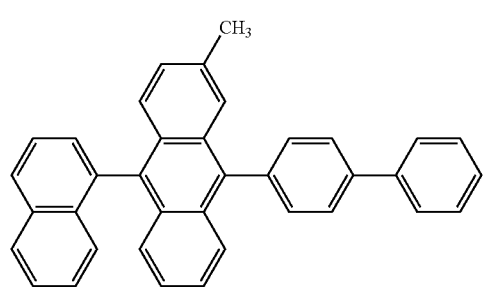
EM154
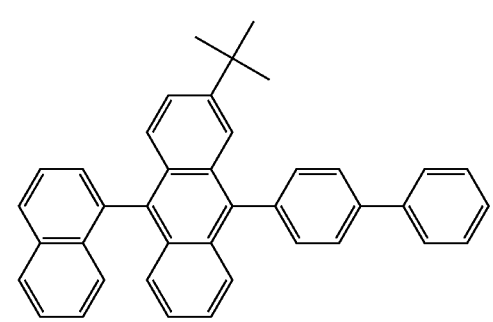
EM155
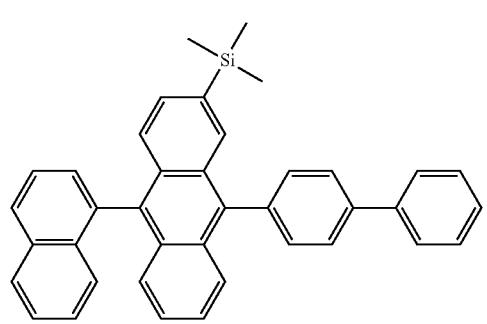
EM156
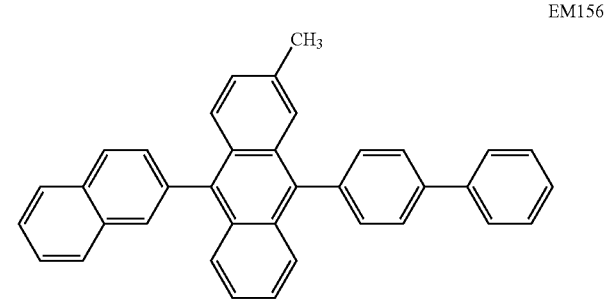
EM157
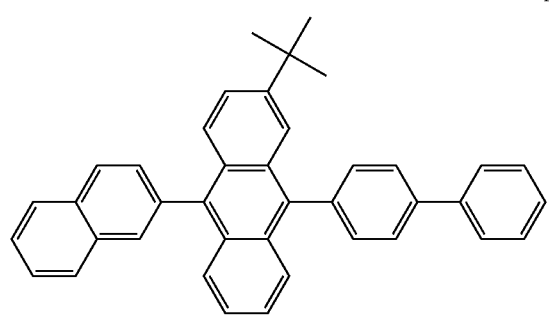
EM158
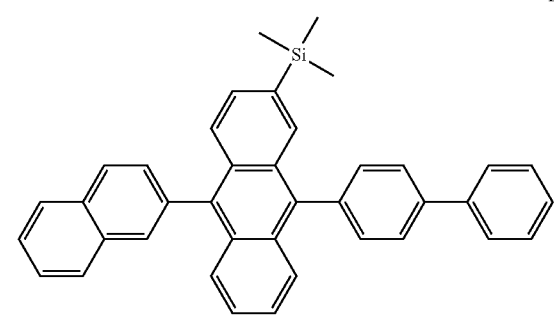

EM159
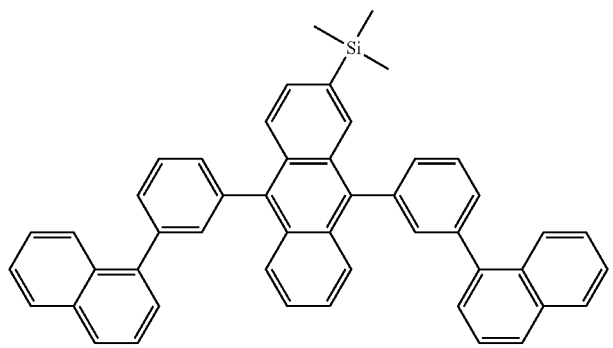
EM160
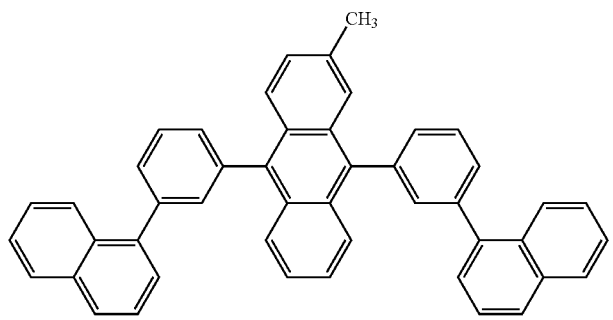
EM161    EM162
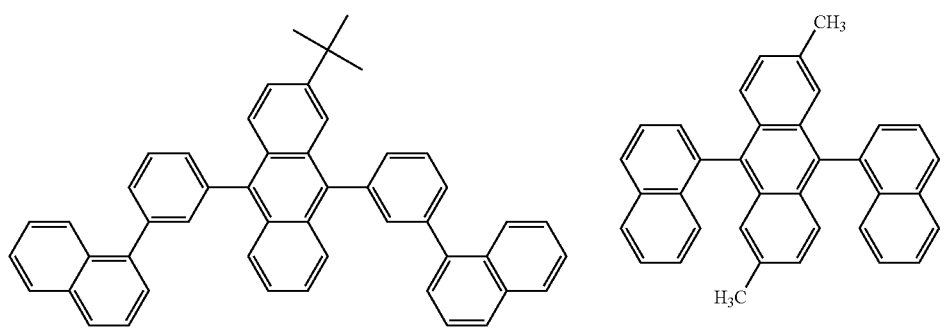
EM163    EM164
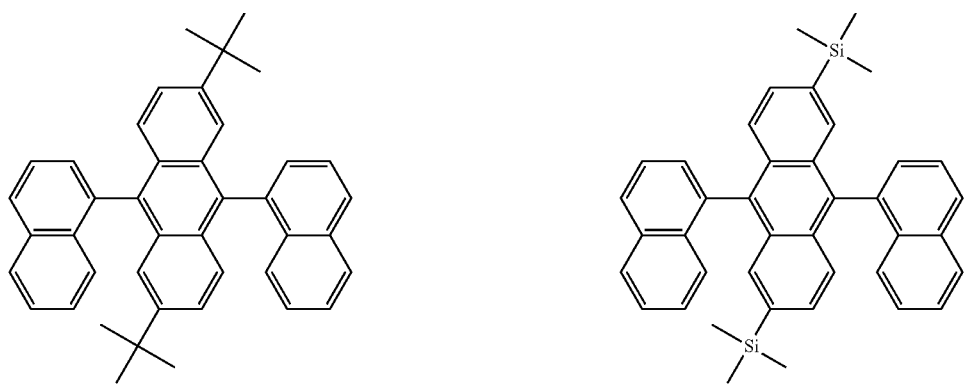

-continued
EM165
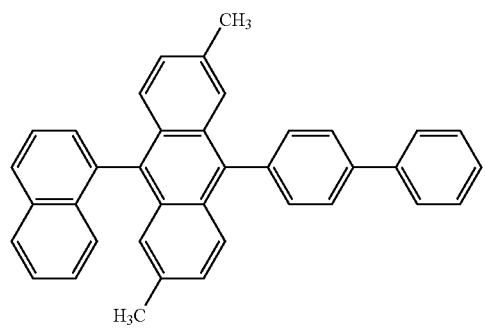
EM166
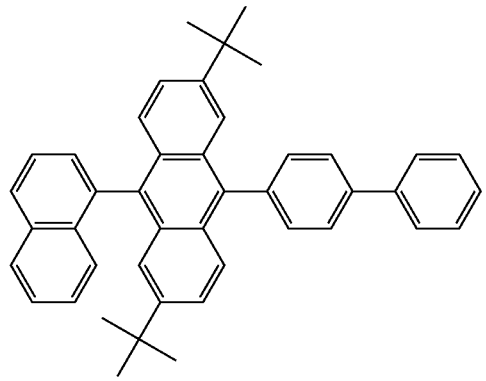
EM167
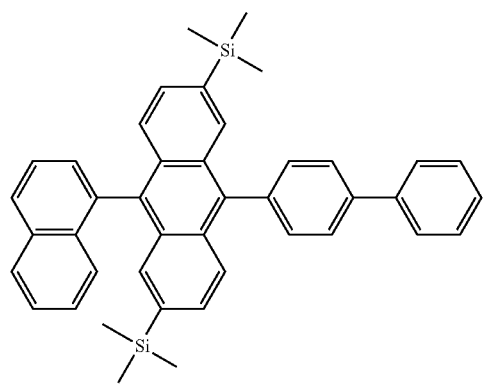
EM168
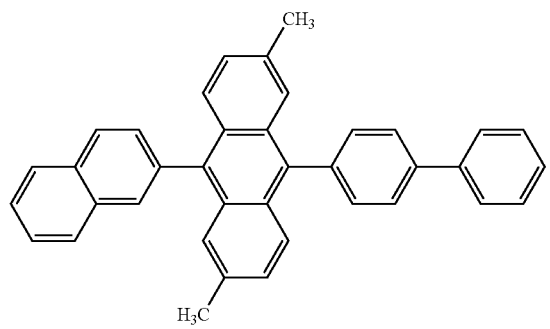
EM169
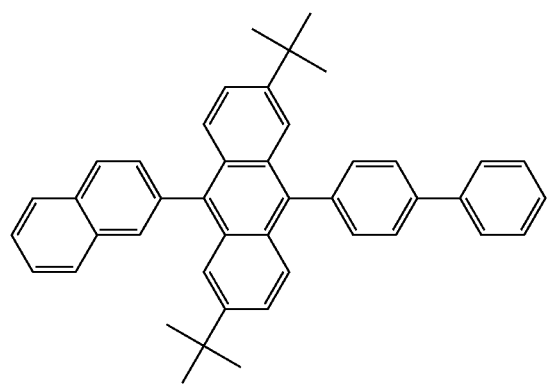
EM170
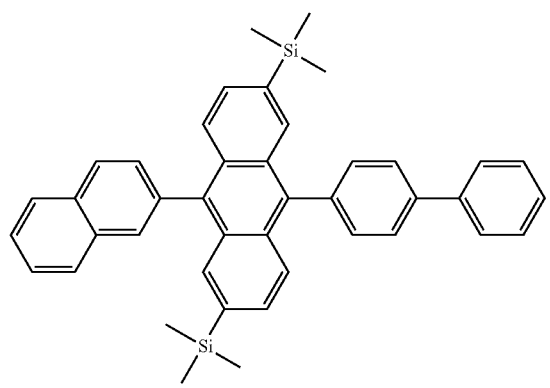
EM171
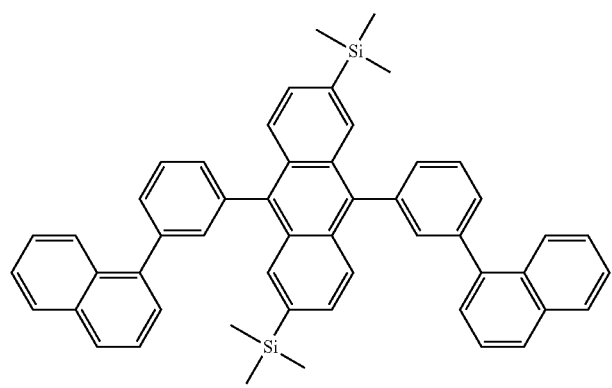

EM172
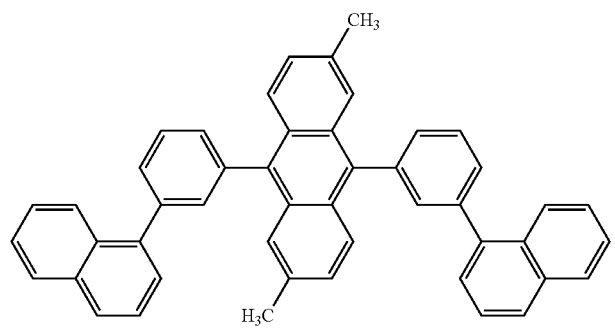
EM173
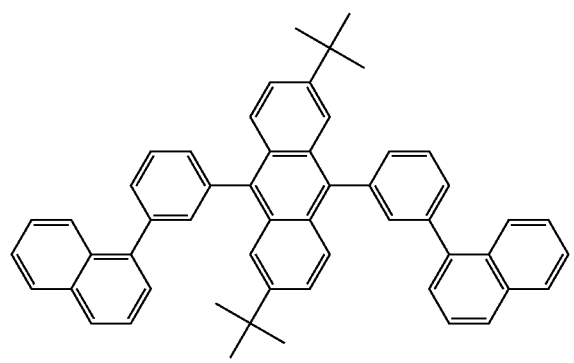
EM174
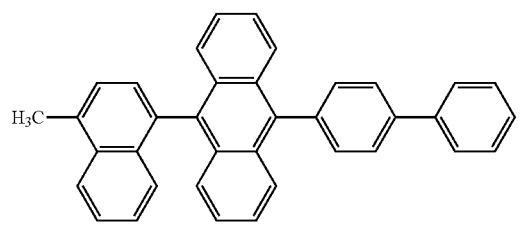
EM175
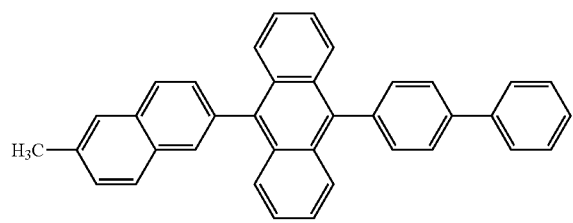
EM176
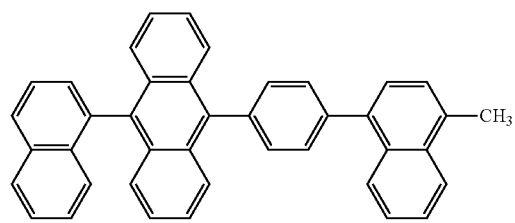
EM177
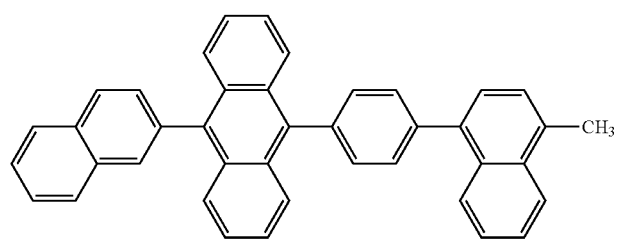
EM178
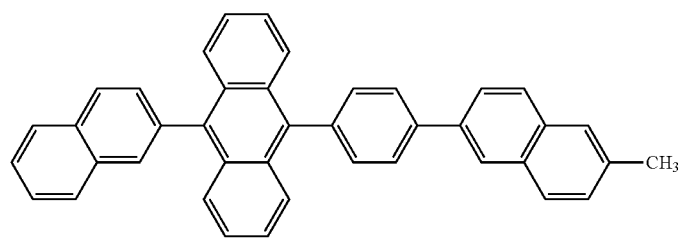

-continued
EM179
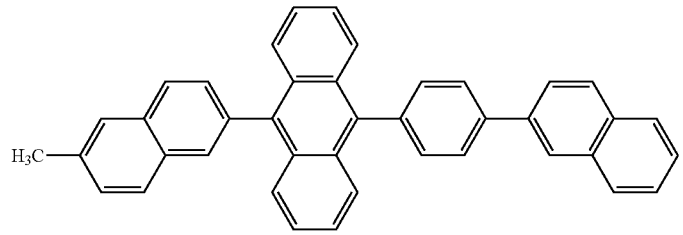
EM180
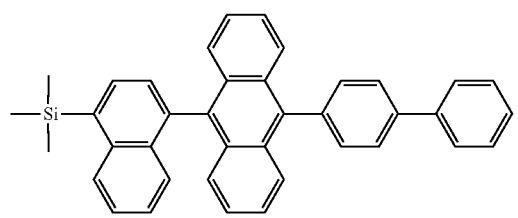
EM181
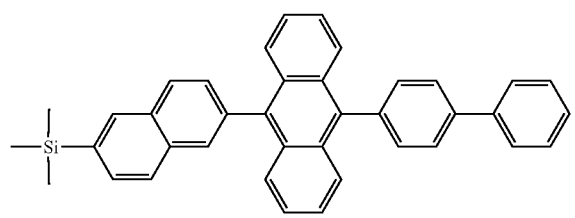
EM182
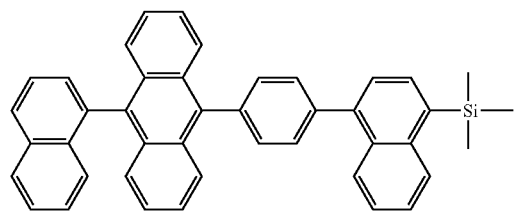
EM183
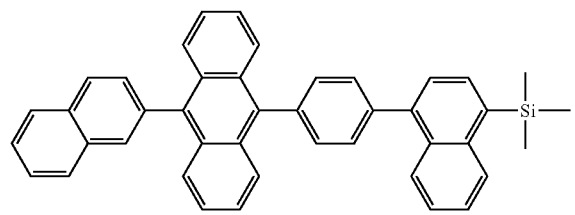
EM184
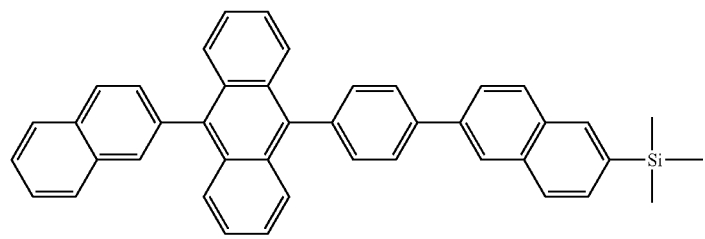
EM185
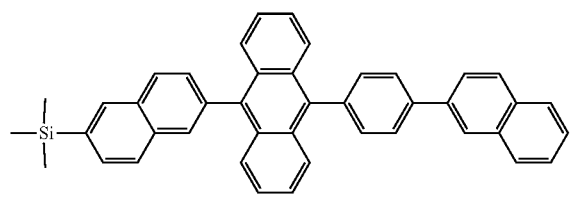
EM186
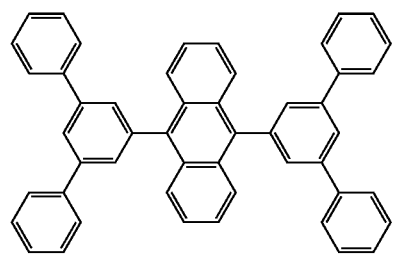

-continued
EM187
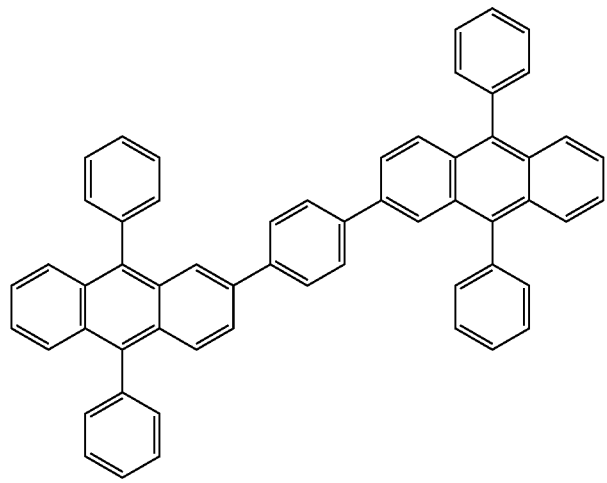
EM188
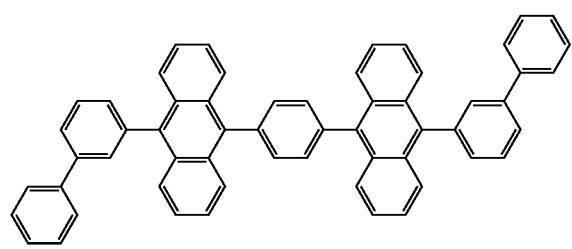
EM189
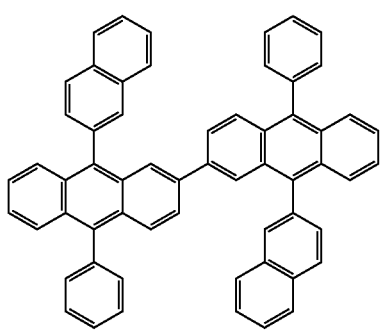
EM190
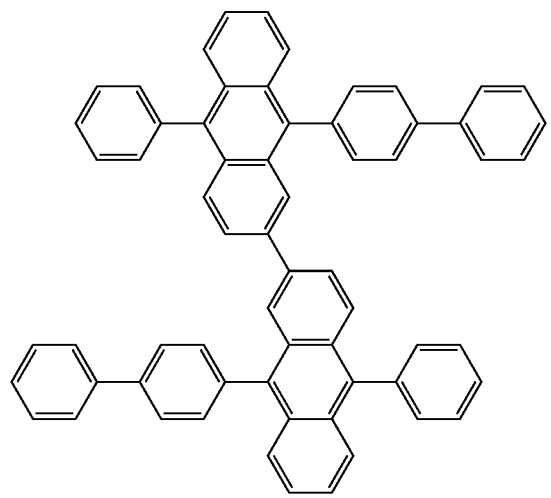
EM191
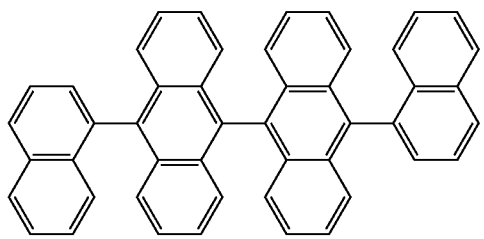
EM192
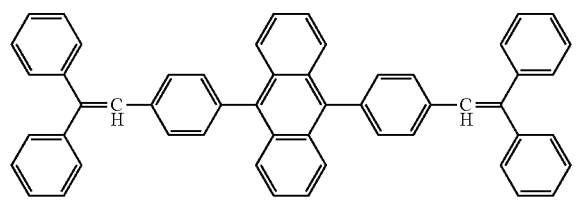
EM193
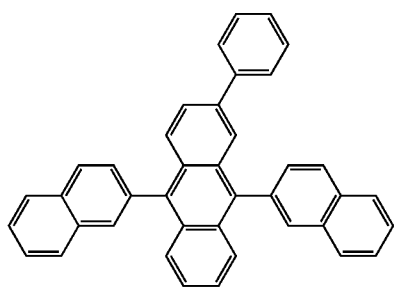

-continued
EM194
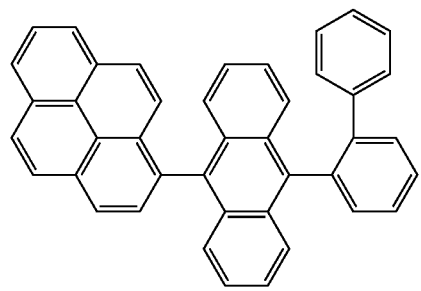
EM195
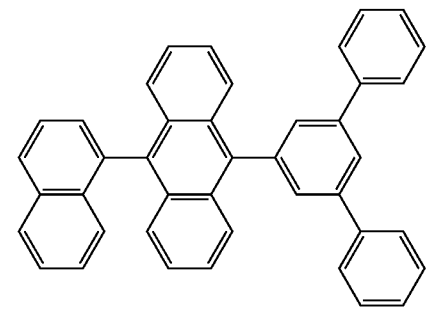
EM196
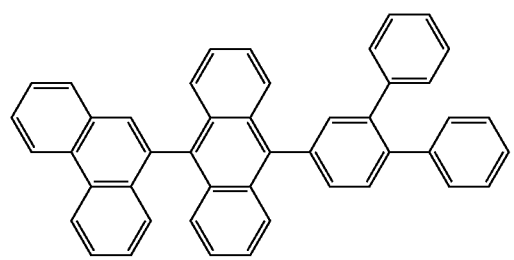
EM197
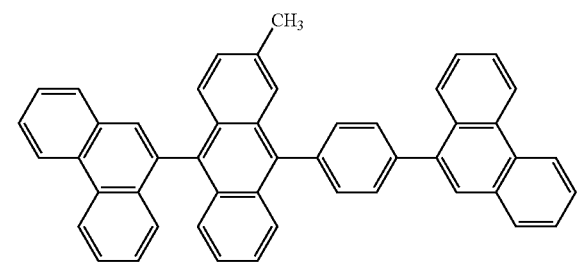
EM198
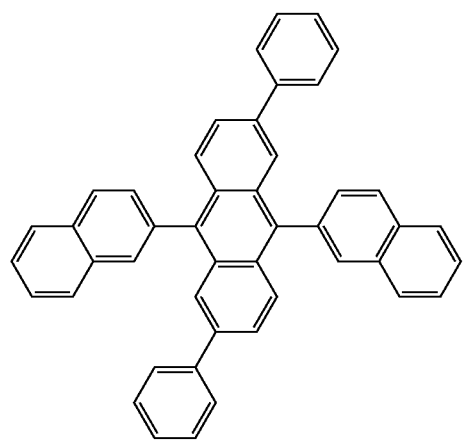
EM199
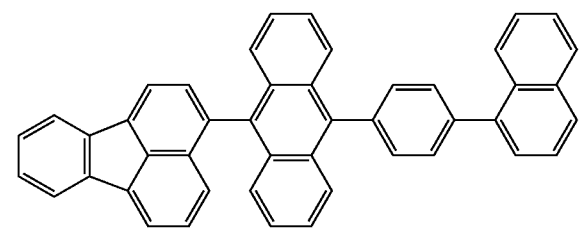
EM200
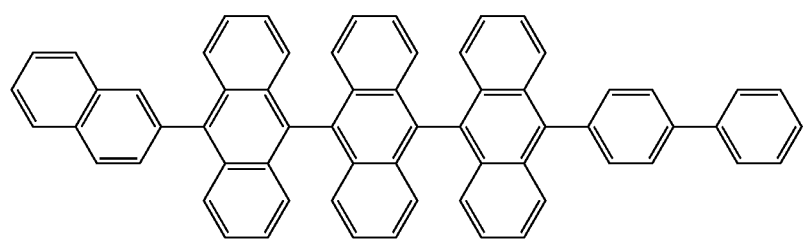
EM201
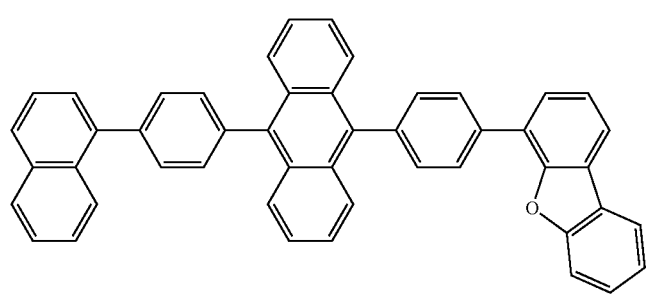

-continued
EM202
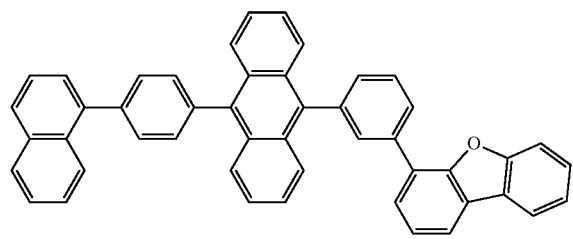
EM203
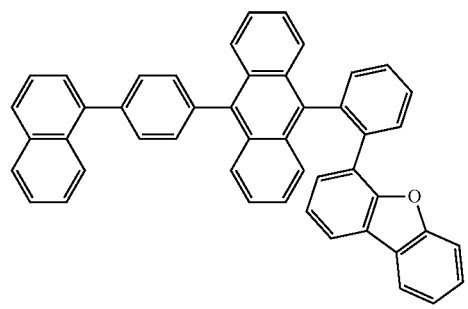
EM204
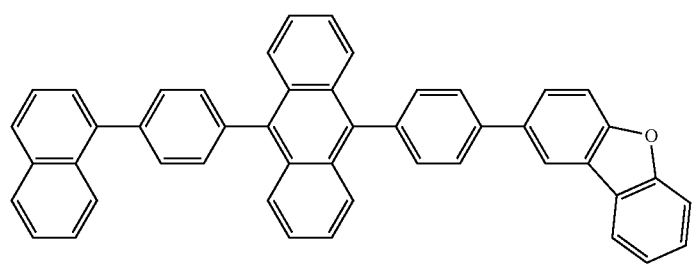
EM205
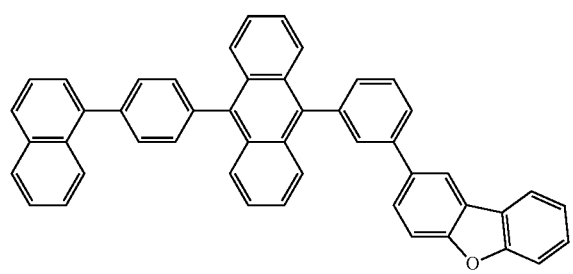
EM206
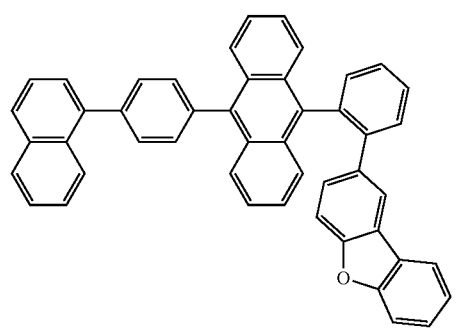
EM207
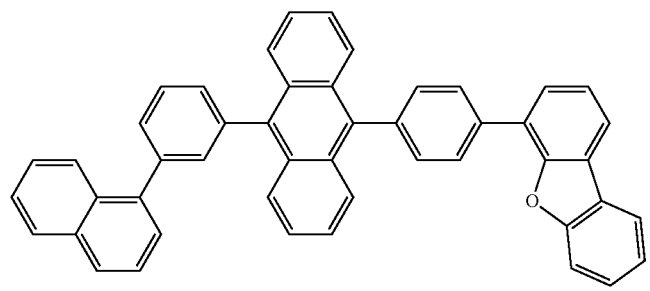
EM208
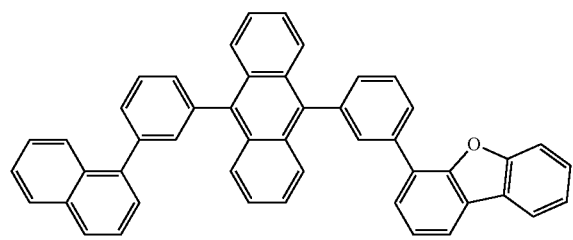
EM209
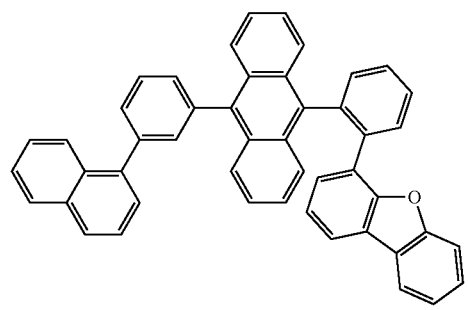

-continued
EM210
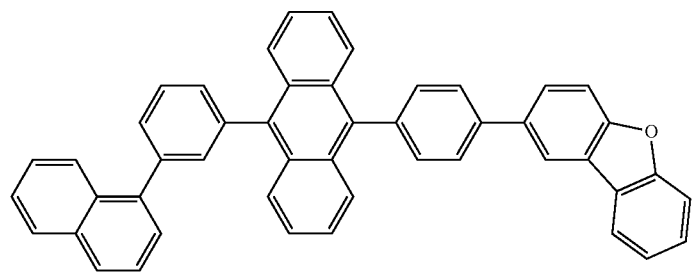
EM211
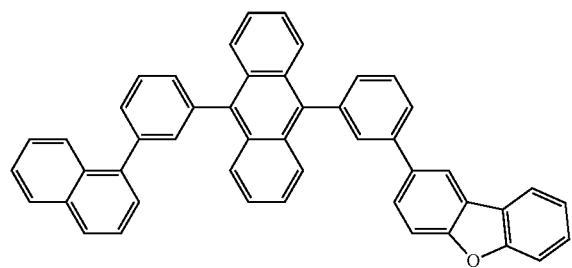
EM212
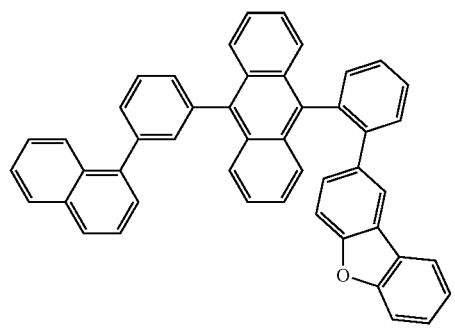
EM213
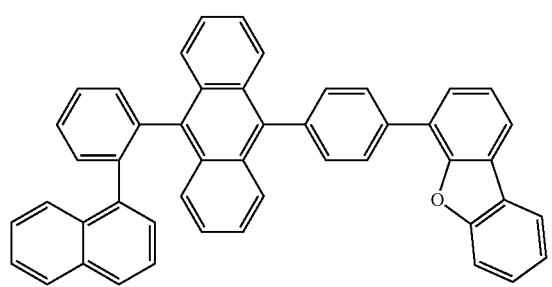
EM214
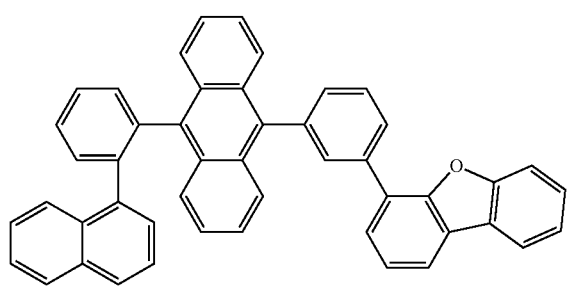
EM215
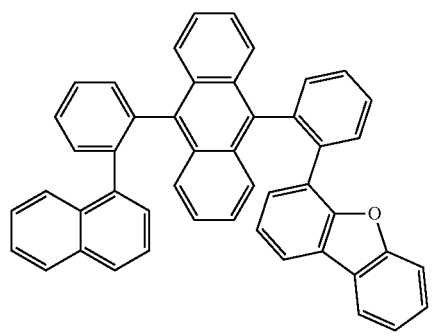
EM216
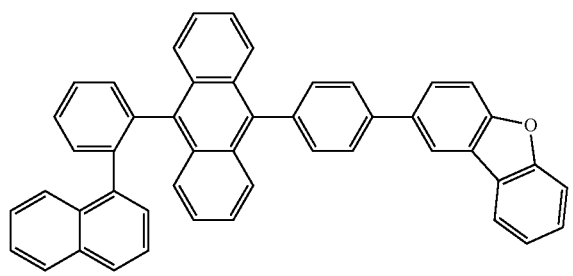
EM217
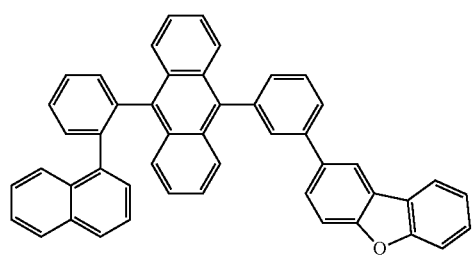
EM218
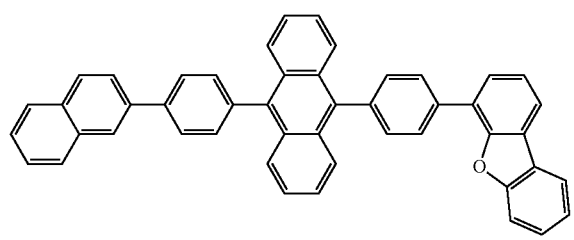

-continued
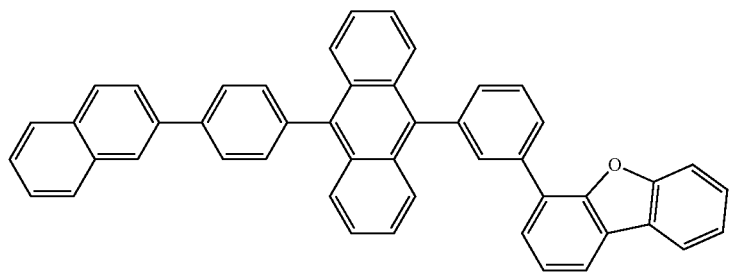
EM219
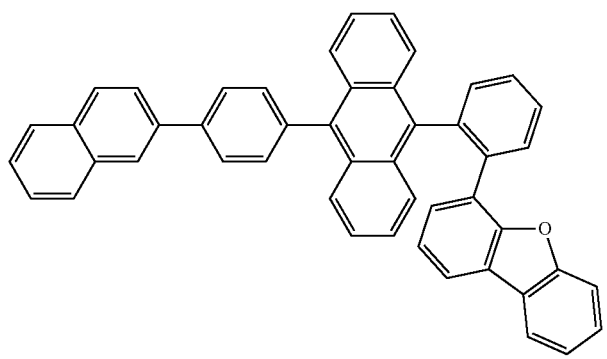
EM220
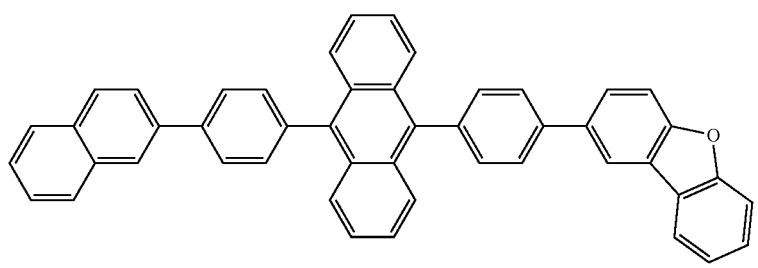
EM221
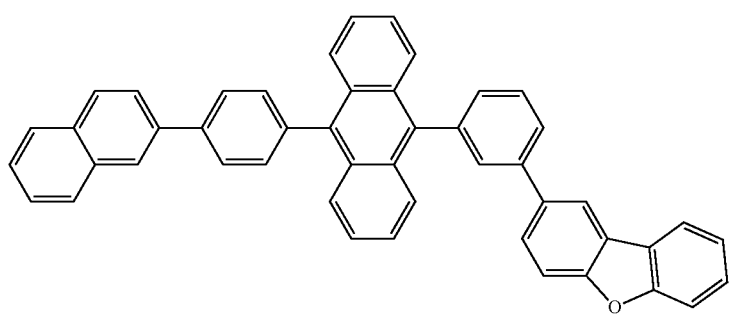
EM222
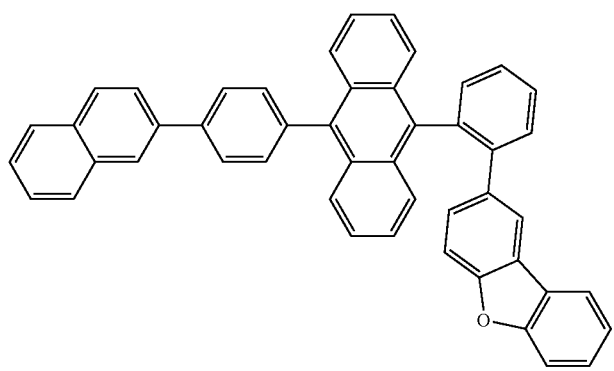
EM223

EM224
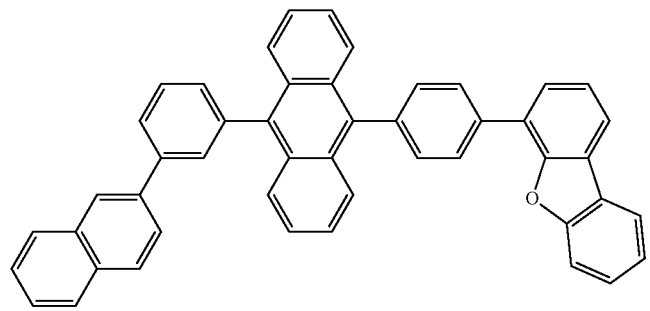
EM225
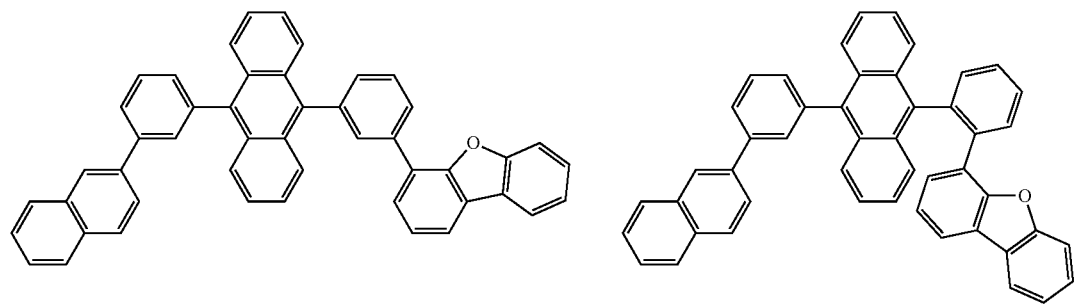
EM226
EM227
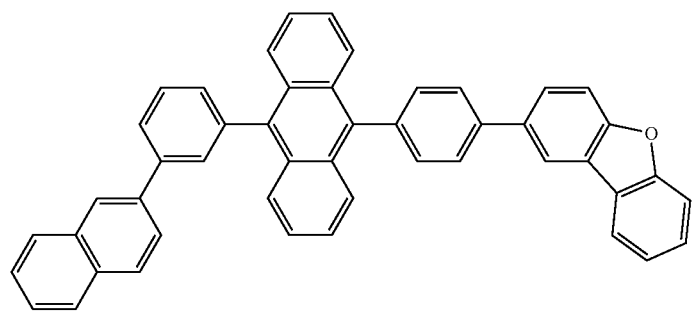
EM228
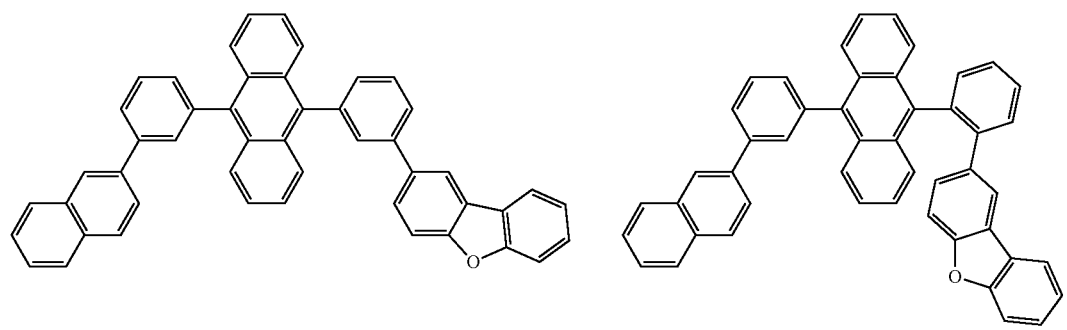
EM229

-continued
EM230
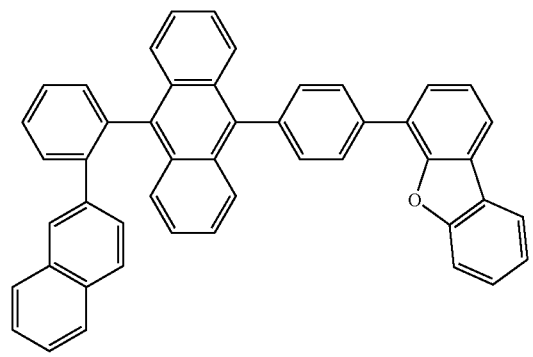
EM231
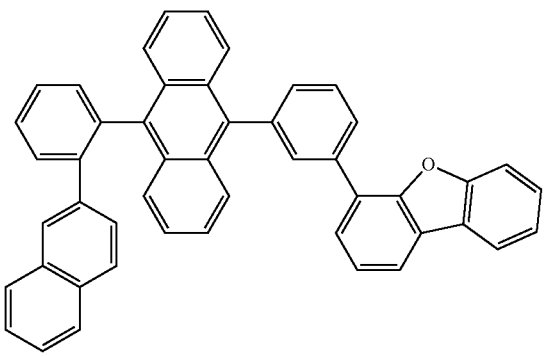
EM232
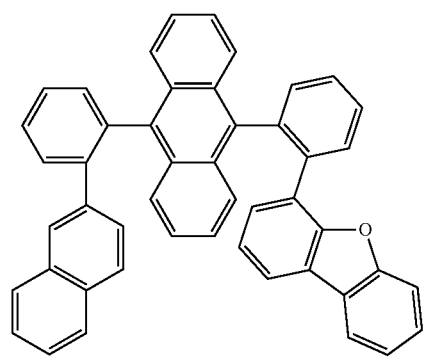
EM233
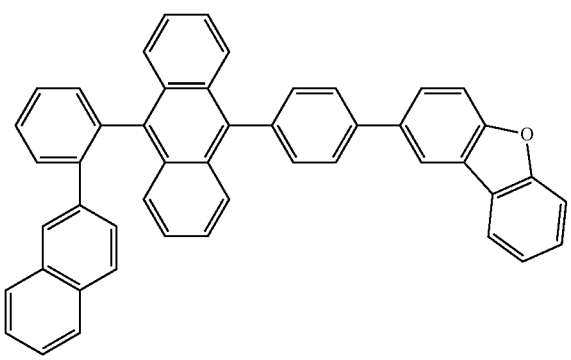
EM234
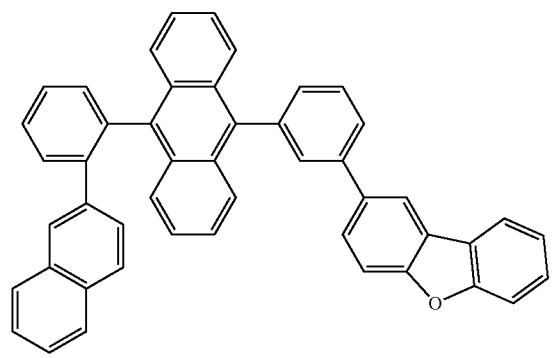
EM235
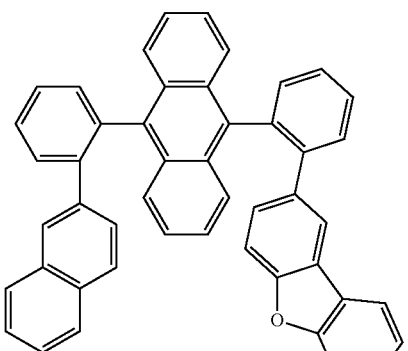
EM236
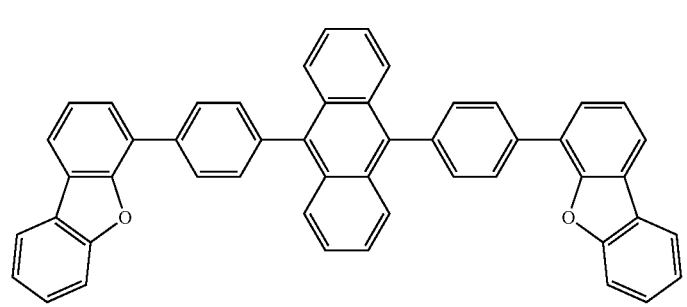

EM237
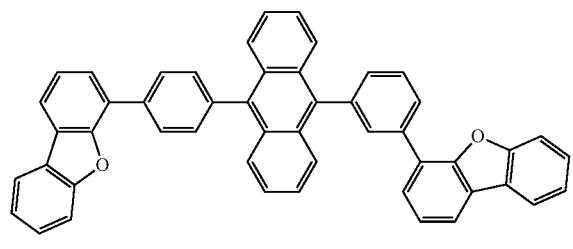
EM238
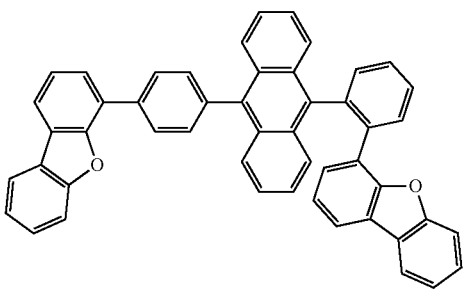
EM239
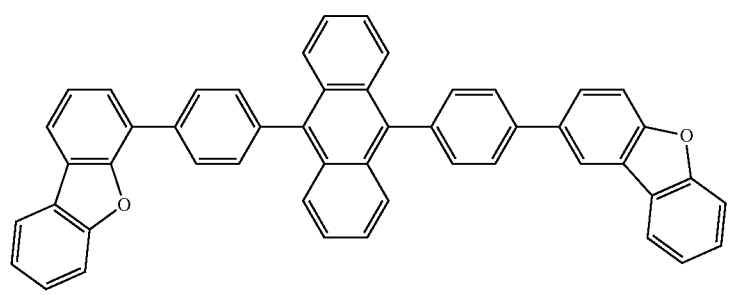
EM240
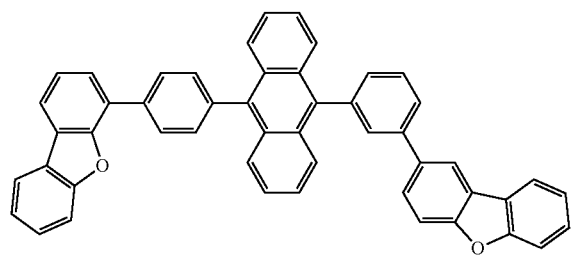
EM241
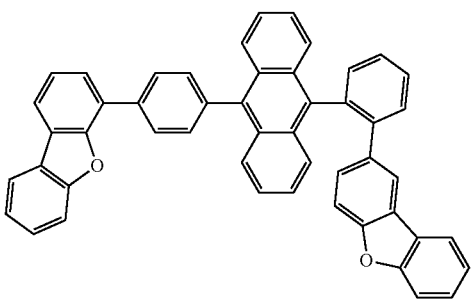
EM242
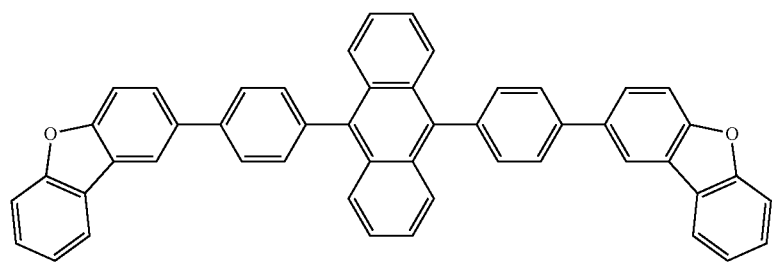
EM243
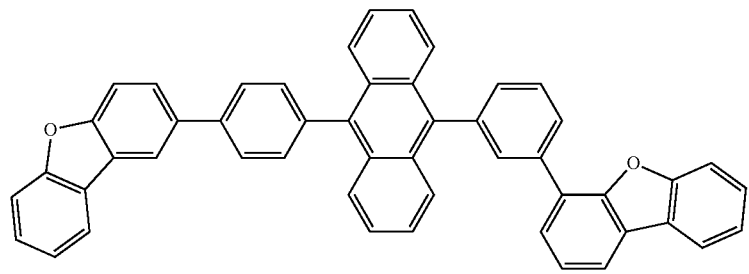

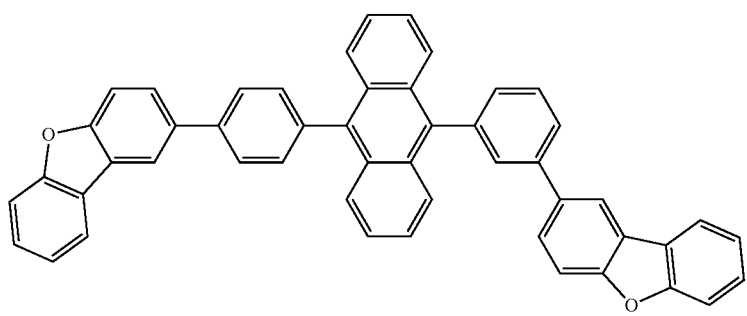
EM244
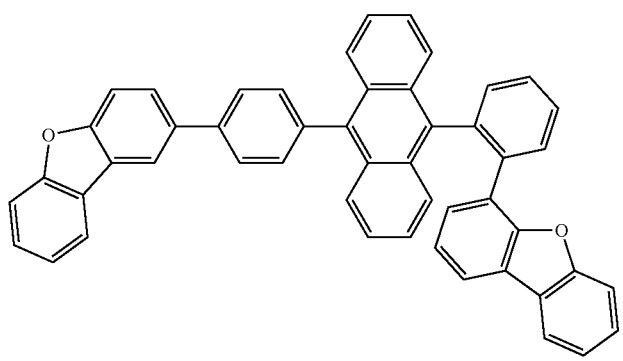
EM245
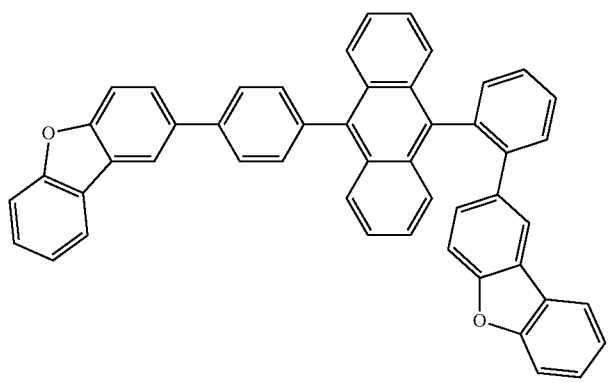
EM246
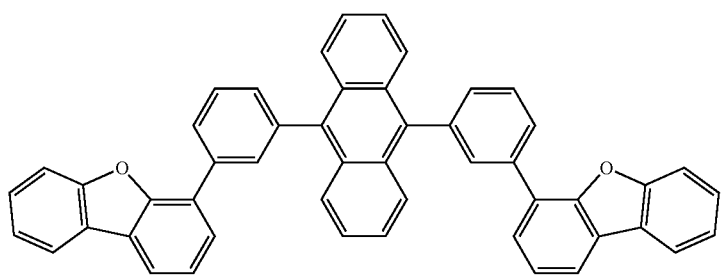
EM24

EM248
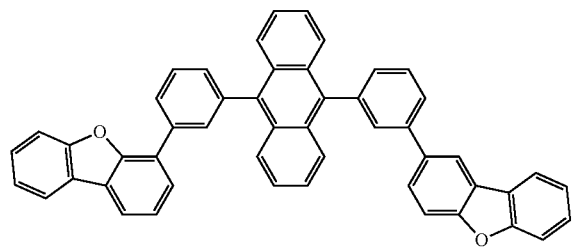
EM249
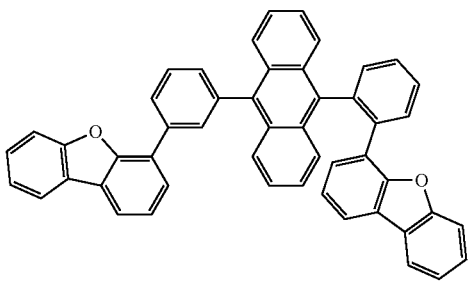
EM250
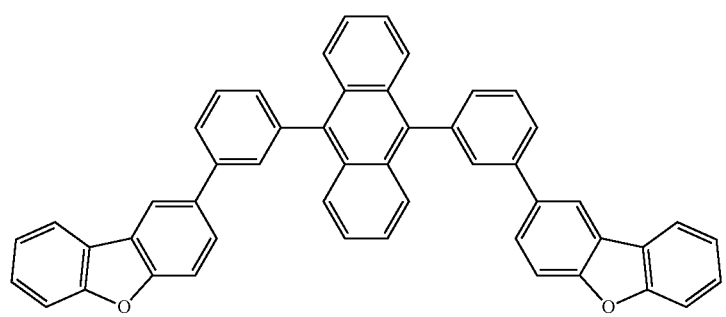
EM251
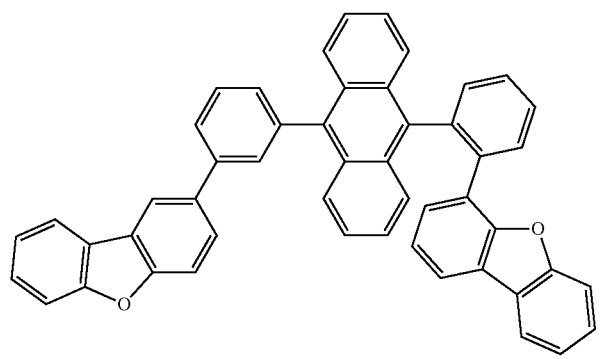
EM252
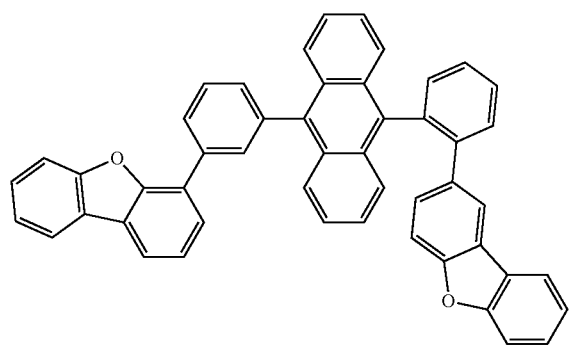
EM253
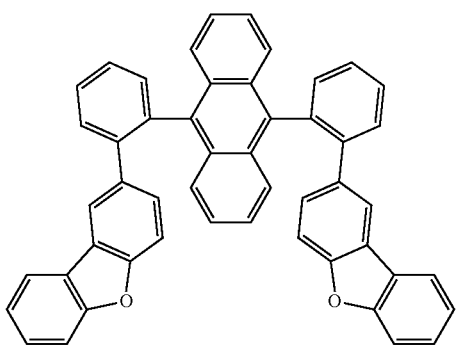

-continued
EM254
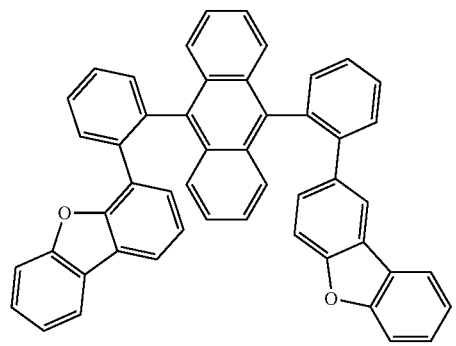
EM255
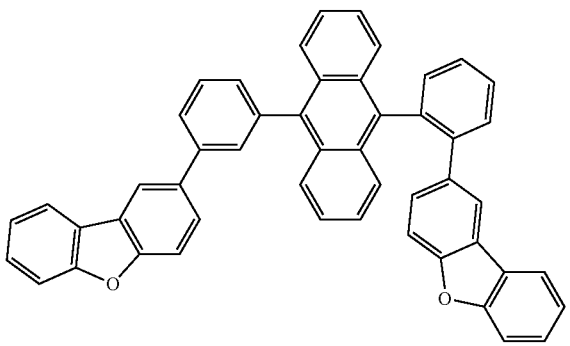
EM256
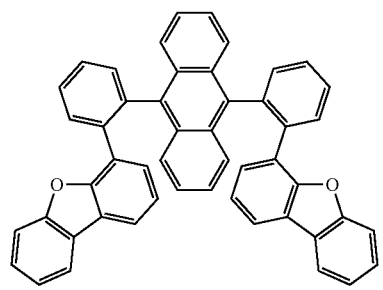
EM257
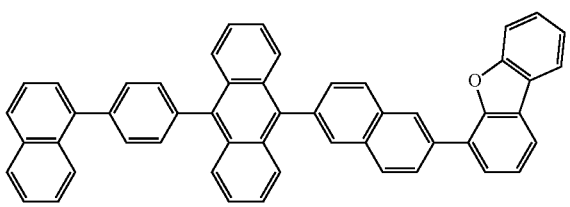
EM258
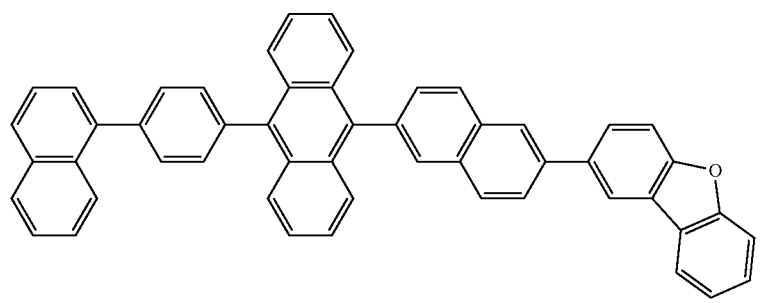
EM259
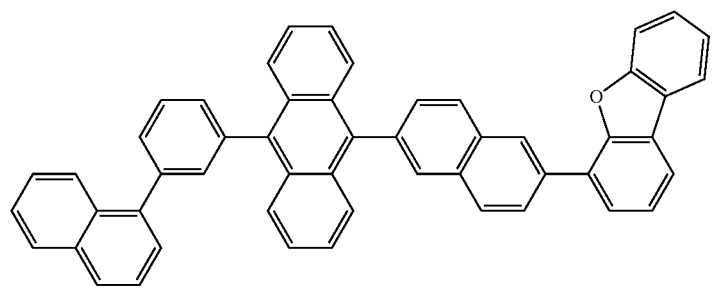
EM260
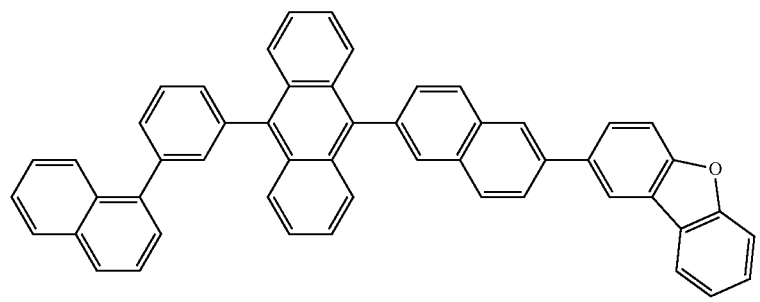

-continued
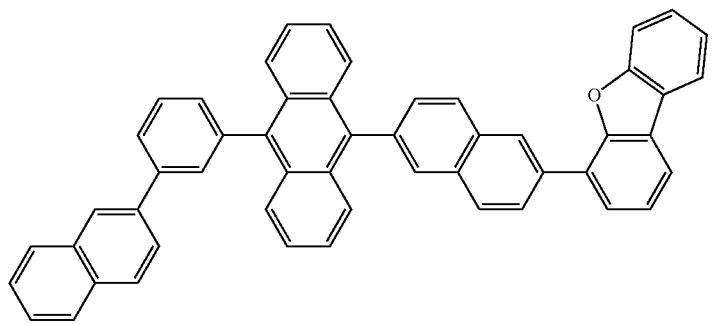
EM261
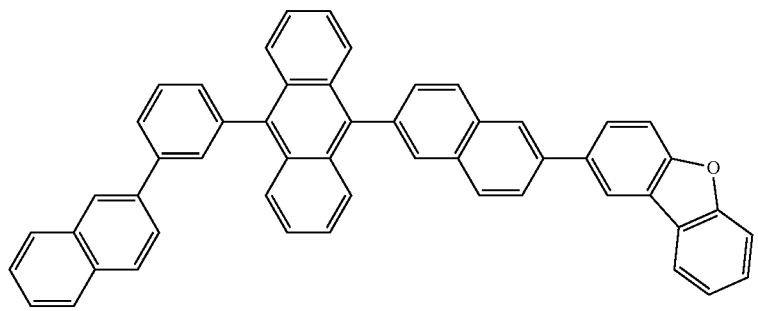
EM262
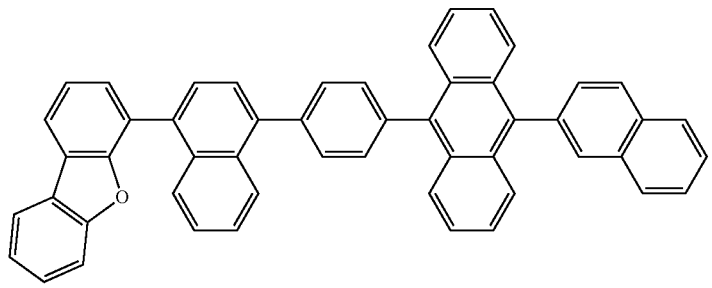
EM263
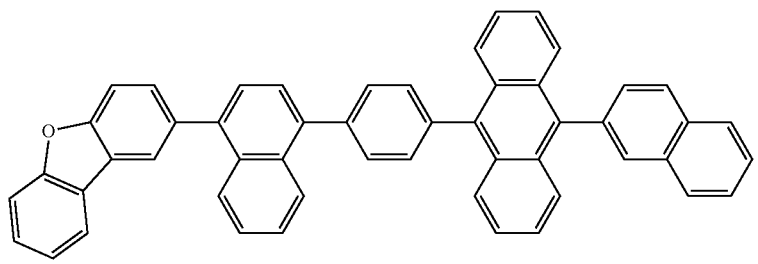
EM264
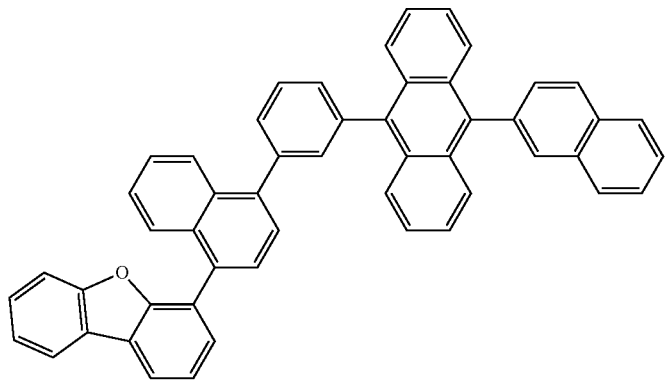
EM265

-continued
EM266
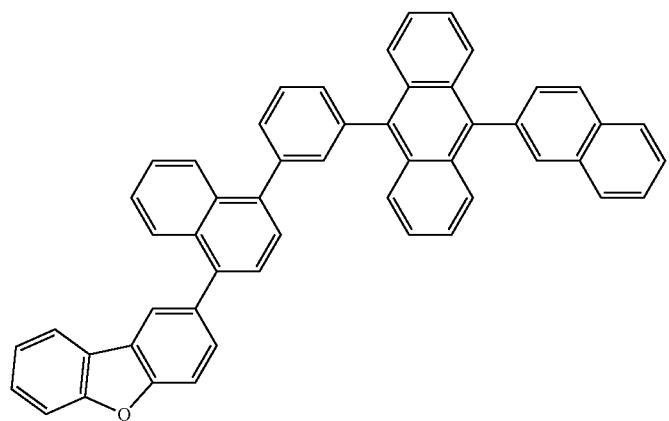
EM267
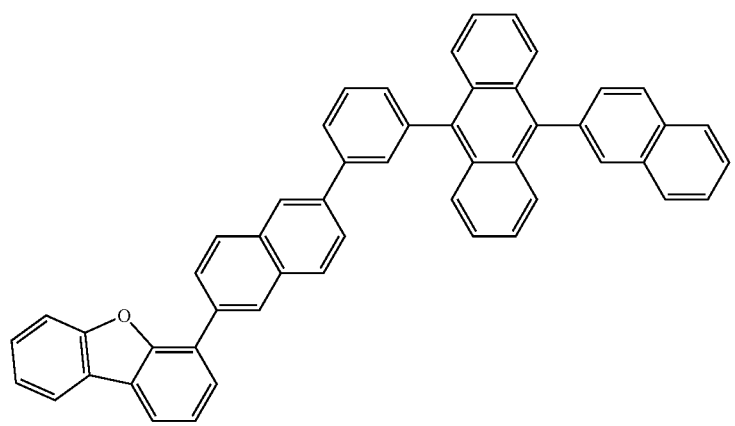
EM268
EM269
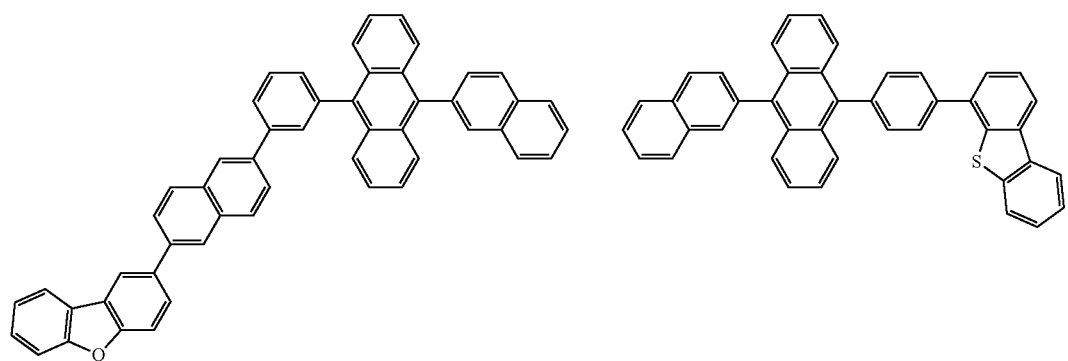
EM270
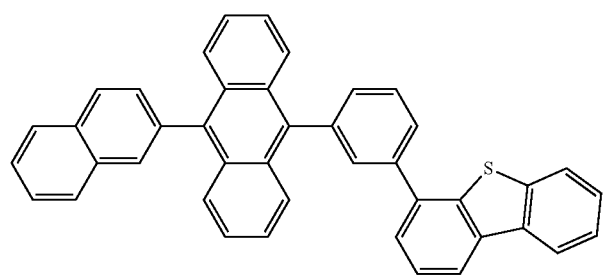

EM271
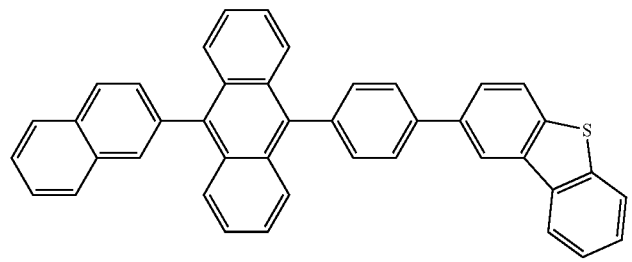
EM272
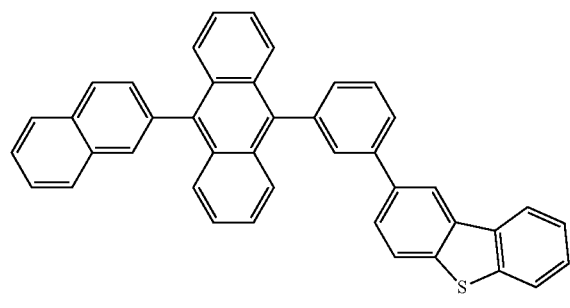
EM273
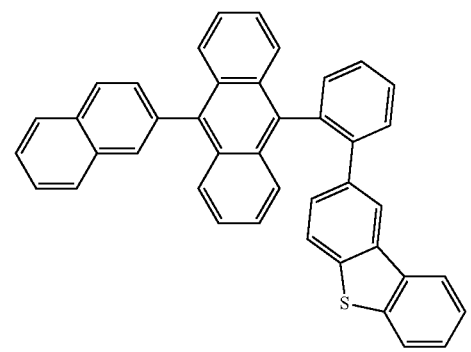
EM274
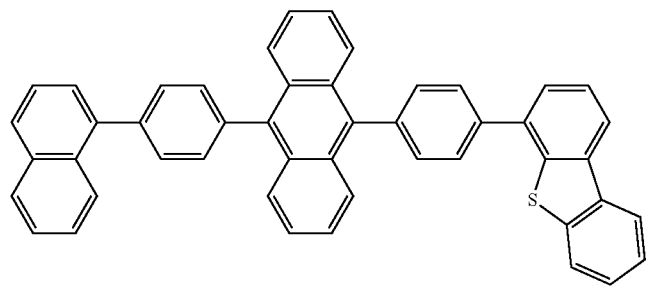
EM275
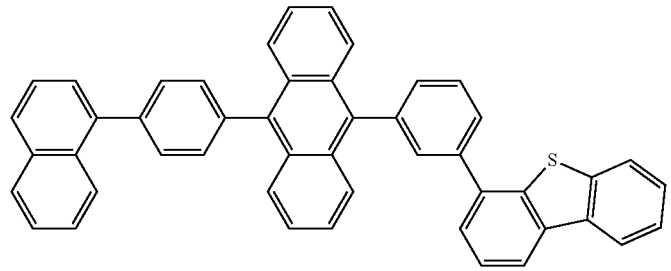
EM276
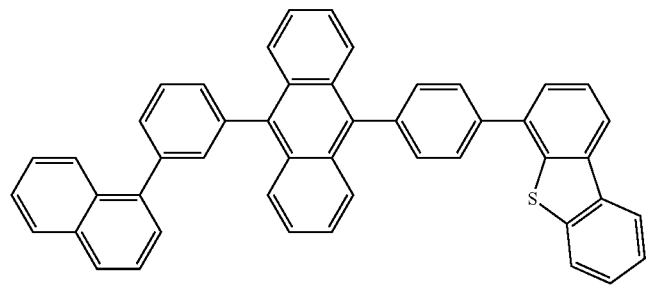

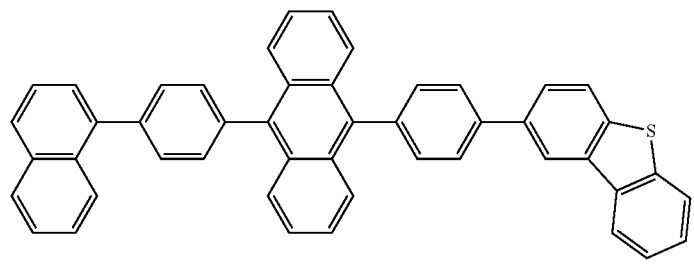
EM277
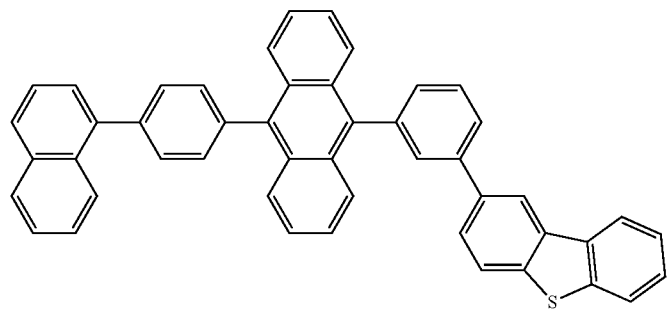
EM278
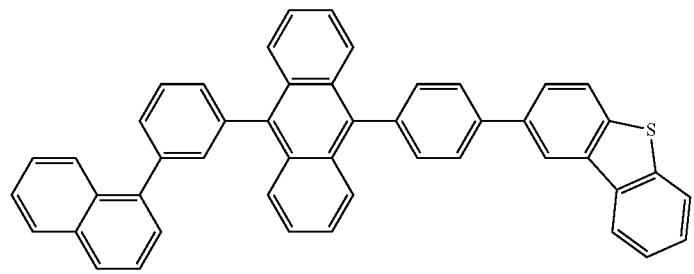
EM279
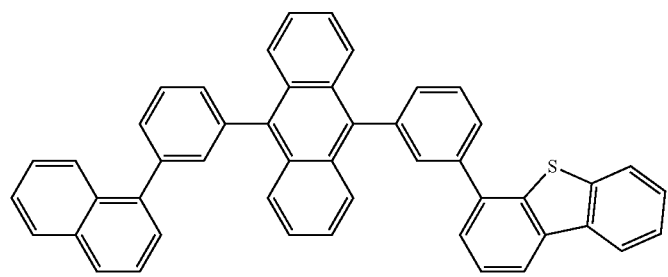
EM280
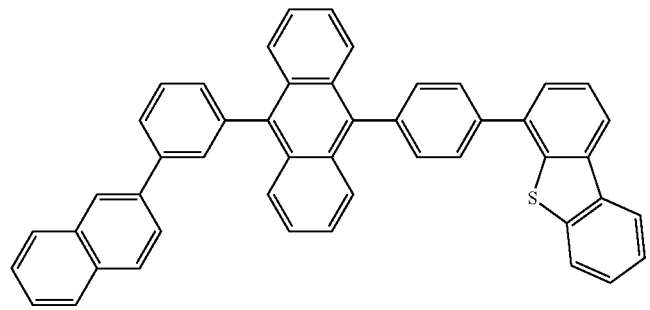
EM281

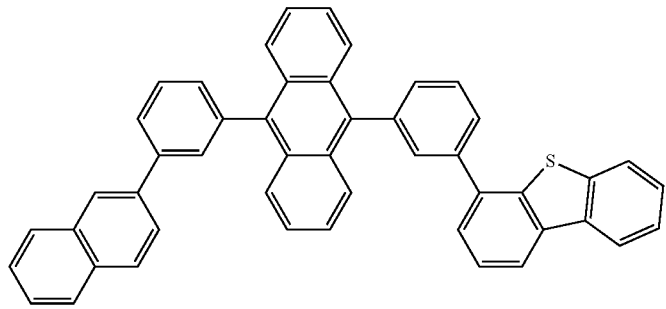
EM282
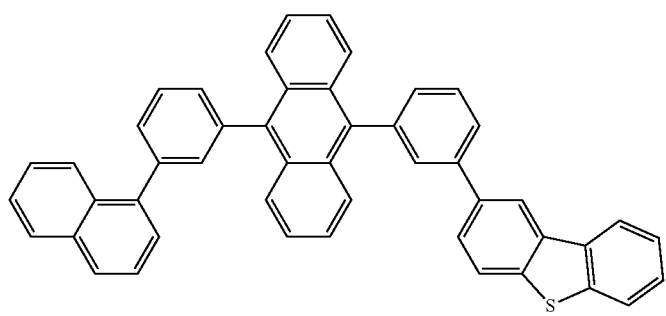
EM283
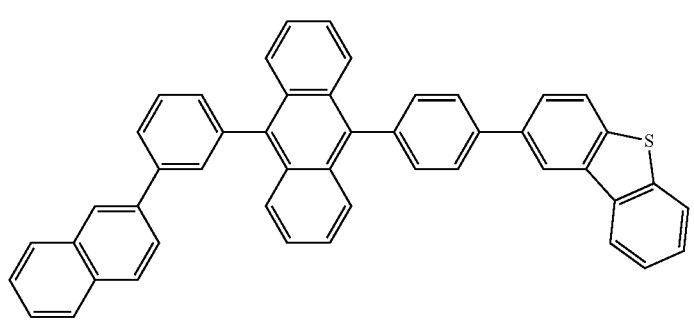
EM284
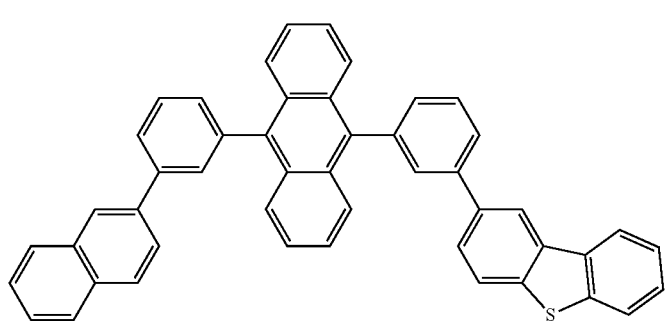
EM285

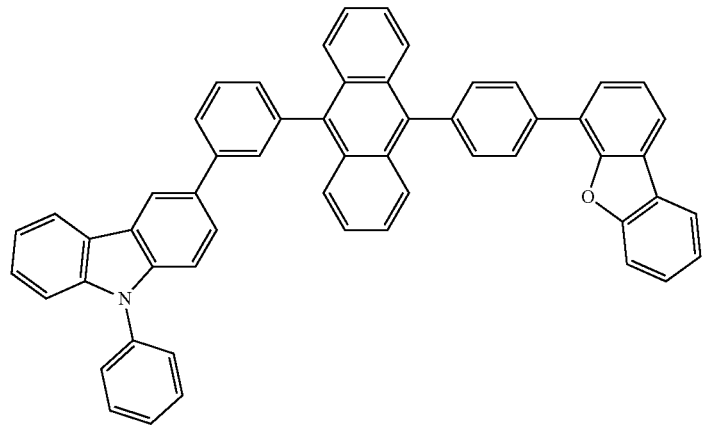
EM286
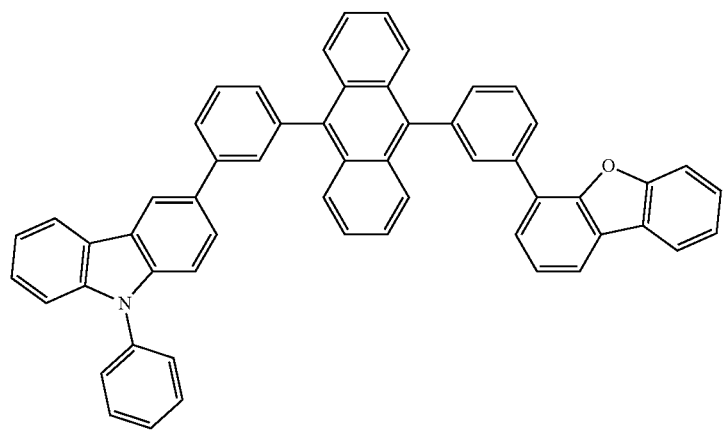
EM287
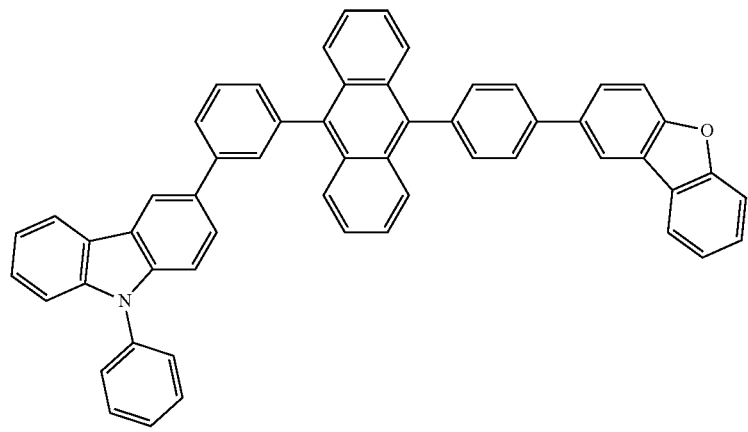
EM288

-continued
EM289
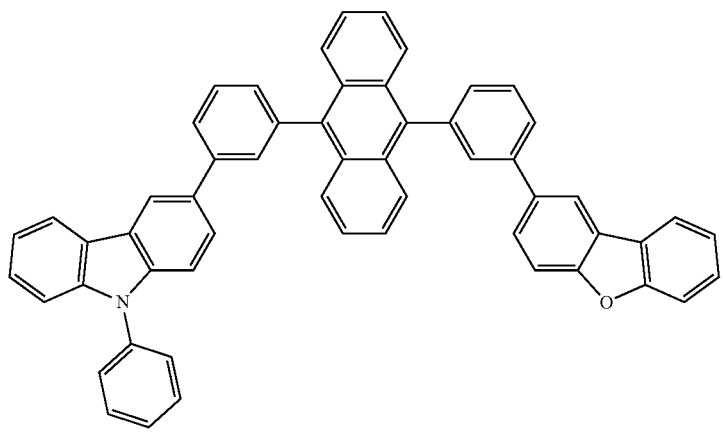
EM290
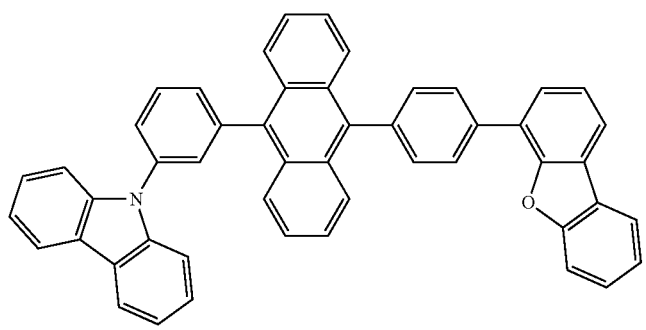
EM291
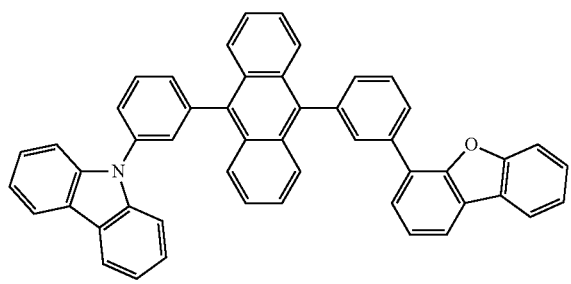
EM292
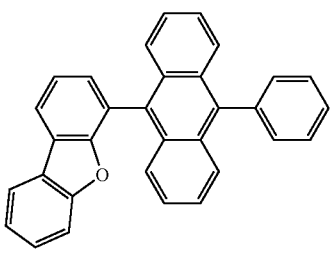
EM293
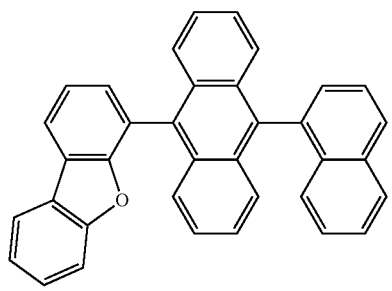
EM294
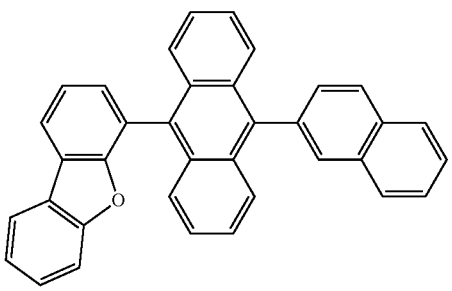
EM295
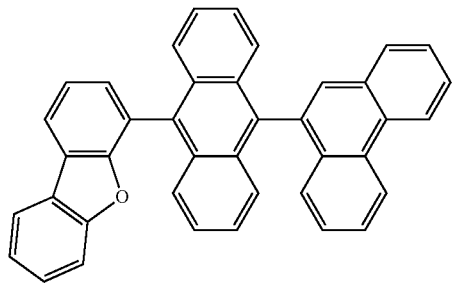
EM296
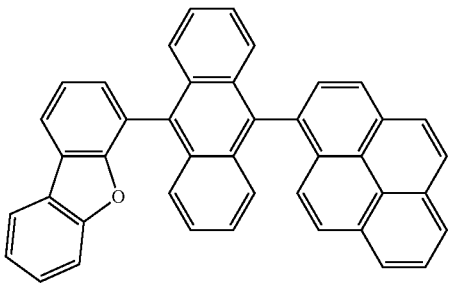

-continued
EM297
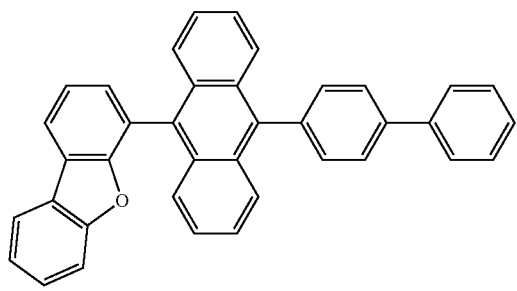
EM298
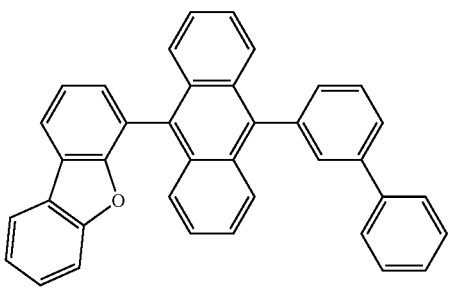
EM299
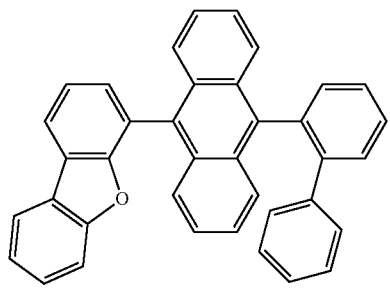
EM300
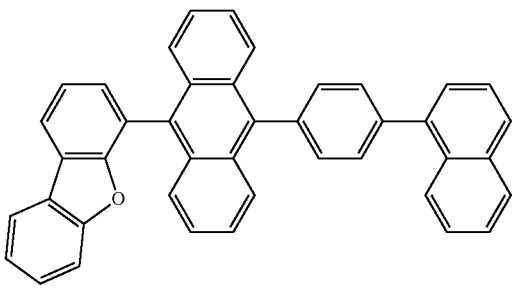
EM301
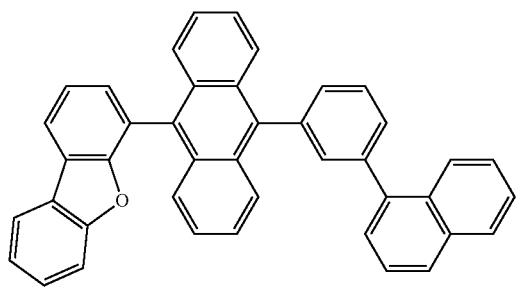
EM302
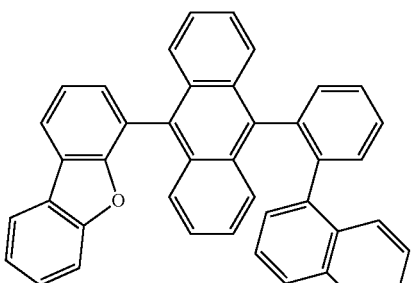
EM303
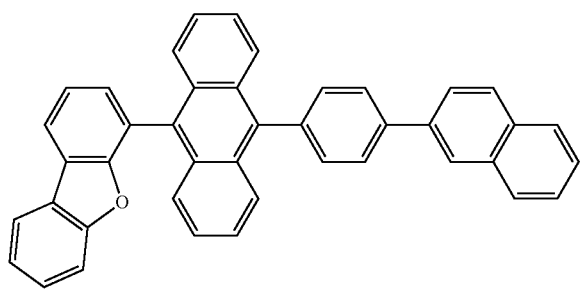
EM304
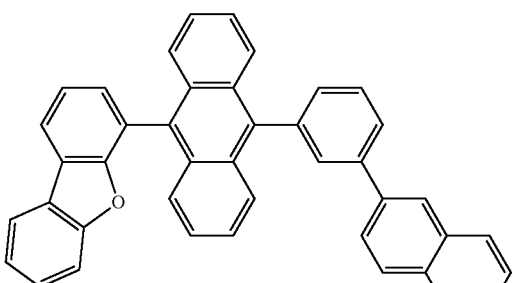
EM305
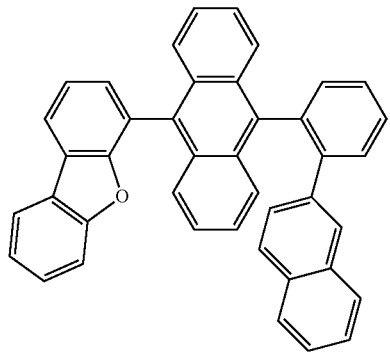
EM306
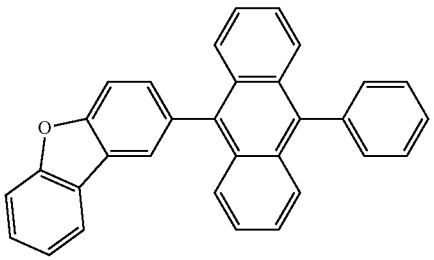

-continued
EM307
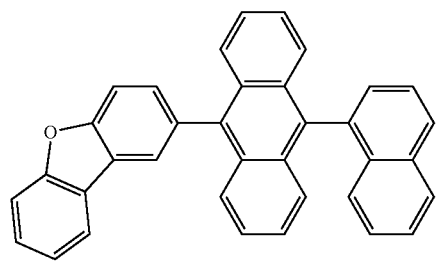
EM308
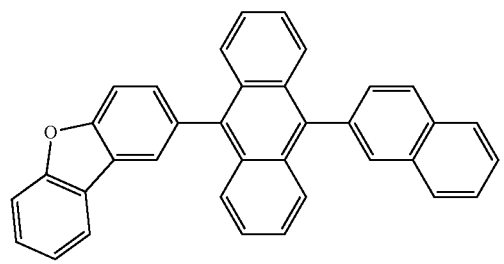
EM309
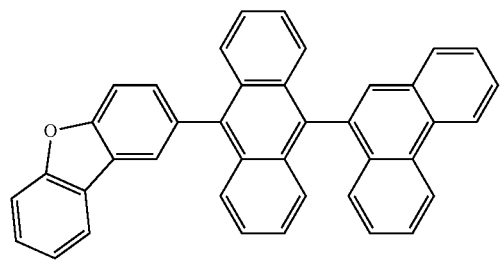
EM310
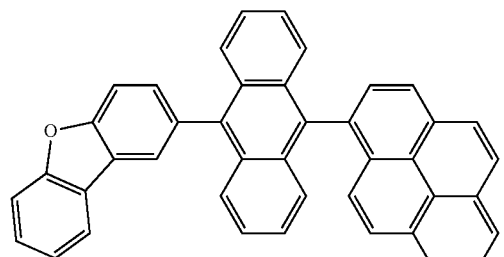
EM311
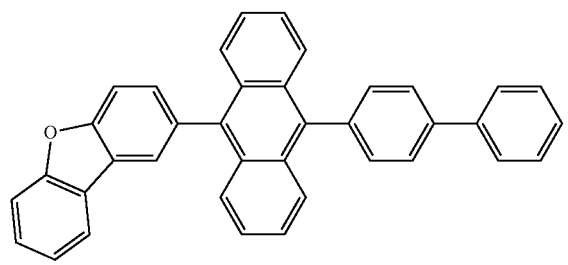
EM312
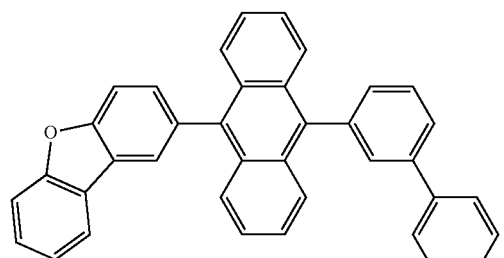
EM313
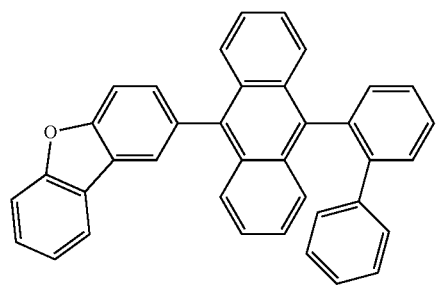
EM314
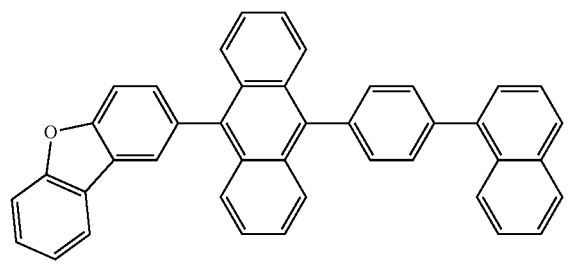
EM315
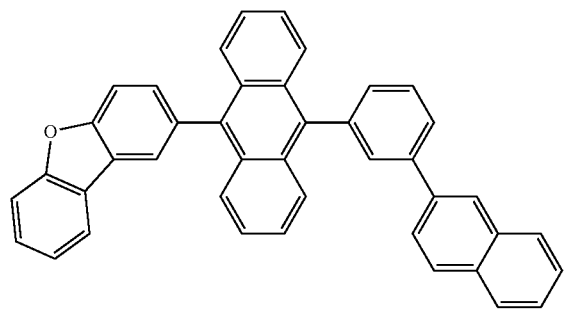
EM316
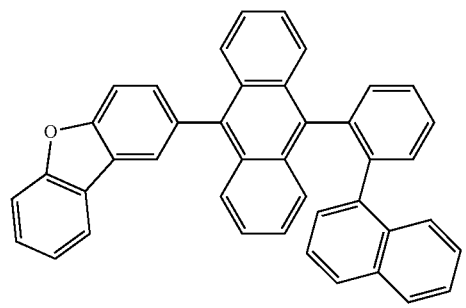

-continued
EM317
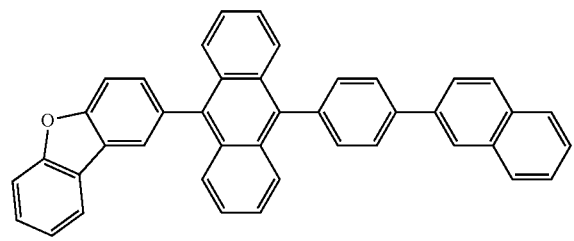
EM318
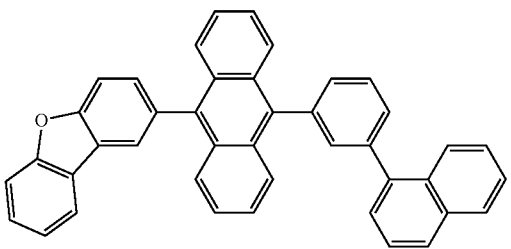
EM319
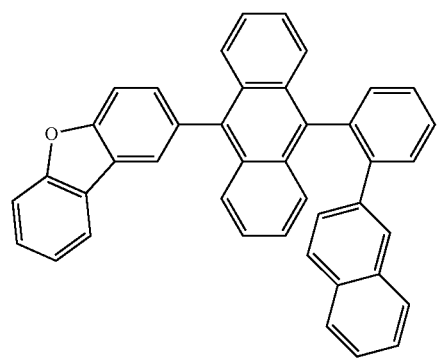
EM320
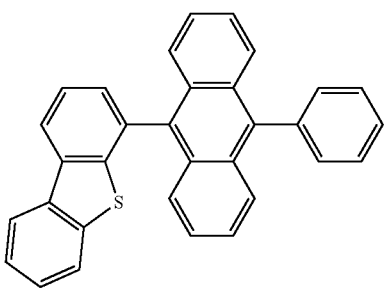
EM321
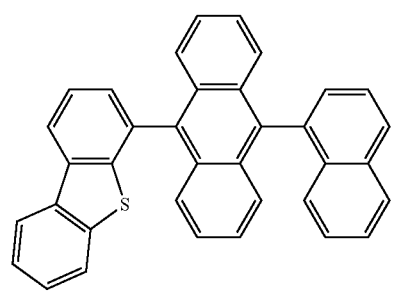
EM322
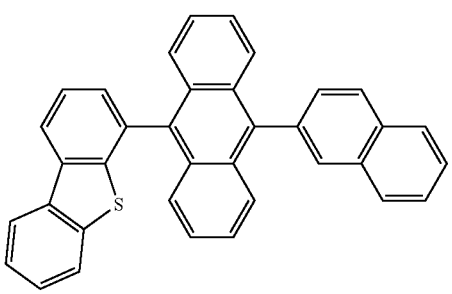
EM323
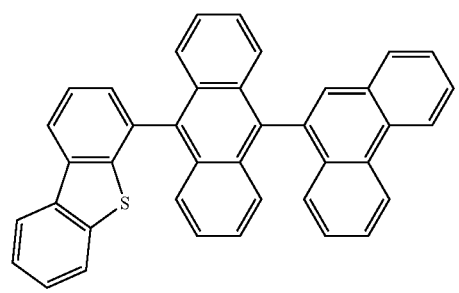
EM324
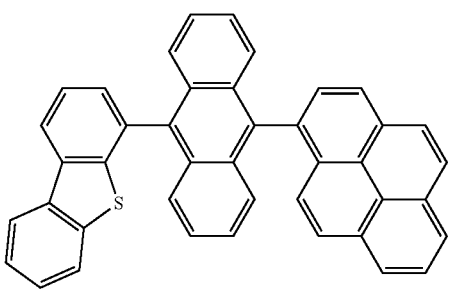
EM325
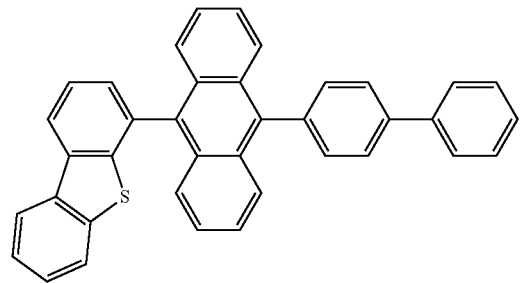
EM326
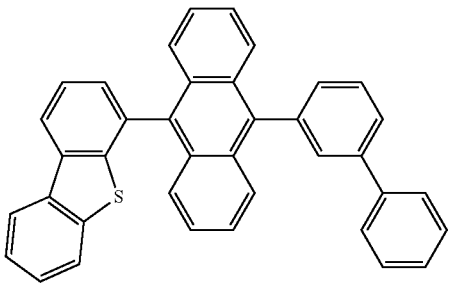

-continued
EM327
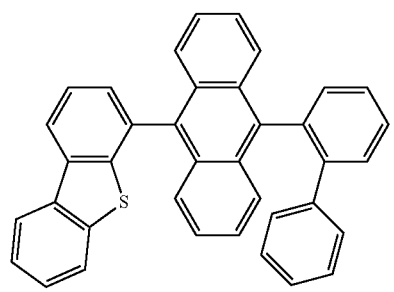
EM328
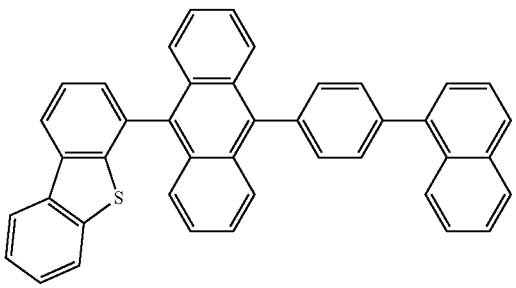
EM329
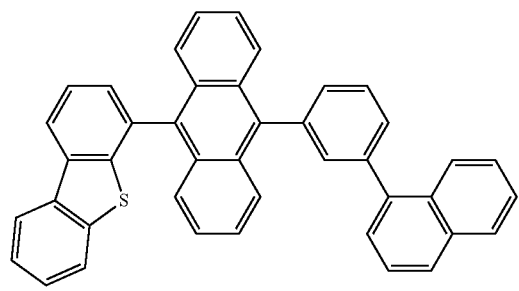
EM330
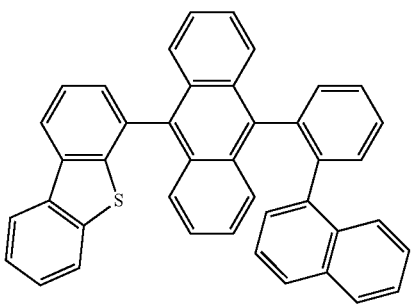
EM331
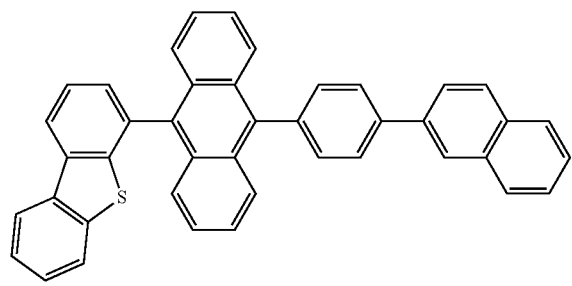
EM332
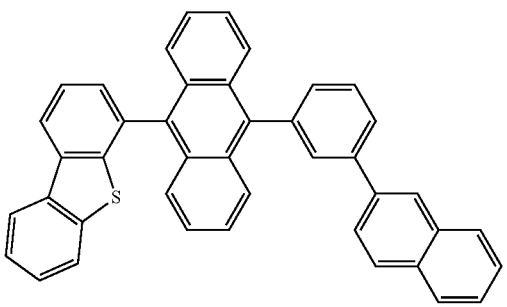
EM333
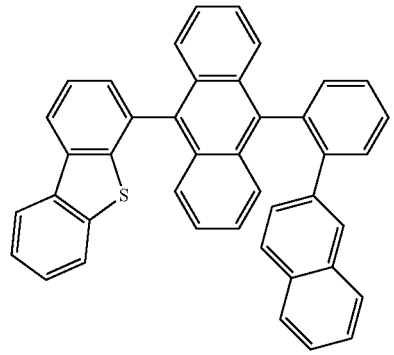
EM334
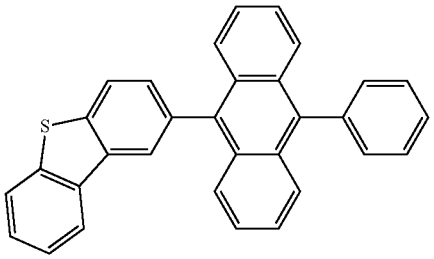
EM335
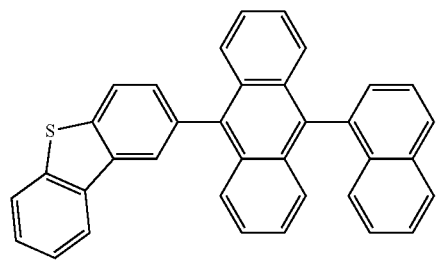
EM336
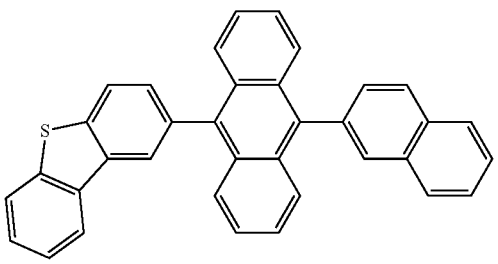

EM337
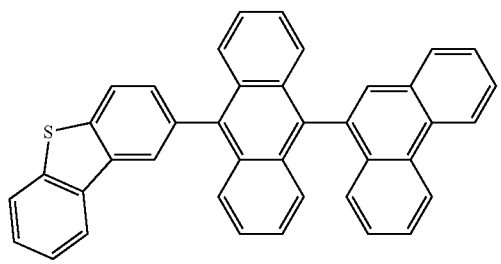
EM338
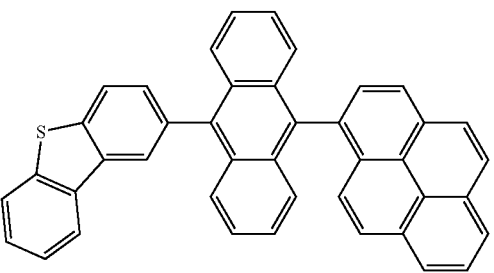
EM339
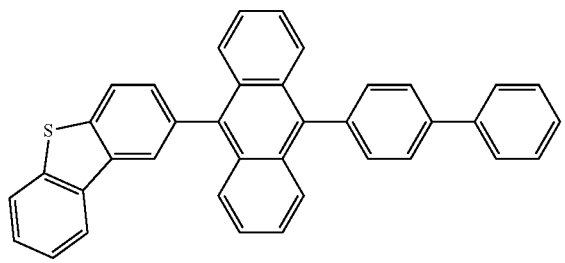
EM340
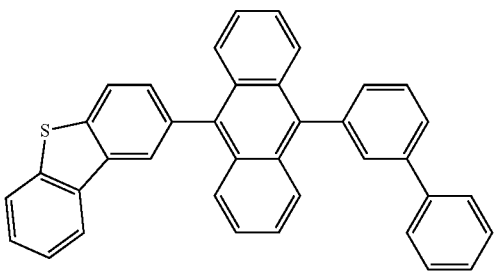
EM341
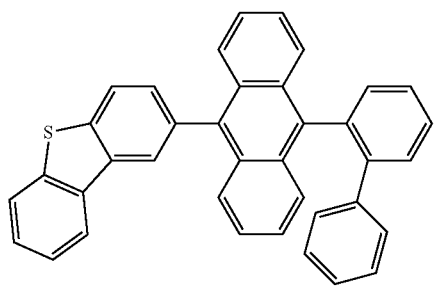
EM342
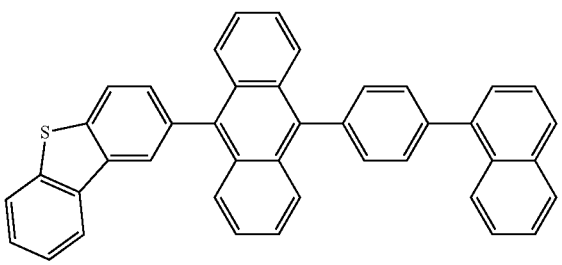
EM343
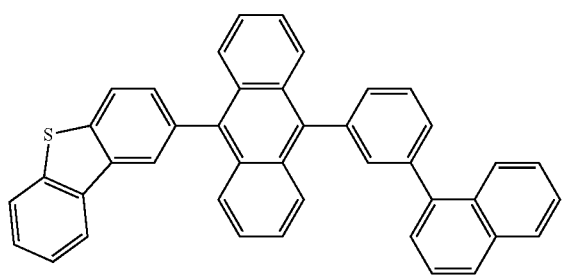
EM344
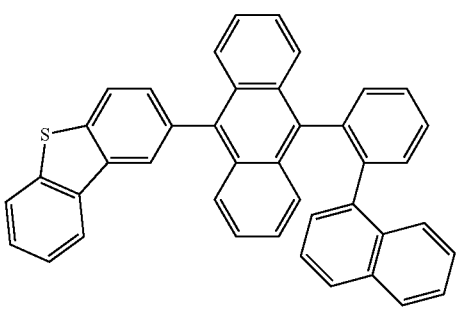
EM345
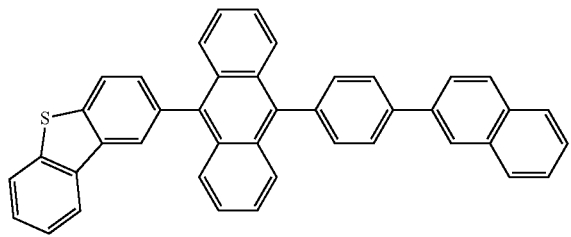
EM346
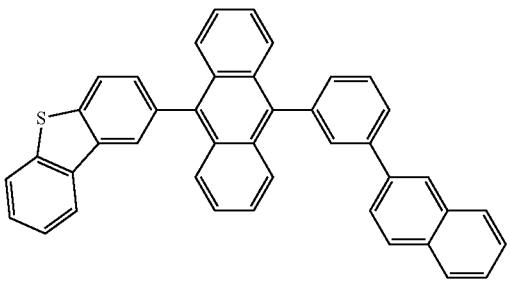

-continued
EM347
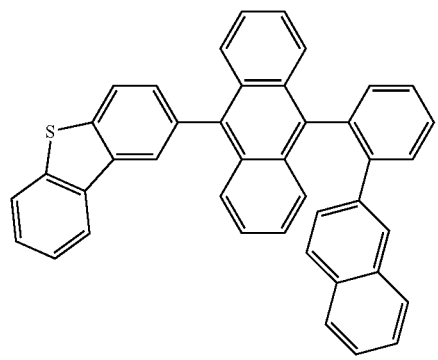
EM348
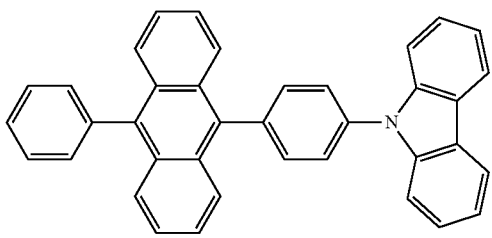
EM349
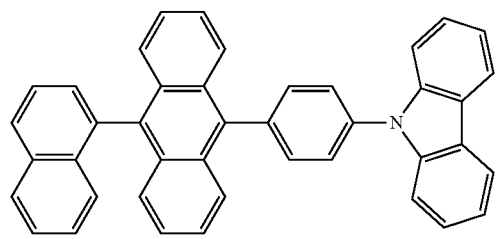
EM350
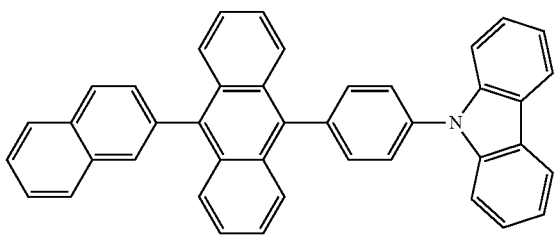
EM351
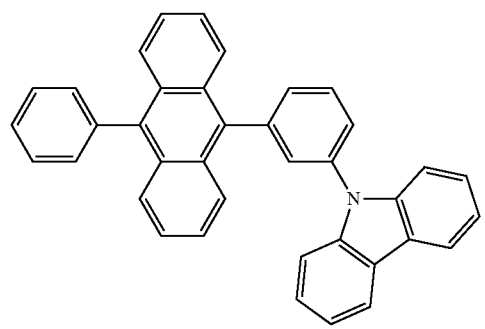
EM352
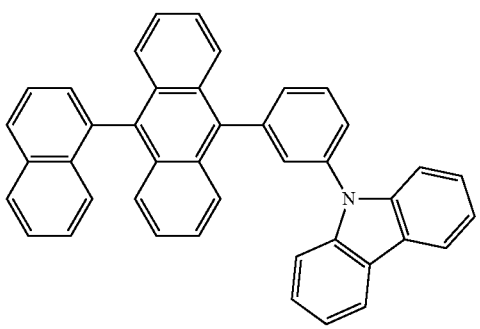
EM353
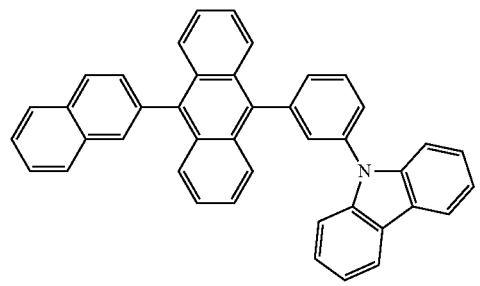
EM354
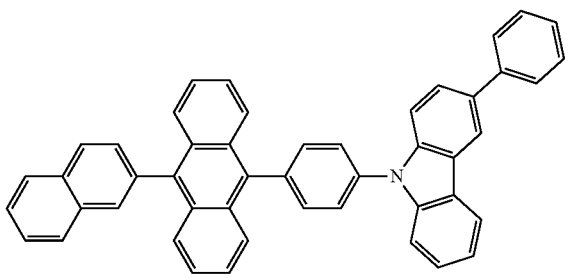
EM355
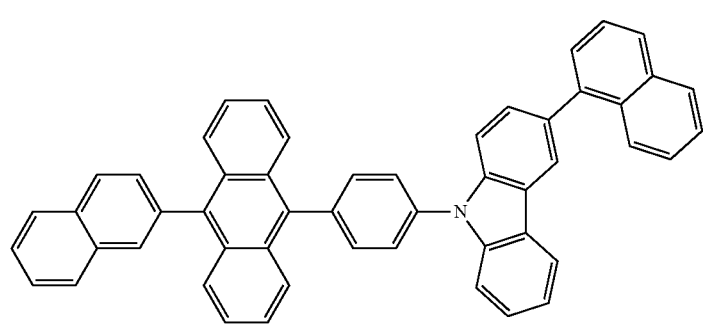

-continued
EM356
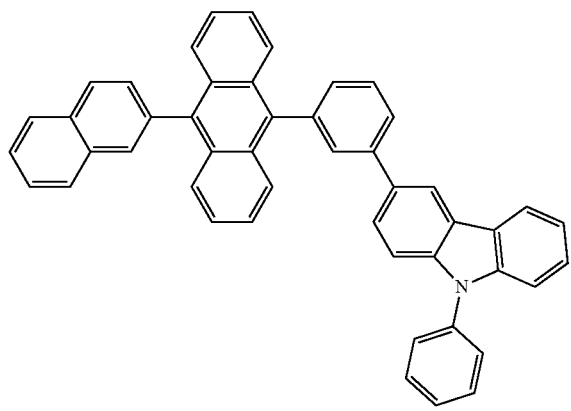
EM357
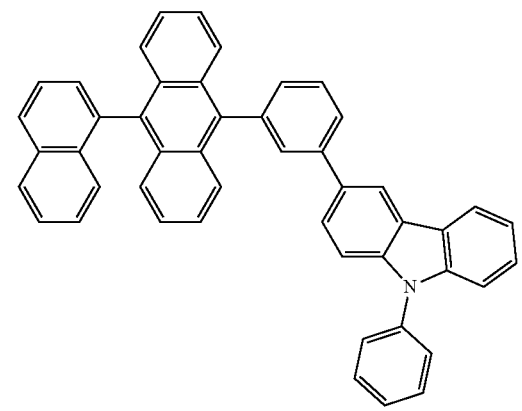
EM358
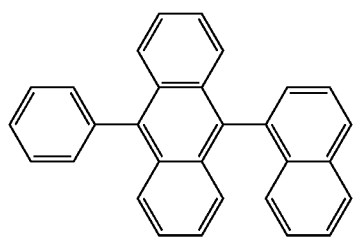
EM359
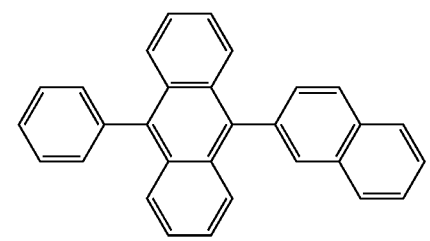
EM360
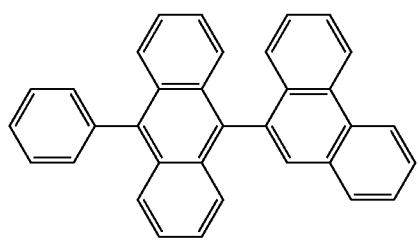
EM361
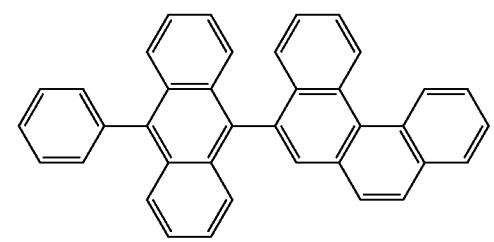
EM362
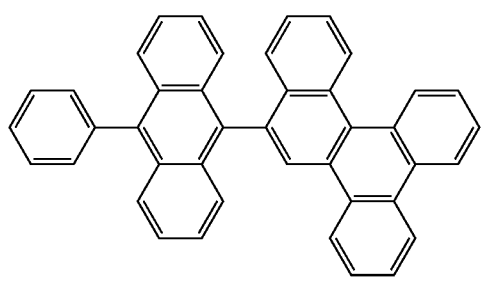
EM363
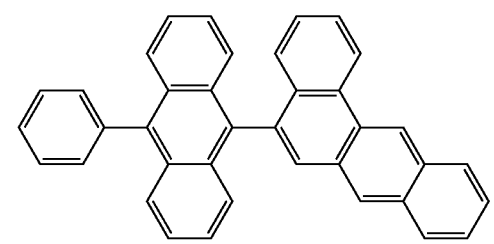
EM364
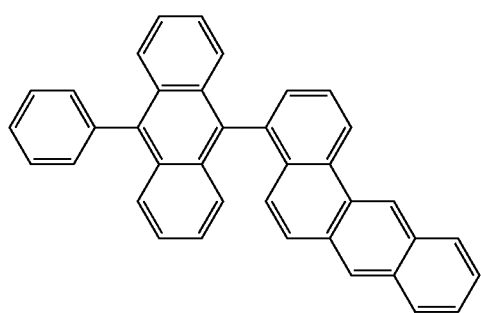
EM365
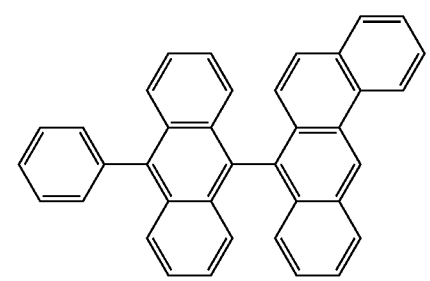

EM366
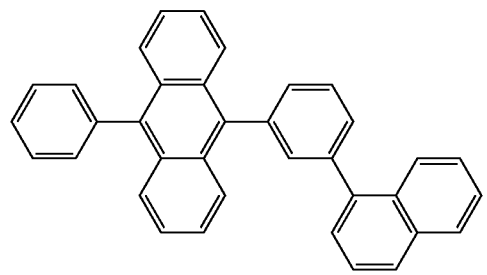
EM367
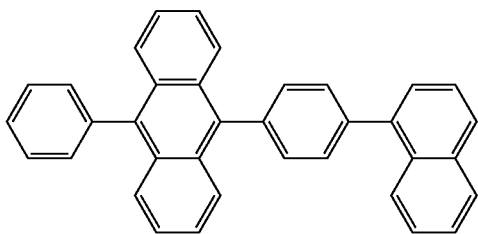
EM368
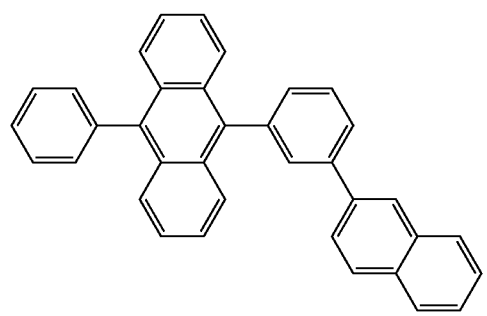
EM369
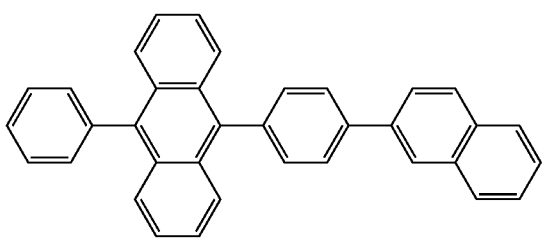
EM370
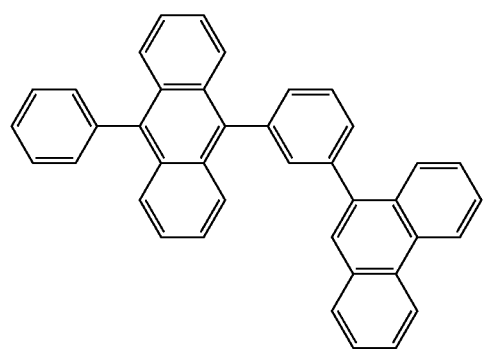
EM371
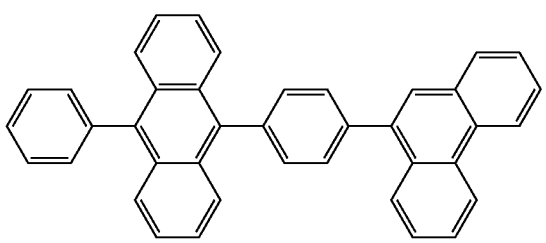
EM373
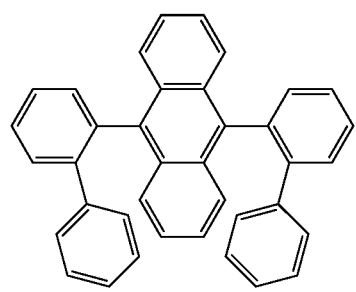
EM374
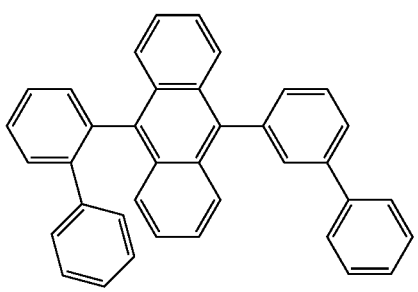

-continued
EM375
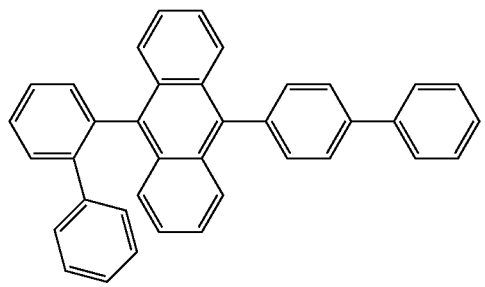
EM376
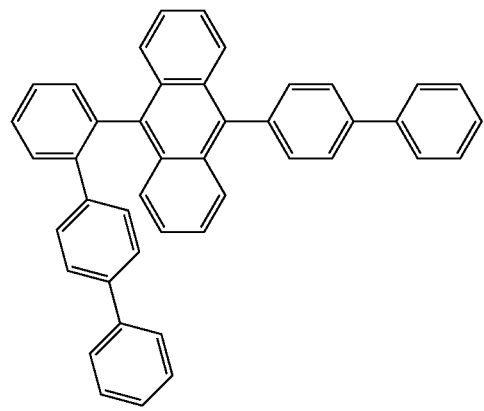
EM377
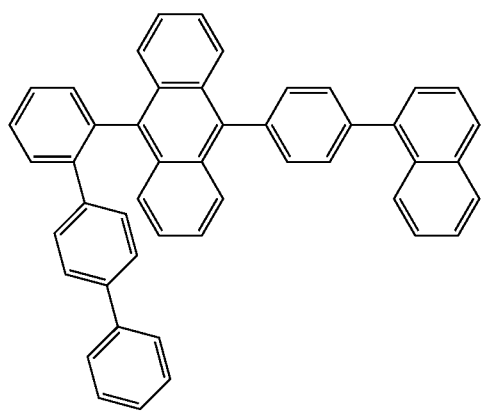
EM378
EM379
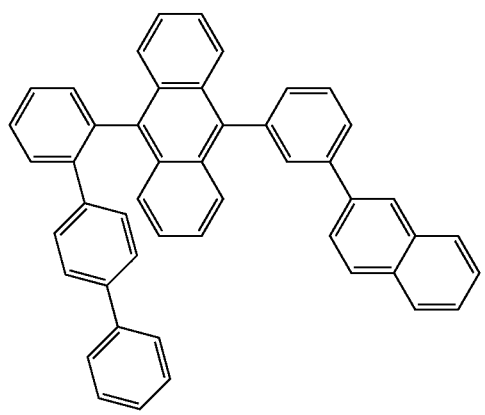
EM380
EM381
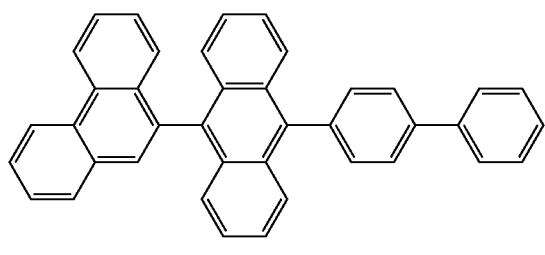
EM382
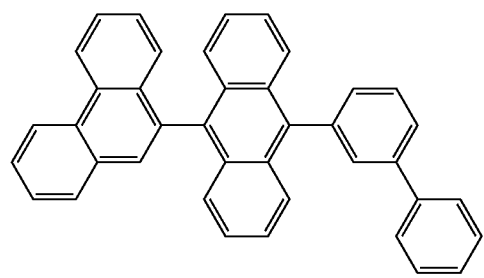

-continued
EM383
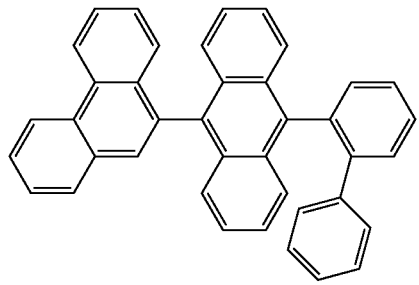
EM384
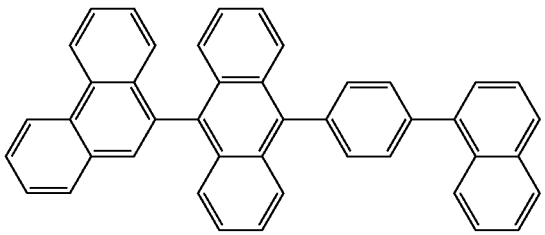
EM385
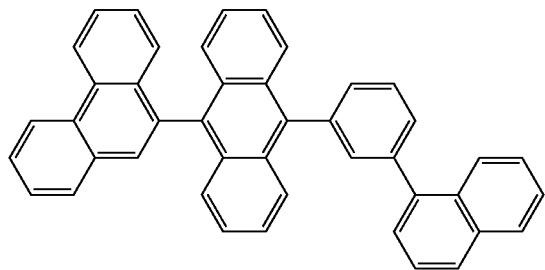
EM386
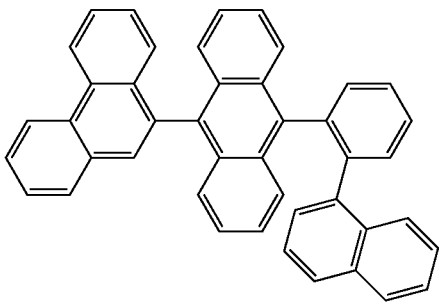
EM387
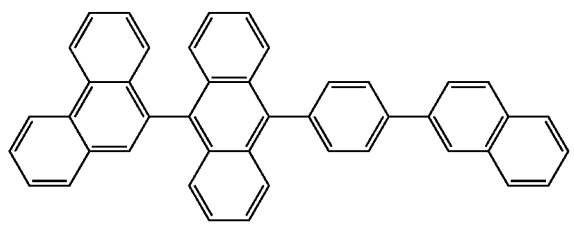
EM388
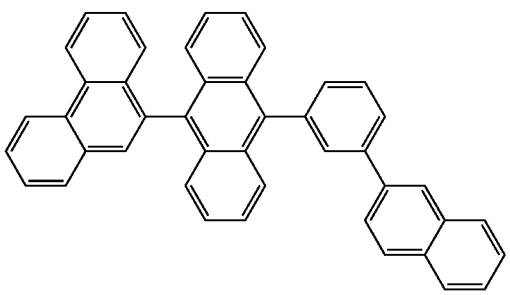
EM389
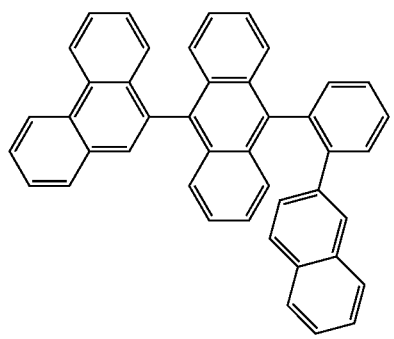
EM390
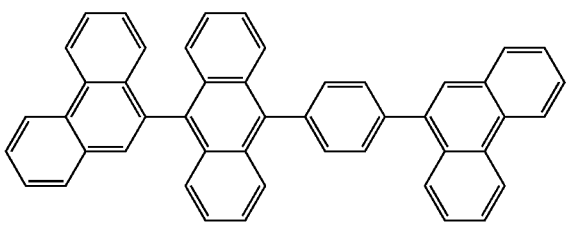

-continued

EM391

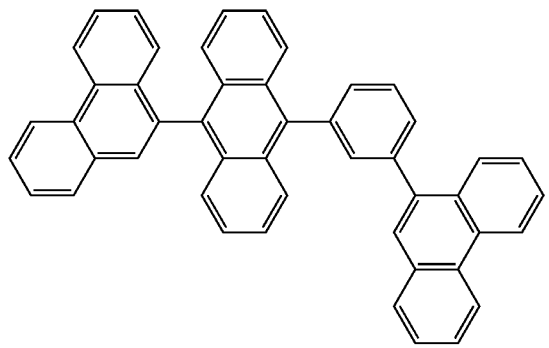

EM392

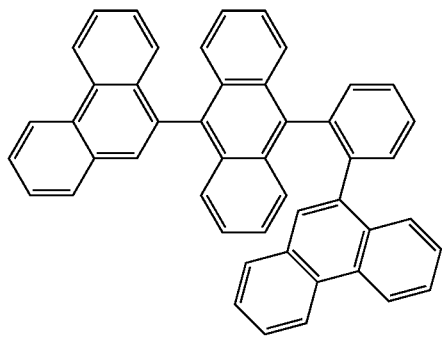

In the invention, as the organic EL device in which the organic thin film layer is composed of plural layers, one in which an anode, a hole-injecting layer, an emitting layer and a cathode are sequentially stacked (anode/hole-injecting layer/emitting layer/cathode), one in which an anode, an emitting layer, an electron-injecting layer and a cathode are sequentially stacked (anode/emitting layer/electron-injecting layer/cathode), one in which an anode, a hole-injecting layer, an emitting layer, an electron-injecting layer and a cathode are sequentially stacked (anode/hole-injecting layer/emitting layer/electron-injecting layer/cathode), one in which an anode, a hole-injecting layer, a hole-transporting layer, an emitting layer, an electron-injecting layer and a cathode are sequentially stacked (anode/hole-injecting layer/hole-transporting layer/emitting layer/electron-injecting layer/cathode) or the like can be given.

By allowing the organic thin film layer to be composed of plural layers, the organic EL device can be prevented from lowering of luminance or lifetime due to quenching. If necessary, an emitting material, a doping material, a hole-injecting material or an electron-injecting material can be used in combination. Further, due to the use of a doping material, luminance or luminous efficiency may be improved. The hole-injecting layer, the emitting layer and the electron-injecting layer may respectively be formed of two or more layers. In such a case, in the hole-injecting layer, a layer which injects holes from an electrode is referred to as a hole-injecting layer, and a layer which receives holes from the hole-injecting layer and transports the holes to the emitting layer is referred to as a hole-transporting layer. Similarly, in the electron-injecting layer, a layer which injects electrons from an electrode is referred to as an electron-injecting layer and a layer which receives electrons from an electron-injecting layer and transports the electrons to the emitting layer is referred to as an electron-transporting layer. Each of these layers is selected and used according to each of the factors of a material, i.e. the energy level, heat resistance, adhesiveness to the organic layer or the metal electrode or the like.

Examples of the host material and the doping material other than those represented by the above-mentioned formula (2A) which can be used in the emitting layer together with the aromatic amine derivative of the invention include, though not limited thereto, fused polycyclic aromatic compounds such as naphthalene, phenanthrene, rubrene, anthracene, tetracene, pyrene, perylene, chrysene, decacyclene, coronene, tetraphenylcyclopentadiene, pentaphenylcyclopentadiene, fluorene, spirofluorene and derivatives thereof, organic metal complexes such as tris(8-quinolinolate)aluminum, triarylamine derivatives, styrylamine derivatives, stilbene derivatives, coumarin derivatives, pyrane derivatives, oxazone derivatives, benzothiazole derivatives, benzoxazole derivatives, benzimidazole derivatives, pyrazine derivatives, cinnamate derivatives, diketo-pyrrolo-pyrrole derivatives, acridone derivatives and quinacridone derivatives.

As the hole-injecting material, a compound which can transport holes, exhibits hole-injecting effects from the anode and excellent hole-injection effect for the emitting layer or the emitting material, and has an excellent capability of forming a thin film is preferable. Specific examples thereof include, though not limited thereto, phthalocyanine derivatives, naphthalocyanine derivatives, porphyline derivatives, benzidine-type triphenylamine, diamine-type triphenylamine, hexacyanohexaazatriphenylene, derivatives thereof, and polymer materials such as polyvinylcarbazole, polysilane and conductive polymers.

Of the hole-injecting materials usable in the organic EL device of the invention, further effective hole-injecting materials are phthalocyanine derivatives.

Examples of the phthalocyanine (Pc) derivative include, though not limited thereto, phthalocyanine derivatives and naphthalocyanine derivatives such as $H_2Pc$, CuPc, CoPc, NiPc, ZnPc, PdPc, FePc, MnPc, ClAlPc, ClGaPc, ClInPc, ClSnPc, $Cl_2SiPc$, (HO)AlPc, (HO)GaPc, VOPc, TiOPc, MoOPc and GaPc-O—GaPc.

In addition, it is also possible to sensitize carriers by adding to the hole-injecting material an electron-accepting substance such as a TCNQ derivative.

Preferable hole-transporting materials usable in the organic EL device of the invention are aromatic tertiary amine derivatives.

Examples of the aromatic tertiary amine derivative include, though not limited thereto, N,N'-diphenyl-N,N'-dinaphthyl-1,1'-biphenyl-4,4'-diamine, N,N,N',N'-tetrabiphenyl-1,1'-biphenyl-4,4'-diamine or an oligomer or a polymer having these aromatic tertiary amine skeleton.

As the electron-injecting material, a compound which can transport electrons, exhibits electron-injecting effects from the cathode and excellent electron-injection effect for the emitting layer or the emitting material, and has an excellent capability of forming a thin film is preferable.

In the organic EL device of the invention, further effective electron-injecting materials are a metal complex compound and a nitrogen-containing heterocyclic derivative.

Examples of the metal complex compound include, though not limited thereto, 8-hydroxyquinolinate lithium, bis(8-hydroxyquinolinate)zinc, tris(8-hydroxyquinolinate)aluminum, tris(8-hydroxyquinolinate)gallium, bis(10-hydroxybenzo[h]quinolinate)beryllium and bis(10-hydroxybenzo[h]quinolinate)zinc.

As examples of the nitrogen-containing heterocyclic derivative, oxazole, thiazole, oxadiazole, thiadiazole, triazole, pyridine, pyrimidine, triazine, phenanthroline, benzimidazole, imidazopyridine or the like are preferable, for example. Of these, a benzimidazole derivative, a phenanthroline derivative and an imiclazopyridine derivative are prereable.

As a preferred mode, a dopant is further contained in these electron-injecting materials, and in order to facilitate receiving electrons from the cathode, it is further preferable to dope the vicinity of the cathode interface of the second organic layer with a dopant, the representative example of which is an alkali metal.

As the dopant, a donating metal, a donating metal compound and a donating metal complex can be given. These reducing dopants may be used singly or in combination of two or more.

In the organic EL device of the invention, the emitting layer may contain, in addition to at least one of the above-mentioned aromatic amine derivatives represented by the formula (1), at least one of an emitting material, a doping material, a hole-injecting material, a hole-transporting material and an electron-injecting material in the same layer. Moreover, for improving stability of the organic EL device obtained by the invention to temperature, humidity, atmosphere, etc. it is also possible to prepare a protective layer on the surface of the device, and it is also possible to protect the entire device by applying silicone oil, a resin, etc.

As the conductive material used in the anode of the organic EL device of the invention, a conductive material having a work function of more than 4 eV is suitable. Carbon, aluminum, vanadium, iron, cobalt, nickel, tungsten, silver, gold, platinum, palladium or the like, alloys thereof, oxidized metals which are used in an ITO substrate and a NESA substrate such as tin oxide and indium oxide and organic conductive resins such as polythiophene and polypyrrole are used. As the conductive material used in the cathode, a conductive material having a work function of smaller than 4 eV is suitable. Magnesium, calcium, tin, lead, titanium, yttrium, lithium, ruthenium, manganese, aluminum, and lithium fluoride or the like, and alloys thereof are used, but not limited thereto. Representative examples of the alloys include, though not limited thereto, magnesium/silver alloys, magnesium/indium alloys and lithium/aluminum alloys. The amount ratio of the alloy is controlled by the temperature of the deposition source, atmosphere, vacuum degree or the like, and an appropriate ratio is selected. If necessary, the anode and the cathode each may be composed of two or more layers.

In the organic EL device of the invention, in order to allow it to emit light efficiently, it is preferred that at least one of the surfaces be fully transparent in the emission wavelength region of the device. In addition, it is preferred that the substrate also be transparent. The transparent electrode is set such that predetermined transparency can be ensured by a method such as deposition or sputtering by using the above-mentioned conductive materials. It is preferred that the electrode on the emitting surface have a light transmittance of 10% or more. Although no specific restrictions are imposed on the substrate as long as it has mechanical and thermal strength and transparency, a glass substrate and a transparent resin film can be given.

Each layer of the organic EL device of the invention can be formed by a dry film-forming method such as vacuum vapor deposition, sputtering, plasma ion coating, ion plating or the like or a wet film-forming method such as spin coating, dipping, flow coating or the like. Although the film thickness is not particularly limited, it is required to adjust the film thickness to an appropriate value. If the film thickness is too large, a large voltage is required to be applied in order to obtain a certain optical output, which results in a poor efficiency. If the film thickness is too small, pinholes or the like are generated, and a sufficient luminance cannot be obtained even if an electrical field is applied. The suitable film thickness is normally 5 nm to 10 μm, with a range of 10 nm to 0.2 μm being further preferable.

In the case of the wet film-forming method, a thin film is formed by dissolving or dispersing materials forming each layer in an appropriate solvent such as ethanol, chloroform, tetrahydrofuran and dioxane. Any of the above-mentioned solvents can be used.

As the solution suitable for such wet film-forming method, it is possible to use an organic EL material-containing solution which contains the aromatic amine derivative of the invention as an organic EL material and a solvent.

It is preferred that the above-mentioned organic EL material contain a host material and a dopant material, the dopant material be the aromatic amine derivative of the invention and the host material be at least one selected from compounds represented by the formula (2A).

In each organic thin film layer, an appropriate resin or additive may be used in order to improve film-forming properties, to prevent generation of pinholes in the film, or for other purposes.

The organic EL device of the invention can be suitably used as a planar emitting body such as a flat panel display of a wall-hanging television, backlight of a copier, a printer or a liquid crystal display, light sources for instruments, a display panel, a navigation light, or the like. The compound of the invention can be used not only in an organic EL device but also in the fields of an electrophotographic photoreceptor, a photoelectric converting element, a solar cell and an image sensor.

EXAMPLES

The invention will be explained hereinbelow with reference to Examples.

The host material and the doping material used in Examples and Comparative Examples are given below.

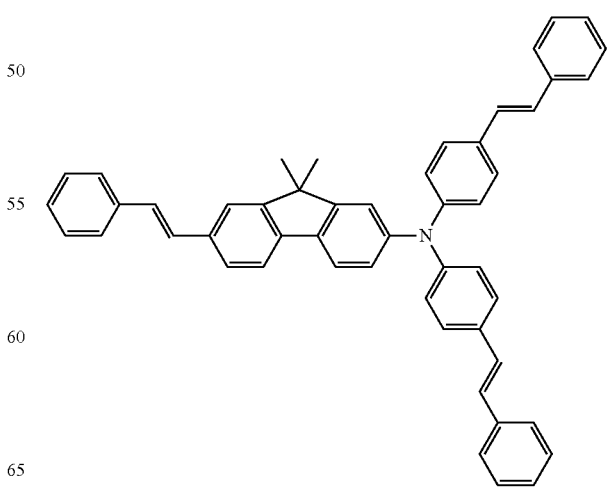

D-1

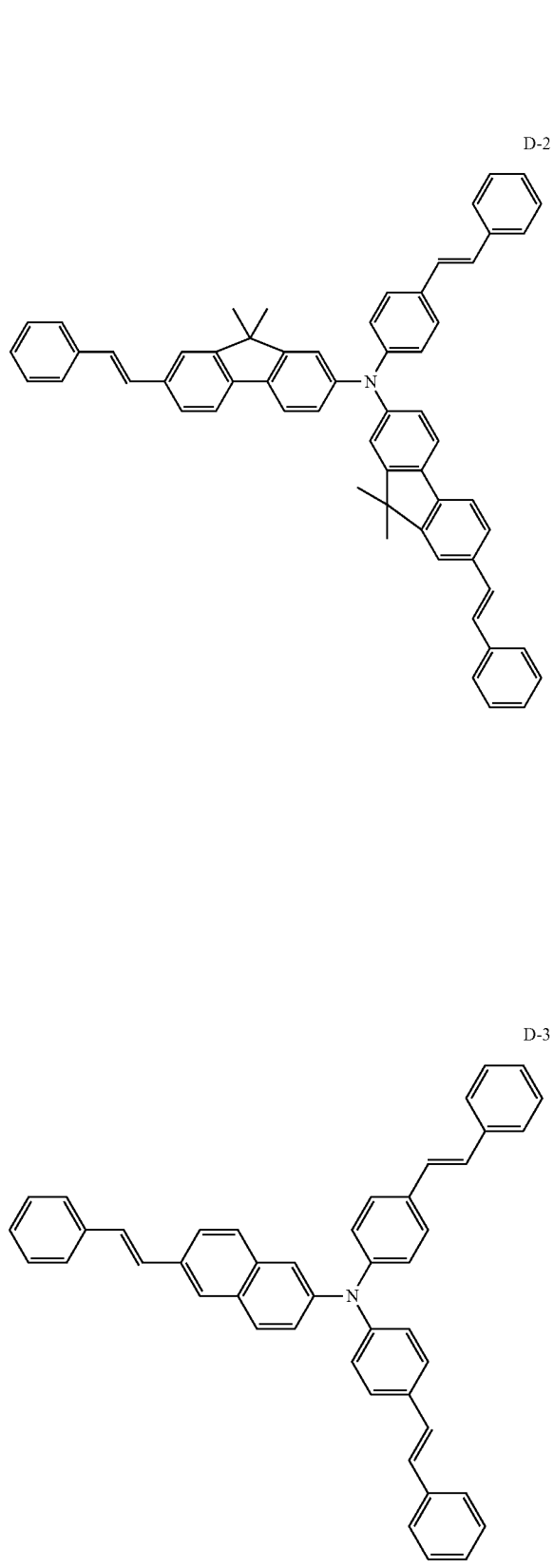
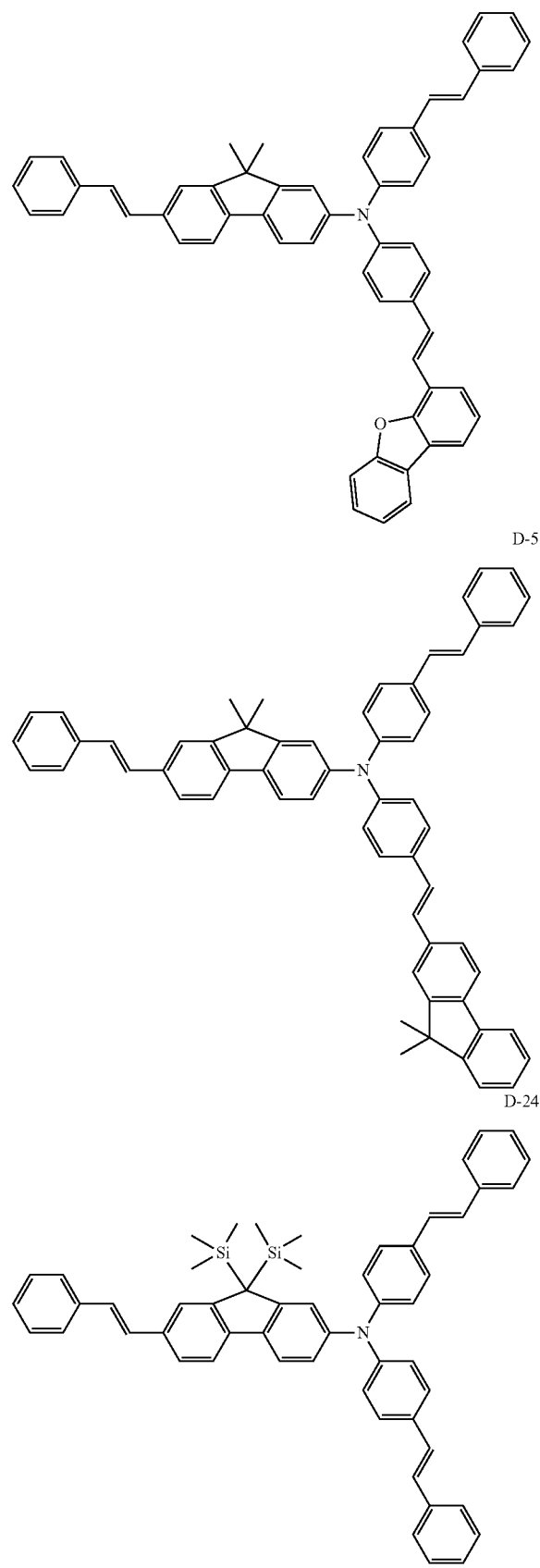

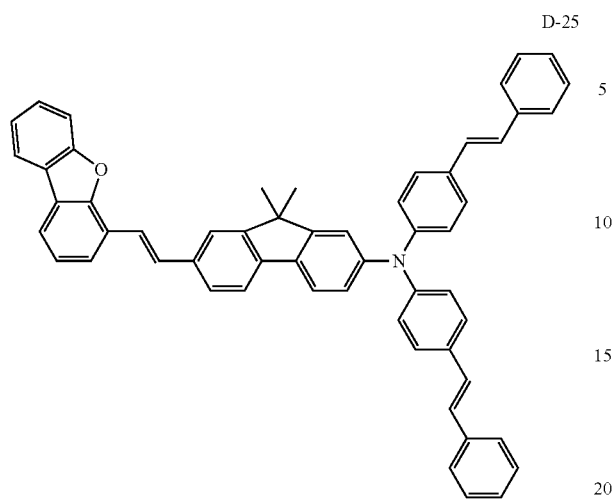
D-25
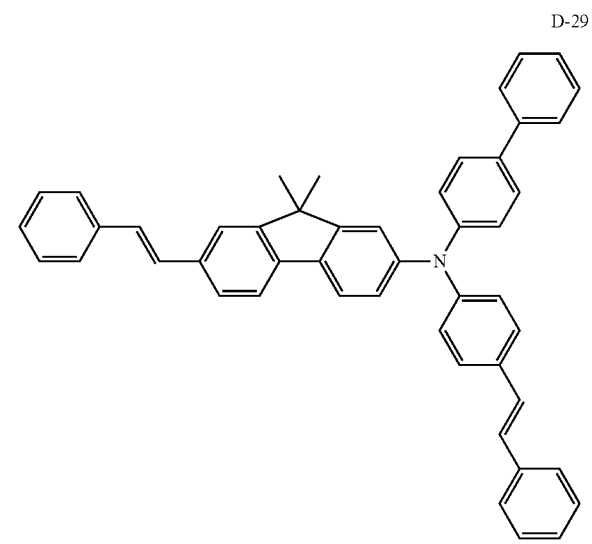
D-29
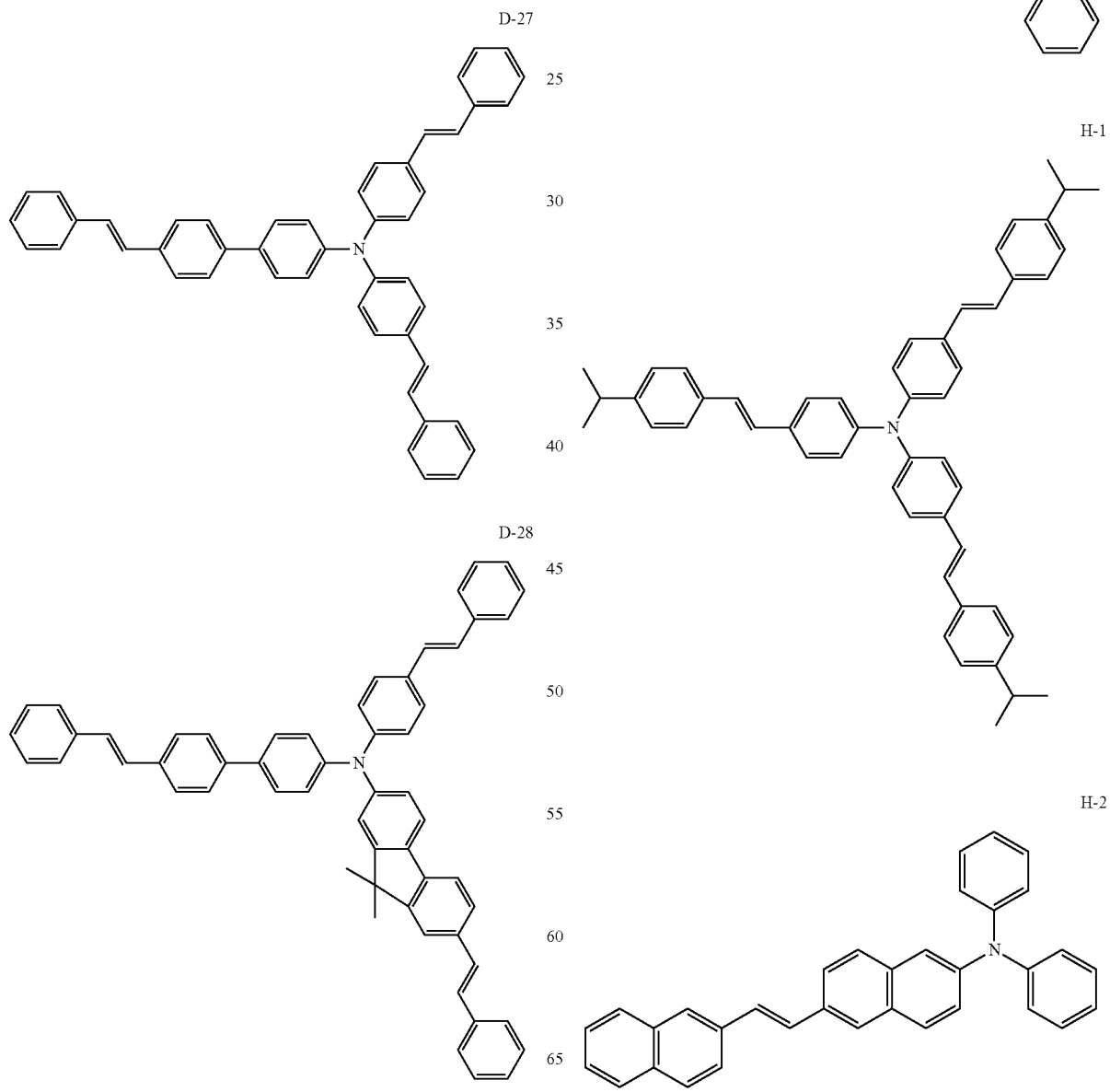

-continued
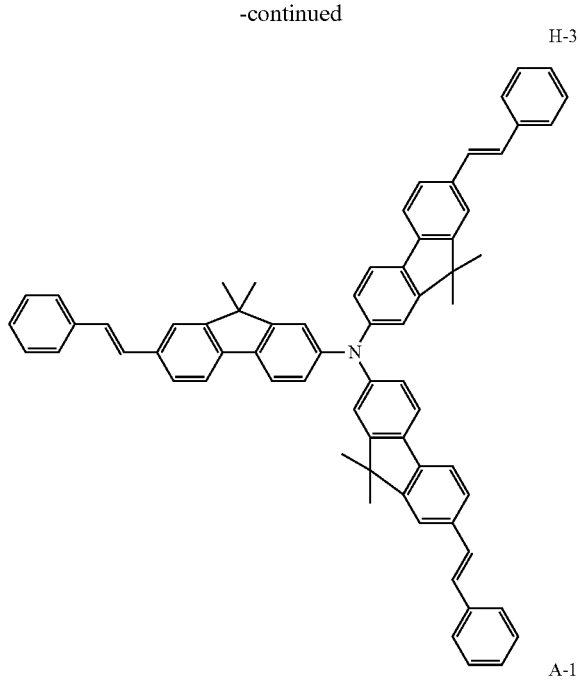
Synthesis Example 1
Compound D-1 was synthesized according to the following steps.
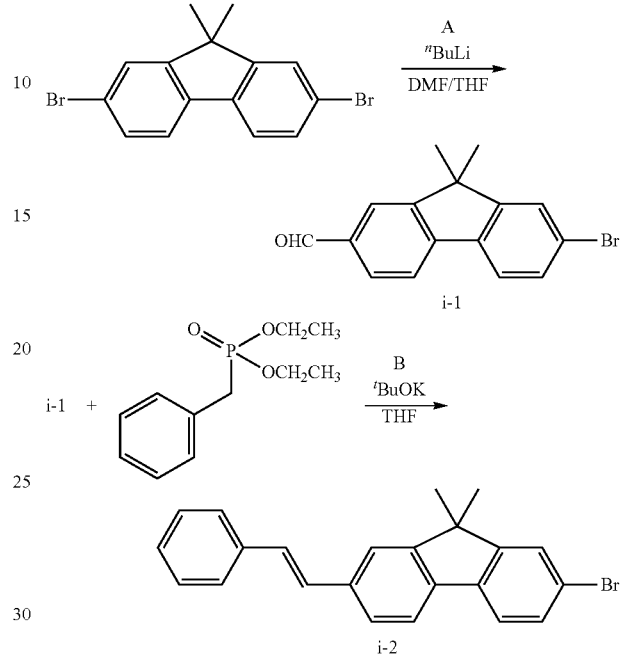
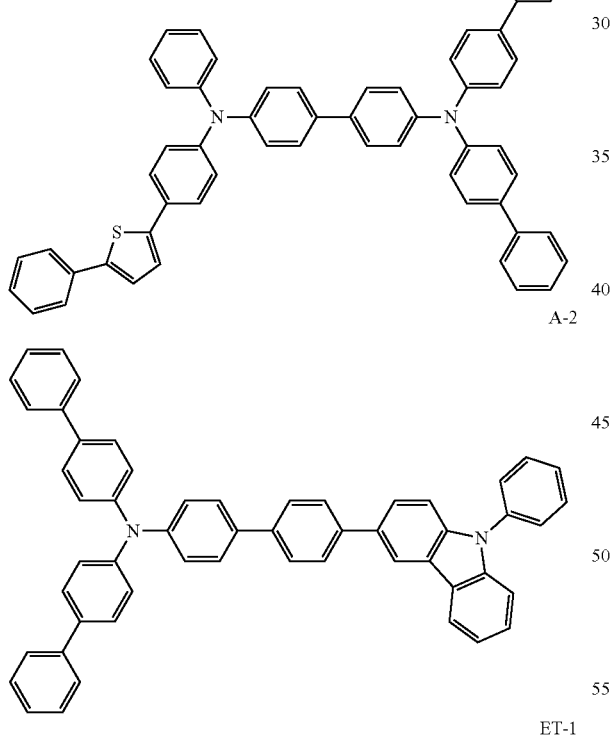
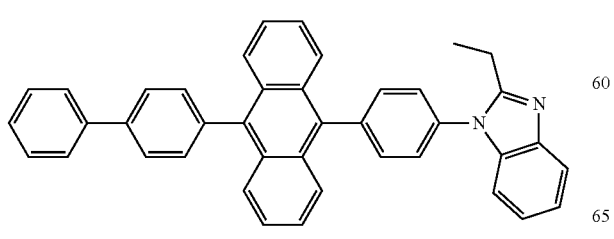
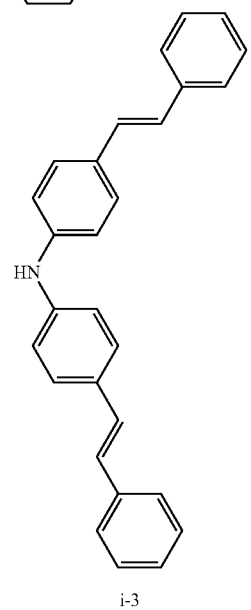

147

-continued i-2 + i-3 →(D, Pd(OAc)₂, P(ᵗBu)₃, NaOᵗBu, toluene)

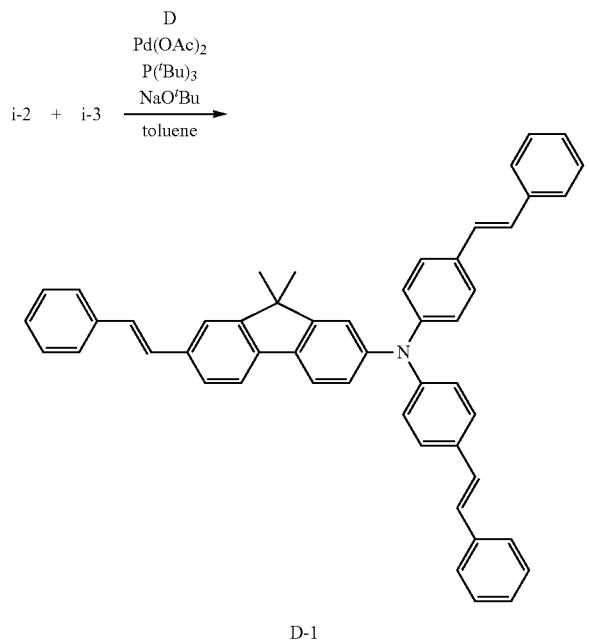

D-1

Synthesis A

Synthesis of Intermediate i-1

In the stream of argon, 30.0 g of 2,7-dibromo-9,9-dimethylfluorene and 340 mL of dehydrated THF were put in a 1000 mL-recovery flask, and the resulting solution was cooled to −65° C. Then, 57 mL (1.65 M) of a hexane solution of n-butyllithium was added thereto, and the resulting mixture was allowed to react for 1 hour. To this reaction liquid, 18 mL of dehydrated N,N-dimethylformamide was added dropwise. The resulting mixture was heated gradually, and allowed to react at room temperature for further 3 hours.

The reaction liquid thus obtained was separated and extracted by adding 3N hydrochloric acid and ethyl acetate, and the organic phase was washed with clean water and saturated saline, dried with sodium sulfate and concentrated to obtain a crude product. The crude product was purified with silica gel chromatography (n-hexane/methylene chloride=2/1), and solids obtained were dried under reduced pressure to obtain 17.2 g of white solids.

The solids were identified as intermediate i-1 by FD-MS (field desorption mass spectrometry) analysis.

Synthesis B

Synthesis of Intermediate i-2

In the stream of argon, 15.7 g of diethyl benzylphosphonate and 100 mL of THF were put in a 1000 mL-recovery flask, and the resulting solution was cooled to −65° C. Then, 9.1 g of potassium tert-butoxide was added thereto, and the resulting mixture was allowed to react for 90 minutes. Subsequently, to this reaction liquid, 180 mL of a THF solution in which 17.2 g of intermediate i-1 was dissolved was added dropwise, and the resulting mixture was allowed to react for two hours. The reaction liquid was heated with stirring to room temperature over 1 hour, and was allowed to react at room temperature for further 2 hours.

The resulting reaction liquid was separated into an aqueous phase and an organic phase by adding clean water and toluene. After extracting the aqueous phase with toluene, the toluene and the organic phase were mixed and washed with clean water and saturated saline, dried with sodium sulfate and concentrated. The resulting solids were re-crystallized from toluene, and the solids thus obtained were dried under reduced pressure, whereby 19.7 g of yellowish white solids were obtained.

The solids were identified as intermediate i-2 by FD-MS (field desorption mass spectrometry) analysis.

Synthesis C

Synthesis of Intermediate i-3

In the stream of argon, 10.0 g of 4-bromostilbene, 22.6 g of 4-aminostilbene, 0.50 g of tris(dibenzylideneacetone)dipalladium(0) [Pd₂(dba)₃], 0.7 g of 2,2'-bis(diphenylphosphino)-1,1'-binaphthyl [BINAP], 7.4 g of sodium tert-butoxide and 200 mL of dehydrated toluene were put in a 500 mL-recovery flask. A reaction was conducted at 100° C. for 6 hours.

After cooling, the reaction solution was filtered, and the resulting solids were washed with toluene, methanol and clean water, and then dried under reduced pressure, whereby 14.0 g of solids were obtained.

The solids were identified as intermediate i-3 by FD-MS analysis.

Synthesis D

Synthesis of Compound D-1

In the stream of argon, 5.4 g of intermediate i-2, 5.3 g of intermediate i-3, 2.8 g of sodium tert-butoxide, 100 mg of palladium acetate (II) [Pd(OAc)₂], 91 mg of tri-tert-butylphosphine and 70 mL of dehydrated toluene were put in a 300 mL-recovery flask. The resulting mixture was allowed to react at 90° C. for 8 hours.

After cooling, the reaction solution was filtered through cellite. The filtrate was concentrated. A crude product obtained was purified by silica gel column chromatography (toluene/hexane=3/7). Solids obtained were re-crystallized from toluene, and the resulting solids were dried under reduced pressure, whereby 5.8 g of yellowish white solids were obtained.

The yellowish white solids were identified as compound D-1 by FD-MS analysis.

The UV absorption maximum wavelength λmax and the flurescence emission maximum wavelength λmax of compound D-1 in the toluene solution are given below.

FDMS, calcd for C51H41N=667. found m/z=667 (M+).

UV(PhMe); λmax=397 nm, FL(PhMe, λex=370 nm); λmax=441 nm

Synthesis Example 2

Compound D-2 was synthesized according to the following steps.

i-2 + 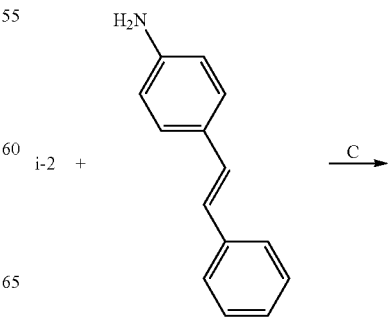 →C

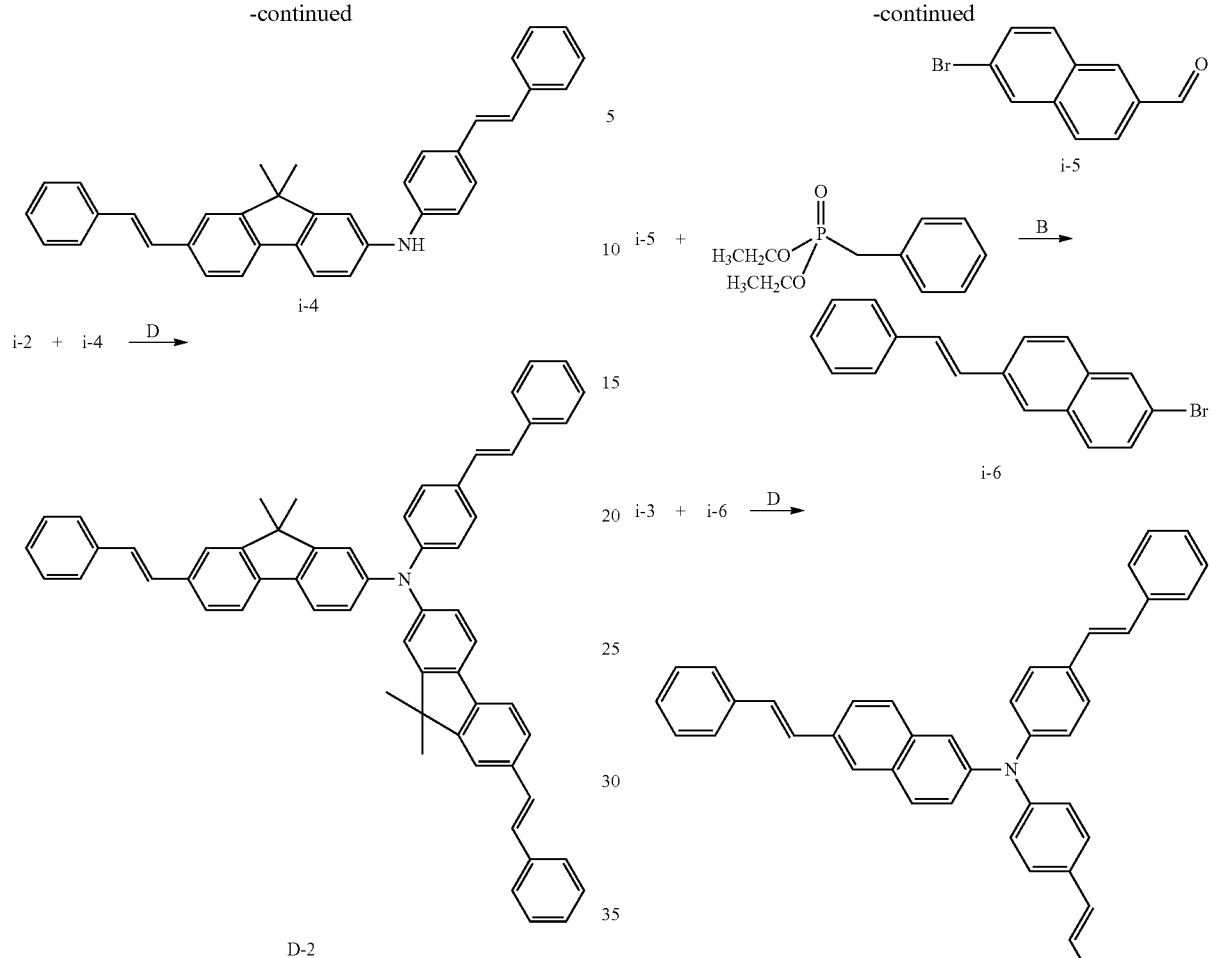

D-2

Synthesis of Intermediate i-4

Intermediate i-4 was synthesized in the same manner as in the synthesis C of Synthesis Example 1, except that intermediate i-2 was used instead of 4-bromostilbene.

The structure of intermediate i-4 was identified by FD-MS analysis.

Synthesis of Compound D-2

Compound D-2 was synthesized in the same manner as in synthesis D of Synthesis Example 1, except that intermediate i-4 was used instead of intermediate i-3.

The structure of compound D-2 was identified by FD-MS analysis.

The UV absorption maximum wavelength λmax and the flurescence emission maximum wavelength λmax of compound D-2 in the toluene solution are given below.

FDMS, calcd for C60H49N=783. found m/z=783 (M+).
UV(PhMe); λmax=404 nm, FL(PhMe, λex=370 nm); λmax=445 nm

Synthesis Example 3

Compound D-3 was synthesized according to the following steps.

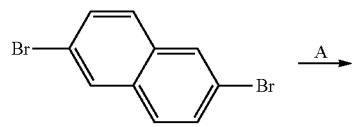

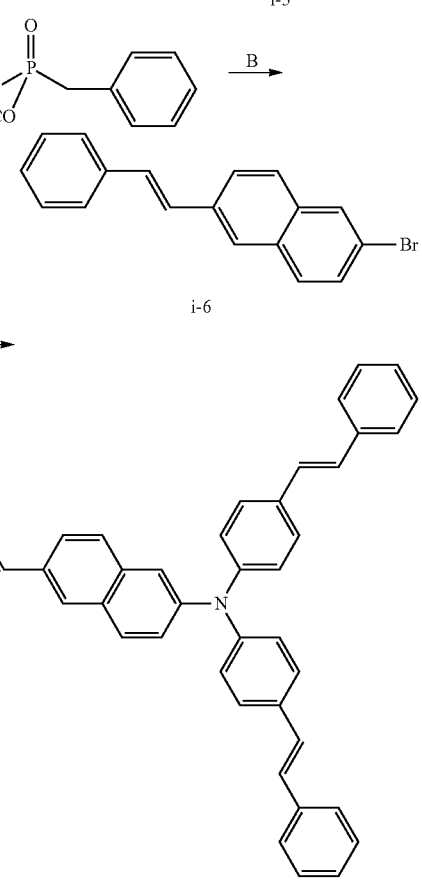

D-3

Synthesis of Intermediate i-5

Intermediate i-5 was synthesized in the same manner as in synthesis A of Synthesis Example 1, except that 2,6-dibromonaphthalene was used instead of 2,7-dibromo-9,9-dimethylfluorene.

The structure of intermediate i-5 was identified by FD-MS analysis.

Synthesis of Intermediate i-6

Intermediate i-6 was synthesized in the same manner as in synthesis B of Synthesis Example 1, except that intermediate i-5 was used instead of intermediate i-1.

The structure of intermediate i-6 was identified by FD-MS analysis.

Synthesis of Compound D-3

Compound D-3 was synthesized in the same manner as in synthesis D of Synthesis Example 1, except that intermediate i-6 was used instead of intermediate i-2.

The structure of compound D-3 was identified by FD-MS analysis.

The UV absorption maximum wavelength λmax and the flurescence emission maximum wavelength λmax of compound D-3 in the toluene solution are given below.

FDMS, calcd for C46H35N=601. found m/z=601 (M+).

UV(PhMe); λmax=395 nm, FL(PhMe, λex=370 nm); λmax=442 nm

Synthesis Example 4

Compound D-4 was synthesized according to the following procedure.

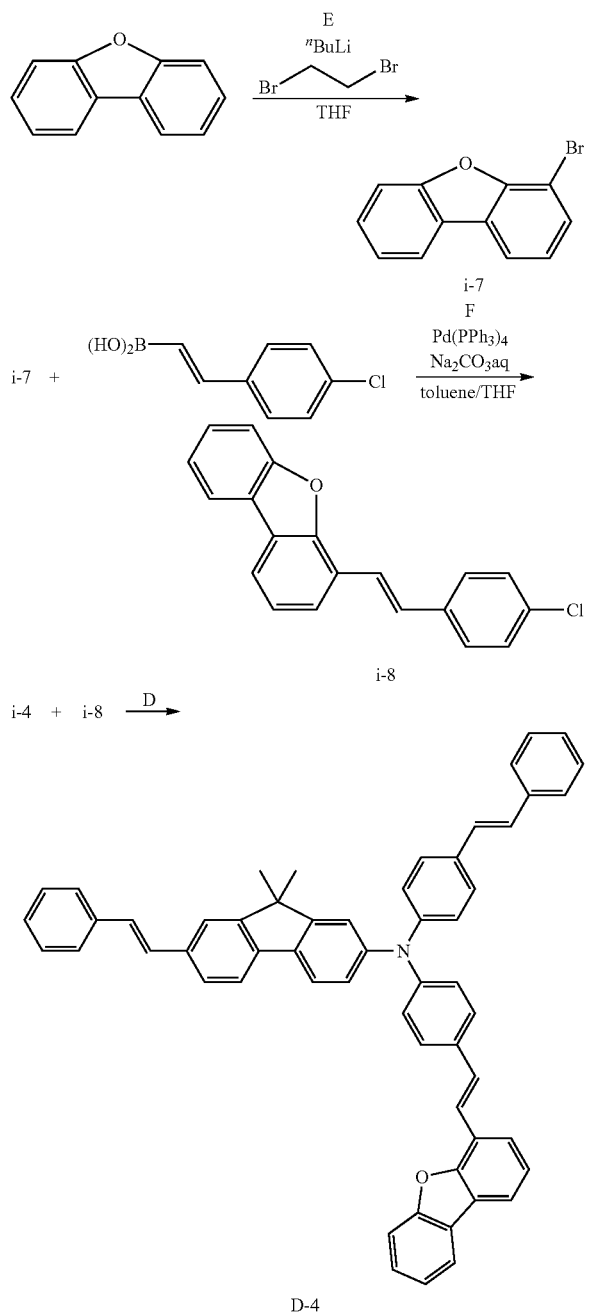

Synthesis E

Synthesis of Intermediate i-7

In the stream of argon, 15.0 g of dibenzofuran and 180 mL of dehydrated THF were put in a 500 mL-recovery flask, and the resulting solution was cooled to −65° C. To this reaction liquid, 60 mL (1.65 M) of a hexane solution of n-butyllithium was added thereto. The resulting mixture was heated gradually, and allowed to react at room temperature for 3 hours. After the reaction liquid was cooled again to −65° C., 11.5 mL of 1,2-dibromoethane was added dropwise. The resulting mixture was heated gradually, and allowed to react at room temperature for 3 hours. The reaction liquid was separated and extracted by adding 2N hydrochloric acid and ethyl acetate, and then the organic phase was washed with clean water and saturated saline and dried with sodium sulfate, and concentrated to obtain a crude product. The crude product was purified with silica gel chromatography (methylene chloride), and solids obtained were dried under reduced pressure to obtain 20.1 g of white solids.

The solids were identified as intermediate i-7 by FD-MS analysis.

Synthesis F

Synthesis of Intermediate i-8

In the stream of argon, 8.0 g of intermediate i-7, 7.7 g of trans-2-(4-chlorophenyl)vinylboronic acid, 0.75 g of tetrakis (triphenylphosphine)palladium(0) [Pd(PPh3)4], 10.3 g of sodium carbonate (clean water 49 mL), 60 mL of dehydrated toluene and 60 mL of dehydrated THF were put in a 500 mL-recovery flask. The resulting mixture was allowed to react at 90° C. for 8 hours in the stream of argon. The reaction liquid was separated by adding clean water and toluene, and the aqueous phase was extracted with toluene. An organic phase obtained by mixing was washed with clean water and saturated saline, and dried with sodium sulfate, and concentrated to obtain a crude product. The crude product was purified with silica gel chromatography (toluene/hexane=1/19), and solids obtained were dried under reduced pressure to obtain 8.4 g of white solids.

The white solids were identified as intermediate i-8 by FD-MS analysis.

Synthesis of Compound D-4

Compound D-4 was synthesized in the same manner as in synthesis D of Synthesis Example 1, except that intermediate i-8 was used instead of intermediate i-2 and intermediate i-4 was used instead of intermediate i-3.

The structure of compound D-4 was identified by FD-MS analysis.

The UV absorption maximum wavelength λmax and the flurescence emission maximum wavelength λmax of compound D-4 in the toluene solution are given below.

FDMS, calcd for C57H43NO=757. found m/z=757 (M+).

UV(PhMe); λmax=402 nm, FL(PhMe, λex=370 nm); λmax=449 nm

Synthesis Example 5

Compound D-5 was synthesized according to the following procedure.

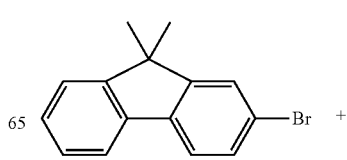

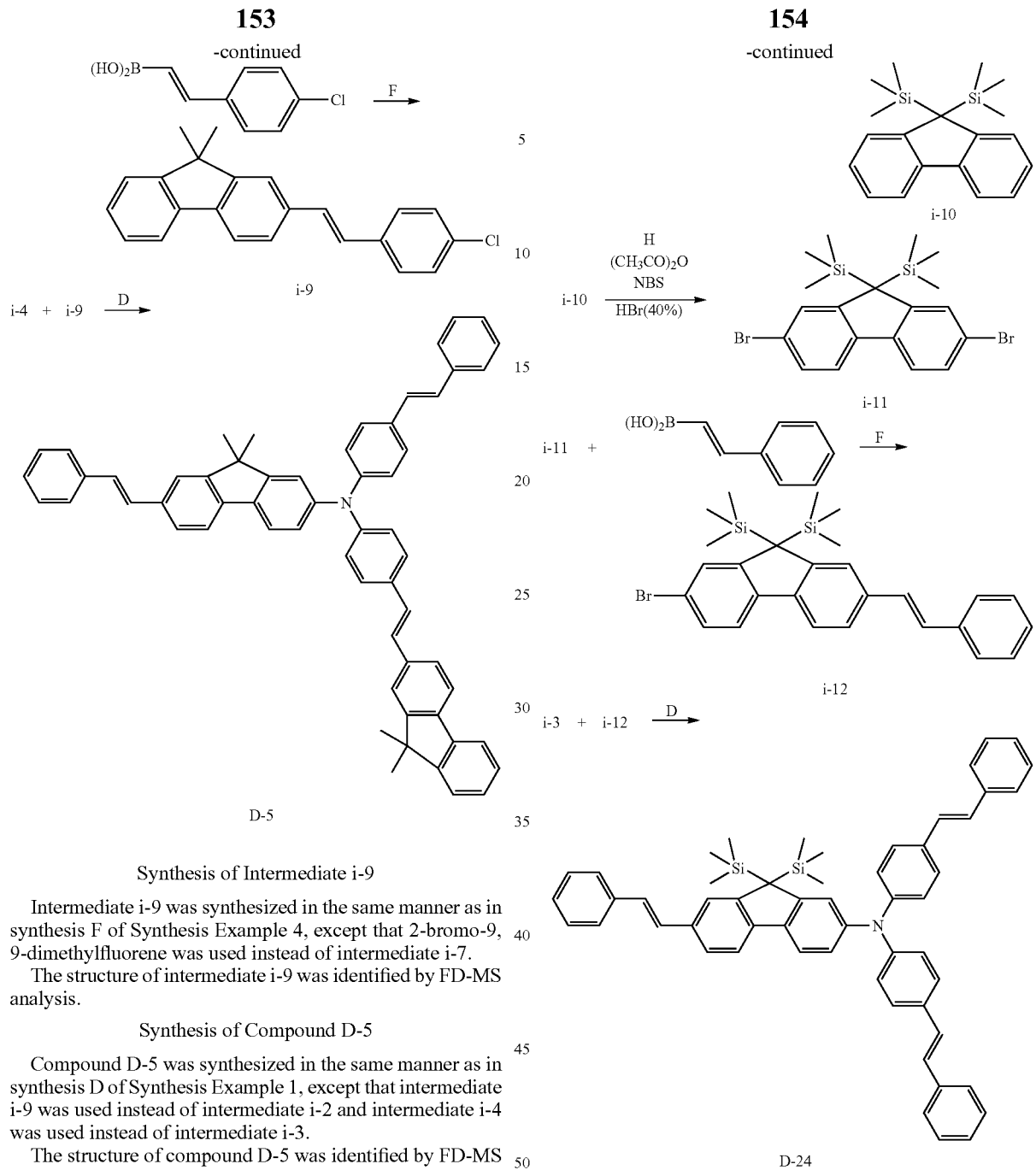

Synthesis of Intermediate i-9

Intermediate i-9 was synthesized in the same manner as in synthesis F of Synthesis Example 4, except that 2-bromo-9,9-dimethylfluorene was used instead of intermediate i-7.

The structure of intermediate i-9 was identified by FD-MS analysis.

Synthesis of Compound D-5

Compound D-5 was synthesized in the same manner as in synthesis D of Synthesis Example 1, except that intermediate i-9 was used instead of intermediate i-2 and intermediate i-4 was used instead of intermediate i-3.

The structure of compound D-5 was identified by FD-MS analysis.

The UV absorption maximum wavelength λmax and the flurescence emission maximum wavelength λmax of compound D-5 in the toluene solution are given below.

FDMS, calcd for C60H49N=783. found m/z=783 (M+).
UV(PhMe); λmax=404 nm, FL(PhMe, λex=370 nm); λmax=452 nm Synthesis Example 6

Compound D-24 was synthesized according to the following steps.

Synthesis Example G

Synthesis of Intermediate i-10

In the stream of argon, 35.0 g of fluorene and 1000 mL of dehydrated THF were put in a 2000 mL-recovery flask, and the resulting solution was cooled to −65° C. To this reaction liquid, 140 mL (1.65 M) of a hexane solution of n-butyllithium was added, and the resulting mixture was allowed to react for 1 hour. Then, 35 mL of trimethylsilylchloride was added dropwise, and the resulting mixture was gradually heated, and allowed to react at room temperature for 4 hours.

The reaction liquid was separated and extracted by adding clean water and toluene, and then the organic phase was washed with an aqueous sodium carbonate solution and saturated saline, dried with sodium sulfate and concentrated to obtain solids. The solids were dried under reduced pressure, and was allowed to react and purified again under the above-mentioned conditions to obtain a crude product. The resulting crude product was purified with silica gel chromatography (n-hexane), and solids obtained were dried under reduced pressure to obtain 61.7 g of white solids. The solids were identified as intermediate i-10 by FD-MS analysis.

Synthesis Example H

Synthesis of Intermediate i-11

In the stream of argon, 60.0 g of intermediate i-10, 79.2 g of N-bromosuccinimide and 1350 mL of acetic anhydride were put in a 3000 mL-recovery flask. To this reaction liquid, 15 mL of hydrogen bromide (40%) was added dropwise, and the resulting mixture was allowed to react at room temperature for 7 hours.

To the reaction liquid, clean water was added and filtered to obtain solids. The solids thus obtained were re-crystallized twice from acetone, and the resulting solids were dried under reduced pressure, whereby 30.0 g of white solids were obtained. The white solids were identified as intermediate i-11 by FD-MS analysis.

Synthesis of Intermediate i-12

Intermediate i-12 was synthesized in the same manner as in synthesis F of Synthesis Example 4, except that intermediate i-11 was used instead of intermediate i-7 and trans-2-phenylvinylboronic acid was used instead of trans-2-(4-chlorophenyl)vinylboronic acid. The intermediate obtained was identified as intermediate i-12 by FD-MS analysis.

Synthesis of Compound D-24

Compound D-24 was synthesized in the same manner as in synthesis D of Synthesis Example 1, except that intermediate i-12 was used instead of intermediate i-2. The compound obtained was identified as compound D-24 by FD-MS analysis. The results of the FD-MS analysis and the UV absorption maximum wavelength λmax and the flurescence emission maximum wavelength λmax of compound D-24 in the toluene solution are given below.

FDMS, calcd for C55H53NSi2=783. found m/z=783 (M+).

UV(PhMe); λmax=395 nm, FL(PhMe, λex=380 nm); λmax=458 nm

Synthesis Example 7

Compound D-25 was synthesized according to the following procedure.

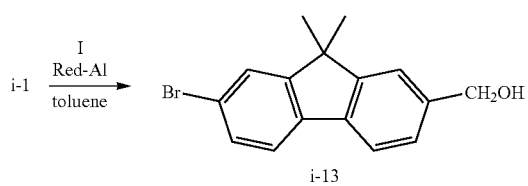

Synthesis Example I

Synthesis of Intermediate i-13

In the stream of argon, 39.4 g of intermediate i-1 and 130 mL of toluene were put in a 2000 mL-recovery flask, and the resulting solution was cooled to 0° C. To this reaction liquid, 43.7 mL of a toluene (70% toluene (3.6M)) solution (260 mL) of sodium bis(2-methoxyethoxy)aluminum hydride was

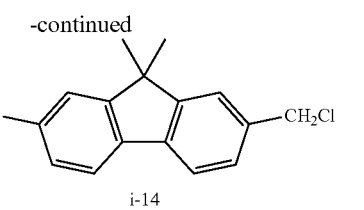

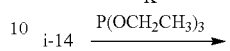

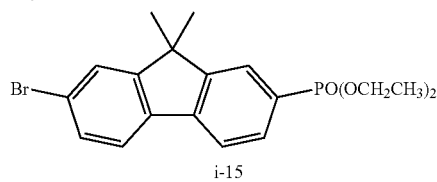

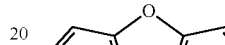

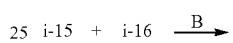

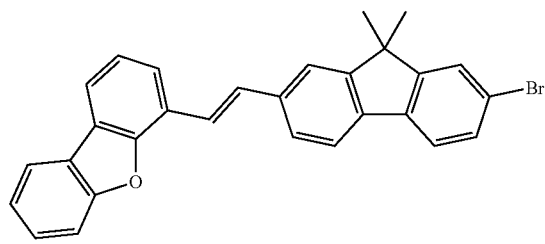

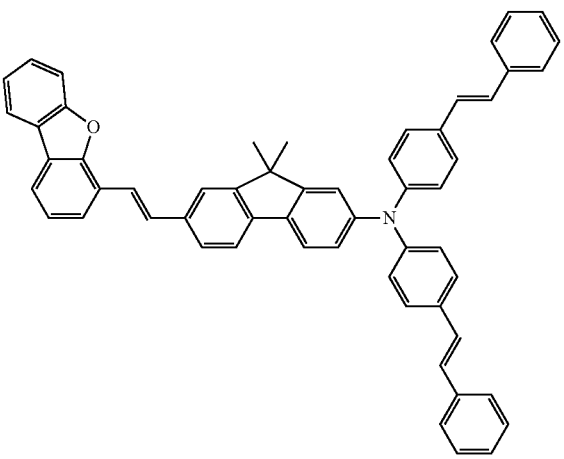

added dropwise. The resulting mixture was heated to room temperature, and allowed to react at room temperature for 3 hours.

The reaction solution was cooled to 0° C., and 3N hydrochloric acid was added dropwise. When the reaction solution became acidic, the solution was separated and extracted by adding ethyl acetate. An organic phase was washed with saturated saline, dried with sodium sulfate and concentrated to obtain solids. The resulting solids were purified with silica gel chromatography (hexane/ethyl acetate (4/1)), and solids obtained were dried under reduced pressure to obtain 37.9 g of white solids. The white solids were identified as intermediate i-13 by FD-MS analysis.

Synthesis J

Synthesis of Intermediate i-14

17.0 g of intermediate i-13 and 180 mL of toluene were put in a 1000 mL-recovery flask. 160 mL of 12N hydrochloric acid was added thereto, and the resulting mixture was allowed to react at room temperature for 72 hours.

The reaction liquid was separated and extracted by adding clean water and toluene. An organic phase was washed with clean water, an aqueous sodium hydrocarbon solution and saturated saline, dried with sodium sulfate and concentrated to obtain solids. The resulting solids were purified with silica gel chromatography (n-hexane/ethyl acetate (10/1)), and solids obtained were dried under reduced pressure to obtain 14.9 g of white solids. The white solids were identified as intermediate i-14 by FD-MS analysis.

Synthesis Example K

Synthesis of Intermediate i-15

In the stream of argon, 14.2 g of intermediate i-14 and 13.8 mL of triethyl phosphite were put in a 500 mL-recovery flask. The resulting mixture was allowed to react at 150° C. for 4 hours.

Triethyl phosphite remained unreacted was removed by distillation under reduced pressure, whereby 17.0 g of colorless liquid was obtained. The liquid was identified as intermediate i-15 by FD-MS analysis.

Synthesis Example L

Synthesis of Intermediate i-16

In the stream of argon, 15.0 g of intermediate i-15 and 370 mL of dehydrated ether were put in a 1000 mL-recovery flask, and the resulting solution was cooled to −65° C. To this reaction liquid, 120 mL of a hexane solution of sec-butyllithium (1.07M) was added, and the resulting mixture was heated to room temperature for 30 minutes and then allowed to react for 1 hour. Subsequently, the reaction liquid was cooled to −65° C., and 8.5 mL of dehydrated N,N-dimethylformamide was added dropwise. The resulting mixture was gradually heated, and allowed to react for 2 hours at room temperature.

The reaction liquid was separated and extracted by adding 3N hydrochloric acid and ethyl acetate, and an organic phase was washed with saturated saline, dried with sodium sulfate and concentrated to obtain solids. The resulting solids were purified with silica gel chromatography (n-hexane/ethyl acetate (20/1)), and solids obtained were dried under reduced pressure to obtain 13.4 g of white solids. The white solids were identified as intermediate i-16 by FD-MS analysis.

Synthesis of Intermediate i-17

Intermediate i-17 was synthesized in the same manner as in synthesis B of Synthesis Example 1, except that intermediate i-16 was used instead of intermediate i-1 and intermediate i-15 was used instead of diethyl benzylphosphonate. The intermediate was identified as intermediate i-17 by FD-MS analysis.

Synthesis of Compound D-25

Compound D-25 was synthesized in the same manner as in synthesis D of Synthesis Example 1, except that intermediate i-17 was used instead of intermediate i-2. The compound was identified as compound D-25 by FD-MS analysis. The results of the FD-MS analysis and the UV absorption maximum wavelength λmax and the florescence emission maximum wavelength λmax of the resulting compound in the toluene solution are given below.

FDMS, calcd for C57H43NO=757. found m/z=757 (M+).

UV(PhMe); λmax=401 nm, FL(PhMe, λex=370 nm); λmax=448 nm

Synthesis Example 8

Compound D-27 was synthesized according to the following steps.

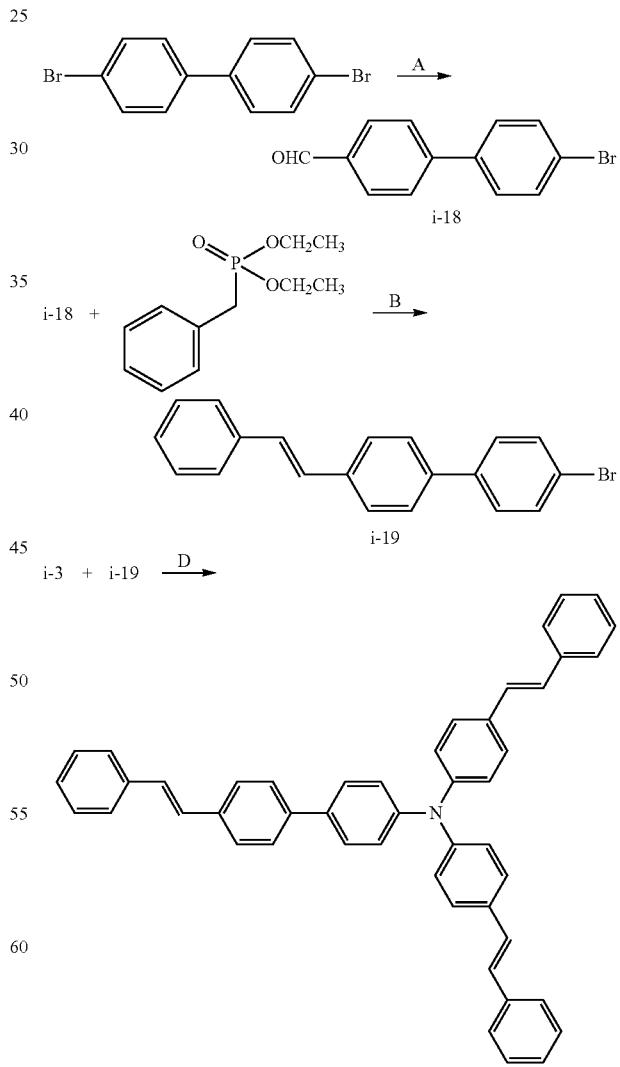

Synthesis of Intermediate i-18

Intermediate i-18 was synthesized in the same manner as in synthesis A of Synthesis Example 1, except that 4,4'-dibromobiphenyl was used instead of 2,7-dibromo-9,9-dimethylfluorene. The intermediate was identified as intermediate i-18 by FD-MS analysis.

Synthesis of Intermediate i-19

Intermediate i-19 was synthesized in the same manner as in synthesis B of Synthesis Example 1, except that intermediate i-18 was used instead of intermediate i-1. The intermediate was identified as intermediate i-19 by FD-MS analysis.

Synthesis of Compound D-27

Compound D-27 was synthesized in the same manner as in synthesis D of Synthesis Example 1, except that intermediate i-19 was used instead of intermediate i-2. The intermediate was identified as compound D-27 by FD-MS analysis. The results of the FD-MS analysis and the UV absorption maximum wavelength λmax and the flurescence emission maximum wavelength λmax of the resulting compound in the toluene solution are given below.

FDMS, calcd for C48H37N=627. found m/z=627 (M+).

UV(PhMe); λmax=387 nm, FL(PhMe, λex=360 nm); λmax=436 nm

Synthesis Example 9

Compound D-28 was synthesized according to the following steps.

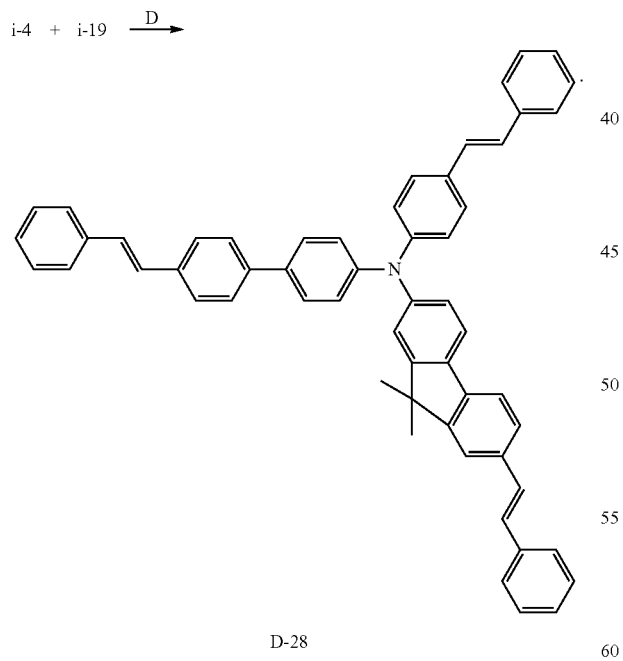

D-28

Synthesis of Compound D-28

Compound D-28 was synthesized in the same manner as in synthesis D of Synthesis Example 1, except that intermediate i-19 was used instead of intermediate i-2 and intermediate i-4 was used instead of intermediate i-3. The compound was identified as compound D-28 by FD-MS analysis. The results of the FD-MS analysis and the UV absorption maximum wavelength λmax and the flurescence emission maximum wavelength λmax of the resulting compound in the toluene solution are given below.

FDMS, calcd for C57H45N=743. found m/z=743 (M+).

UV(PhMe); λmax=392 nm, FL(PhMe, λex=360 nm); λmax=439 nm

Synthesis Example 10

Compound D-29 was synthesized according to the following steps.

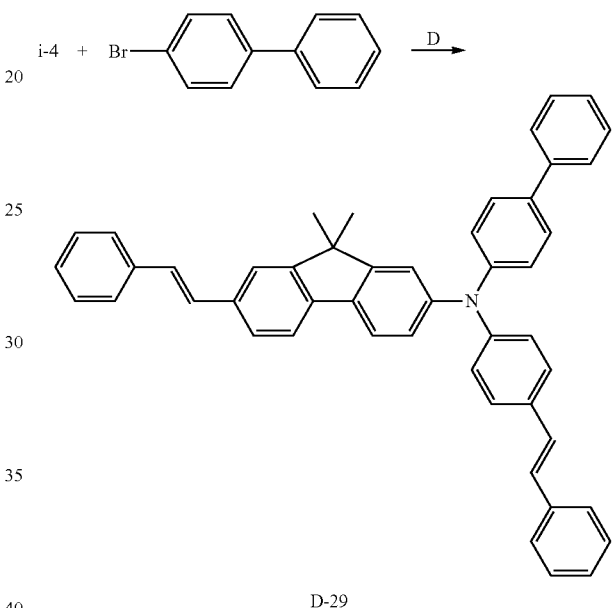

D-29

Synthesis of Compound D-29

Compound D-29 was synthesized in the same manner as in synthesis D of Synthesis Example 1, except that 4-bromobiphenyl was used instead of intermediate i-2 and intermediate i-4 was used instead of intermediate i-3. The compound was identified as compound D-29 by FD-MS analysis. The results of the FD-MS analysis and the UV absorption maximum wavelength λmax and the flurescence emission maximum wavelength λmax of the resulting compound in the toluene solution are given below.

FDMS, calcd for C49H39N=641. found m/z=641 (M+).

UV(PhMe); λmax=385 nm, FL(PhMe, λex=370 nm); λmax=436 nm

Example 1

On a glass substrate with a dimension of 25 mm×75 mm×1.1 mm, a 120 nm-thick transparent electrode formed of indium tin oxide was provided. This transparent electrode functions as an anode. After subjecting to UV-ozone cleaning, the glass substrate was mounted in a vacuum vapor deposition apparatus.

First, a 60 nm-thick film formed of N',N'''-bis[4-(diphenylamino)phenyl]-N',N'''-diphenylbiphenyl-4,4'-diamine was deposited as a hole-injecting layer. Then, a 20 nm-thick film formed of N,N,N',N'-tetrakis(4-biphenyl)-4,4'-benzidine was deposited thereon as a hole-transporting layer. Subsequently, an anthracene derivative (EM2) as a host material and an aromatic amine derivative (D-1) as a doping material were co-deposited in a mass ratio of 40:2 to form a 40 nm-thick emitting layer.

Next, as an electron-injecting layer, a 20 nm-thick film formed of tris(8-hydroxyquinolinato)aluminum was deposited on this emitting layer.

Then, a 1 nm-thick film formed of lithium fluoride was deposited, and a 150 nm-thick film formed of aluminum was deposited, whereby an organic EL device was fabricated. The aluminum/lithium fluoride layer functions as a cathode.

For the organic EL device thus obtained, device performance (luminous efficiency and chromaticity coordinates) at a current density of 10 mA/cm$^2$ and the half life at the initial luminance of 500 cd/cm$^2$ were measured by the following methods. The results are shown in Table 1.

Examples 2 to 10 and Comparative Examples 1 to 3

Organic EL devices were fabricated and evaluated in the same manner as in Example 1, except that the host material and the doping material shown in Tables 1 to 2 were used. The results are shown in Tables 1 to 2.

Example 11

A glass substrate (GEOMATEC CO., LTD.) of 25 mm×75 mm×1.1 mm with an ITO transparent electrode (anode) was subjected to ultrasonic cleaning with isopropyl alcohol for 5 minutes, and cleaned with ultraviolet rays and ozone for 30 minutes. The resultant glass substrate with transparent electrode lines was mounted on a substrate holder in a vacuum vapor deposition apparatus. First, compound A-1 was formed into a film in a thickness of 50 nm on the surface of the transparent electrode on which the transparent electrode lines were formed so as to cover the transparent electrode. Subsequent to the formation of the A-1 film, compound A-2 was formed thereon into a film in a thickness of 45 nm.

Further, on this A-2 film, compound EM13 and compound D-28 of the invention were formed into a film in a thickness of 25 nm with a film thickness ratio of 20:1, whereby a blue emitting layer was formed.

On this film, as an electron-transporting layer, ET-1 having the following structure was formed into a 25 nm-thick film by deposition. Thereafter, LiF was formed into a 1 nm-thick film. Metal Al was deposited in a thickness of 150 nm as a metal cathode, thereby fabricating an organic EL device.

For the organic EL device thus obtained, device performance (external quantum efficiency and chromaticity coordinates) at a current density of 10 mA/cm$^2$ and the half life at the initial luminance of 250 cd/cm$^2$ were measured by the following methods. The results are shown in Table 4.

Examples 12 to 16 and Comparative Example 4

Organic EL devices were fabricated and evaluated in the same manner as in Example 11, except that the host material and the doping material as shown in Table 4 were used. The results are shown in Table 4.

TABLE 1

|  | Example 1 | Example 2 | Example 3 | Example 4 | Example 5 |
|---|---|---|---|---|---|
| Host material | EM2 | EM2 | EM2 | EM2 | EM2 |
| Doping material | D-1 | D-2 | D-3 | D-4 | D-5 |
| Driving voltage [V] | 6.0 | 6.0 | 5.8 | 6.1 | 5.9 |
| CIEx | 0.140 | 0.139 | 0.139 | 0.140 | 0.137 |
| CIEy | 0.122 | 0.135 | 0.129 | 0.133 | 0.155 |
| Luminous efficiency [cd/A] | 6.0 | 6.5 | 5.9 | 6.3 | 8.0 |
| Half life [hour] | >20,000 | >28,000 | >18,000 | >20,000 | >30,000 |

TABLE 2

|  | Example 6 | Example 7 | Example 8 | Example 9 | Example 10 |
|---|---|---|---|---|---|
| Host material | EM32 | EM32 | EM367 | EM367 | EM367 |
| Doping material | D-24 | D-25 | D-27 | D-28 | D-29 |
| Driving voltage [V] | 5.7 | 5.9 | 6.1 | 6 | 6 |
| CIEx | 0.14 | 0.14 | 0.139 | 0.14 | 0.14 |
| CIEy | 0.13 | 0.13 | 0.119 | 0.118 | 0.118 |
| Luminous efficiency [cd/A] | 6.4 | 6.2 | 5.9 | 6.4 | 6.1 |
| Half life [hour] | >18,000 | >21,000 | >18,000 | >20,000 | >22,000 |

TABLE 3

|  | Com. Ex. 1 | Com. Ex. 2 | Com. Ex. 3 |
|---|---|---|---|
| Host material | EM2 | EM2 | EM2 |
| Doping material | H-1 | H-2 | H-3 |
| Driving voltage [V] | 6.2 | 6.0 | 6.2 |
| CIEx | 0.145 | 0.138 | 0.141 |
| CIEy | 0.136 | 0.110 | 0.148 |
| Luminous efficiency | 5.4 | 4.5 | 5.8 |
| Half life [hour] | 10000 | 5000 | 12000 |

TABLE 4

| | Example 11 | Example 12 | Example 13 | Example 14 | Example 15 | Example 16 | Com. Ex. 4 |
|---|---|---|---|---|---|---|---|
| Host material | EM13 | EM32 | EM117 | EM13 | EM32 | EM117 | EM13 |
| Doping material | D-28 | D-28 | D-28 | D-29 | D-29 | D-29 | H-2 |
| Driving voltage [V] | 3.5 | 3.5 | 3.5 | 3.6 | 3.5 | 3.5 | 3.5 |
| CIEx | 0.145 | 0.144 | 0.149 | 0.146 | 0.145 | 0.145 | 0.143 |
| CIEy | 0.860 | 0.850 | 0.080 | 0.080 | 0.080 | 0.078 | 0.100 |
| External quantum efficiency [%] | 7.9 | 8.0 | 7.5 | 7.4 | 7.6 | 7.2 | 4.7 |
| Half life [hour] | >31,000 | >32,000 | >27,000 | >28,000 | >30,000 | >25,000 | 8,000 |

From the results shown in Tables 1 to 4, it can be understood that the blue color purity, luminous efficiency and lifetime of an organic EL device could be improved by using the aromatic amine derivative of the invention. The reason therefor is assumed that the aromatic amine derivative of the invention has an asymmetric luminous center structure.

INDUSTRIAL APPLICABILITY

An organic EL device which uses the aromatic amine derivative of the invention can attain a practically sufficient luminance at a low applied voltage, i.e. has a high luminous efficiency, and is hardly deteriorated even if used for a long period of time, i.e. has a prolonged life time. Therefore, an organic EL device which uses the aromatic amine derivative of the invention can be suitably used as a planar emitting body such as a flat panel display of a wall-hanging television or light sources such as backlight of a display or the like.

Although only some exemplary embodiments and/or examples of this invention have been described in detail above, those skilled in the art will readily appreciate that many modifications are possible in the exemplary embodiments and/or examples without materially departing from the novel teachings and advantages of this invention. Accordingly, all such modifications are intended to be included within the scope of this invention.

The documents described in the specification are incorporated herein by reference in its entirety.

The invention claimed is:

1. An organic electroluminescenece device, comprising:
an aromatic amine compound represented by formula (1):

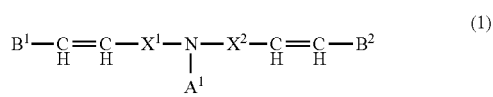

(1)

wherein $A^1$ represents a substituted or unsubstituted alkyl group, a substituted or unsubstituted aromatic group, a substituted or unsubstituted heterocyclic group or an organic group represented by formula (2):

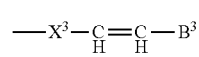

(2)

wherein; $X^1$ represents a substituted or unsubstituted fused aromatic ring group having 10 to 30 ring carbon atoms or a fused heterocyclic group having 10 to 30 ring atoms;
$X^2$ represents a substituted or unsubstituted non-fused aromatic ring group having 6 to 30 ring carbon atoms or a non-fused heterocyclic group having 6 to 30 ring atoms;
$X^3$ represent a substituted or unsubstituted aromatic group or a substituted or unsubstituted heterocyclic group; and
$B^1$, $B^2$ and $B^3$ independently represent a substituted or unsubstituted aromatic group or a substituted or unsubstituted heterocyclic group.

2. The organic electroluminescenece device according to claim 1, wherein the aromatic amine compound is represented by formula (3):

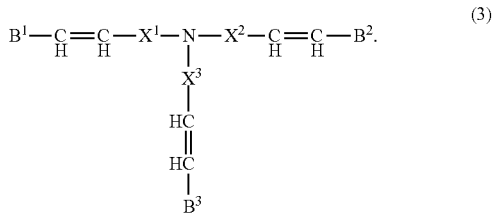

(3)

3. The organic electroluminescenece device according to claim 2, wherein $X^2$ represents a substituted or unsubstituted phenylene group having 6 to 30 ring atoms and
$X^3$ represents a substituted or unsubstituted phenylene group.

4. The organic electroluminescenece device according to claim 1, wherein the aromatic amine compound is represented by formula (4):

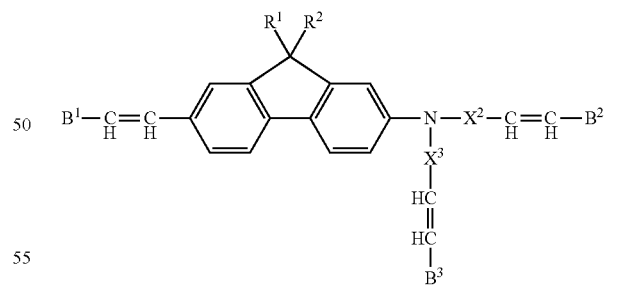

(4)

wherein
$R^1$ and $R^2$ independently represent an alkyl group, an aromatic group, a fluorine atom, an alkoxy group or a substituted or unsubstituted silyl group; and
$R^1$ and $R^2$ are optionally combined with each other to form a saturated or unsaturated ring.

5. The organic electroluminescenece device according to claim 1, wherein the aromatic amine compound is represented by formula (5):

(5)

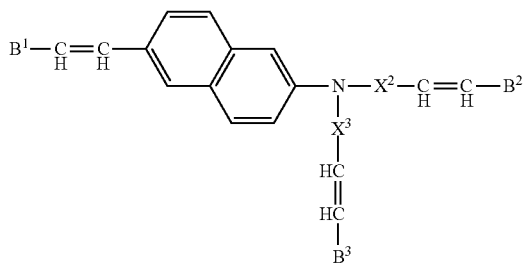

6. The organic electroluminescenece device according to claim 1, wherein A¹ represents a substituted or unsubstituted aromatic group or a substituted or unsubstituted heterocyclic group.

7. The organic electroluminescence device according to claim 1, comprising:
the aromatic amine compound as an emitting material or a hole-transporting material.

8. The organic electroluminescence device according to claim 1, further comprising, between an anode and a cathode;
one or more organic thin film layers comprising an emitting layer, wherein at least one layer of the organic thin film layers comprises the aromatic amine compound.

9. The organic electroluminescence device according to claim 8, wherein the emitting layer comprises the aromatic amine compound.

10. The organic electroluminescence device according to claim 9, wherein the emitting layer comprises at least one of the aromatic amine compound and at least one anthracene compound represented by formula (2A):

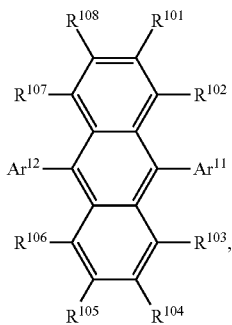

(2A)

wherein Ar¹¹ and Ar¹² independently represent a substituted or unsubstituted monocyclic group having 5 to 50 ring atoms or a substituted or unsubstituted fused ring group having 8 to 50 ring atoms; and
R¹⁰¹ to R¹⁰⁸ independently represent a hydrogen atom, a substituted or unsubstituted monocyclic group having 5 to 50 ring atoms, a substituted or unsubstituted fused ring group having 8 to 50 ring atoms, a substituted or unsubstituted alkyl group having 1 to 50 carbon atoms, a substituted or unsubstituted cycloalkyl group having 3 to 50 ring carbon atoms, a substituted or unsubstituted alkoxy group having 1 to 50 carbon atoms, a substituted or unsubstituted aralkyl group having 7 to 50 carbon atoms, a substituted or unsubstituted aryloxy group having 6 to 50 ring carbon atoms, a substituted or unsubstituted silyl group, a halogen atom or a cyano group.

11. An organic electroluminescenece device, comprising:
an aromatic amine compound represented by formula (1):

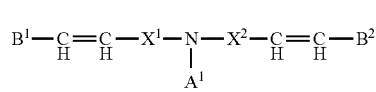

(1)

wherein A¹ represents an organic group represented by formula (2):

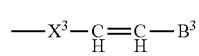

(2)

wherein X¹ and X² independently represent a substituted or unsubstituted aromatic group or a substituted or unsubstituted heterocyclic group;
X¹ and X² represent linkage groups which are different from each other;
X³ represents a substituted or unsubstituted fluorenylene group; and
B¹, B² and B³ independently represent a substituted or unsubstituted aromatic group or a substituted or unsubstituted heterocyclic group.

12. The organic electroluminescence device according to claim 11, comprising:
the aromatic amine compound as an emitting material or a hole-transporting material.

13. The organic electroluminescence device according to claim 11, further comprising, between an anode and a cathode:
one or more organic thin film layers comprising an emitting layer, wherein at least one layer of the organic thin film layers comprises the aromatic amine compound.

14. The organic electroluminescence device according to claim 13, wherein the emitting layer comprises the aromatic amine compound.

15. An organic electroluminescenece device, comprising:
an aromatic amine compound represented by formula (1):

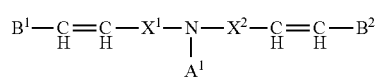

(1)

wherein A¹ represents a substituted or unsubstituted alkyl group, a substituted or unsubstituted aromatic group, a substituted or unsubstituted heterocyclic group or an organic group represented by formula (2):

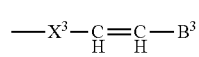

(2)

wherein X¹, X² and X³ independently represent a substituted or unsubstituted aromatic group or a substituted or unsubstituted heterocyclic group,
X¹ and X² represent linkage groups which are different from each other;
B¹, B² and B³ independently represent a substituted or unsubstituted aromatic group or a substituted or unsubstituted heterocyclic group; and
any of the aromatic groups or the heterocyclic groups represented by B¹, B² and B³ has a substituted or unsubstituted silyl group as a substituent.

16. The organic electroluminescence device according to claim 15, wherein the aromatic amine compound is represented by formula (3):

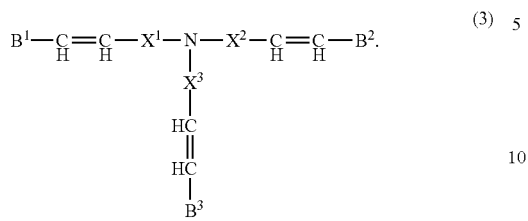

(3)

17. The organic electroluminescence device according to claim 16, wherein $X^2$ and $X^3$ represent substituted or unsubstituted phenylene groups.

18. The organic electroluminescence device according to claim 15, comprising:
the aromatic amine compound as an emitting material or a hole-transporting material.

19. The organic electroluminescence device according to claim 15, further comprising, between an anode and a cathode:
one or more organic thin film layers comprising an emitting layer, wherein at least one layer of the organic thin film layers comprises the aromatic amine compound.

20. The organic electroluminescence device according to claim 19, wherein the emitting layer comprises the aromatic amine compound.

* * * * *